US010696971B2

(12) United States Patent
Dong et al.

(10) Patent No.: US 10,696,971 B2
(45) Date of Patent: Jun. 30, 2020

(54) MRGPRX2/MRGPRB2 EXPRESSING CELL BASED ASSAY TO DETECT PSEUDO-ALLERGIC DRUG REACTIONS AND TO IDENTIFY BLOCKERS TO PREVENT THE ADVERSE REACTIONS

(71) Applicant: The Johns Hopkins University, Baltimore, MD (US)

(72) Inventors: Xinzhong Dong, Clarksville, MD (US); Benjamin McNeil, Washington, DC (US)

(73) Assignee: The Johns Hopkins University, Baltimore, MD (US)

( * ) Notice: Subject to any disclaimer, the term of this patent is extended or adjusted under 35 U.S.C. 154(b) by 435 days.

(21) Appl. No.: 15/329,383

(22) PCT Filed: Jul. 31, 2015

(86) PCT No.: PCT/US2015/043116
§ 371 (c)(1),
(2) Date: Jan. 26, 2017

(87) PCT Pub. No.: WO2016/019246
PCT Pub. Date: Feb. 4, 2016

(65) Prior Publication Data
US 2017/0204419 A1     Jul. 20, 2017

Related U.S. Application Data

(60) Provisional application No. 62/032,350, filed on Aug. 1, 2014.

(51) Int. Cl.
*C12N 15/113*     (2010.01)
*C07K 14/705*    (2006.01)
*C07K 14/72*     (2006.01)
*A61K 31/7105*   (2006.01)
*G01N 33/50*     (2006.01)
*A61K 31/713*    (2006.01)
*A01K 67/027*    (2006.01)
*A61K 45/06*     (2006.01)

(52) U.S. Cl.
CPC ...... *C12N 15/1138* (2013.01); *A01K 67/0276* (2013.01); *A61K 31/713* (2013.01); *A61K 31/7105* (2013.01); *A61K 45/06* (2013.01); *C07K 14/705* (2013.01); *C07K 14/723* (2013.01); *G01N 33/502* (2013.01); *G01N 33/5008* (2013.01); *A01K 2217/075* (2013.01); *A01K 2217/206* (2013.01); *A01K 2227/105* (2013.01); *A01K 2267/0381* (2013.01); *A01K 2267/0393* (2013.01); *C12N 2310/14* (2013.01); *C12N 2320/31* (2013.01); *G01N 2800/24* (2013.01)

(58) Field of Classification Search
CPC ............ C12N 15/1138; C12N 2310/14; A61K 31/7105; A61K 31/713; G01N 33/5008; G01N 2800/24; C07K 14/705; C07K 14/723
See application file for complete search history.

(56) References Cited

U.S. PATENT DOCUMENTS

2005/0164288 A1   7/2005  Anderson et al.
2012/0219968 A1   8/2012  Mancebo et al.

FOREIGN PATENT DOCUMENTS

| EP | 1876239 A1 | 1/2008 |
|----|------------|--------|
| JP | 2002355052 A | 12/2002 |
| JP | 200433211 A | 2/2004 |
| JP | 2005304438 A | 11/2005 |
| JP | 2011511622 A | 4/2011 |
| JP | 2012178985 A | 9/2012 |
| WO | WO-01-11022 A1 | 2/2001 |
| WO | 200116159 A1 | 3/2001 |
| WO | 2005028667 A1 | 3/2005 |
| WO | WO-2010-065085 A2 | 6/2010 |

OTHER PUBLICATIONS

Kamohara et al. Identification of MrgX2 as a human G-protein-coupled receptor for proadrenomedullin N-terminal peptides. Biochemical and Biophysical Research Communications. May 20, 2005, vol. 330, No. 4, pp. 1146-1152.
Tatemoto et al. Immunoglobulin E-independent activation of mast cell is mediated by Mrg receptors, Biochemical and Biophysical Research Communications, Nov. 3, 2006, vol. 349, No. 4, pp. 1322-1328.
McNeil et al. Identification of a mast-cell-specific receptor crucial for pseudo-allergic drug reactions, Nature, Epub. Dec. 17, 2014, vol. 519, No. 7542, pp. 237-241.
English language summary of Office Action (dispatch date: Feb. 6, 2020) and current claim of counterpart Japanese Application 2017-526479.
Ødum, L., et al. "Pituitary adenylate cyclase activating polypeptide (PACAP) is localized in human dermal neurons and causes histamine release from skin mast cells." Inflammation Research 47.12 (1998): 488-492.
International Search Report issued in corresponding International Application No. PCT/US2015/043116, dated Aug. 1, 2006 (8 pages).
English language summary of Office Action dated May 30, 2019 in counterpart Japan application 2017/526479.
English language summary of first Office Action issued in counterpart China Application CN201580053612.
Robas, Nicola, Emma Mead, and Mark Fidock. "MrgX2 is a high potency cortistatin receptor expressed in dorsal root ganglion." Journal of Biological Chemistry 278.45 (2003): 44400-44404.

(Continued)

*Primary Examiner* — Ruixiang Li
(74) *Attorney, Agent, or Firm* — Mintz Levin Cohn Ferris Glovsky and Popeo, P.C.; Peter F. Corless

(57) ABSTRACT

The present invention relates to cells and methods for detecting compounds that induce a pseudo-allergic-type reaction and methods for reducing the severity of a pseudo-allergic-type reaction.

16 Claims, 38 Drawing Sheets

(56) References Cited

OTHER PUBLICATIONS

Subramanian, Hariharan, Kshitij Gupta, and Hydar Ali. "Roles of Mas-related G protein-coupled receptor X2 on mast cell-mediated host defense, pseudoallergic drug reactions, and chronic inflammatory diseases." Journal of Allergy and Clinical Immunology 138.3 (2016): 700-710.

Okayama, Yoshimichi, Hirohisa Saito, and Chisei Ra. "Targeting human mast cells expressing g-protein-coupled receptors in allergic diseases." Allergology International 57.3 (2008): 197-203.

Kashem, Sakeen W., et al. "G protein coupled receptor specificity for C3a and compound 48/80-induced degranulation in human mast cells: roles of Mas-related genes MrgX1 and MrgX2." European journal of pharmacology 668.1-2 (2011): 299-304.

FIG. 4A
48/80 monomer
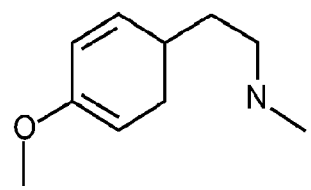
cyclized monomer
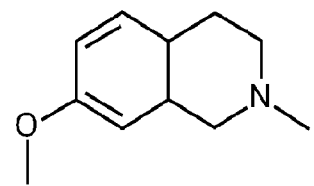

FIG. 5C

| | X2 | b2 | b1 | b10 | b11 |
|---|---|---|---|---|---|
| PAMP (50 µM) | ✓ | ✓ | x | x | x |
| 48/80 (20 µg/ml) | ✓ | ✓ | x | x | x |
| Cort. (20 µM) | ✓ | ✓ | x | x | x |
| Sub. P (100 µM) | ✓ | ✓ | x | x | x |
| CQ (100 µM) | x | x | x | x | x |

FIG. 6C

| Substance | Mrgprb2 ED$_{50}$ | MRGPRX2 EC$_{50}$ |
|---|---|---|
| Compound 48/80 | 3.7 ± 0.5 µg/ml | 470.1 ± 139.6 ng/ml |
| Substance P | 54.3 ± 4.9 µM | 152.3 ± 48.0 nM |
| Cortistatin-14 | 21.3 ± 0.9 µM | 106.7 ± 39.3 nM |
| PAMP (9-20) | 12.4 ± 1.6 µM | 166.0 ± 35.7 nM |
| Mastoparan | 24.0 ± 3.6 µM | 3.9 ± 0.7 µM |
| Icatibant | 32.5 ± 2.0 µg/ml | 15.8 ± 2.7 µg/ml |
| Cetrorelix | 23.4 ± 1.4 µg/ml | 221.7 ± 63.1 ng/ml |
| Sermorelin | 29.1 ± 1.2 µg/ml | 4.5 ± 0.9 µg/ml |
| Octreotide | 10.0 ± 1.1 µg/ml | 6.6 ± 0.7 µg/ml |
| Leuprolide | 152.0 ± 7.1 µg/ml | 9.1 ± 0.7 µg/ml |
| Atracurium | 44.8 ± 1.4 µg/ml | 28.6 ± 2.4 µg/ml |
| Rocuronium | 22.2 ± 3.3 µg/ml | 261.3 ± 14.4 µg/ml |
| Ciprofloxacin | 126.5 ± 5.1 µg/ml | 6.8 ± 0.5 µg/ml |
| Moxifloxacin | 14.1 ± 2.1 µg/ml | 9.9 ± 0.6 µg/ml |
| Levofloxacin | 807.6 ± 47.1 µg/ml | 22.7 ± 0.4 µg/ml |
| Ofloxacin | 225.0 ± 25.4 µg/ml | 30.1 ± 1.5 µg/ml |

FIG. 9D

```
atgagtggagatttcctaatcaagatctaagcacctcagcctggaaaacgaacatcaca
 M  S  G  D  F  L  I  K  N  L  S  T  S  A  W  K  T  N  I  T
gtgctgaatggaagctactacatcgatacttcagttgtcaccaggaaccaagccatg
 V  L  N  G  S  Y  Y  I  D  T  S  V  C  V  T  R  N  Q  A  M
                                          TM1
atttgctttccatcatcatttccctggttgggatgggactaaatgccatagtgctgtgg
 I  L  S  I  I  H  I  S  L  V  G  M  G  L  N  A  I  V  L  W
                    ┌─> Mut
ttcctgggcatccgcacgaatgcctcactgtctacattctcaacctggctatggctg
 F  L  G  I  R  T  R  M  P  S  L  S  T  F  S  T  W  L  W  L
actttcttacctgtgctctcagtttgtas
 T  F  F  T  C  A  L  S  L  *
```

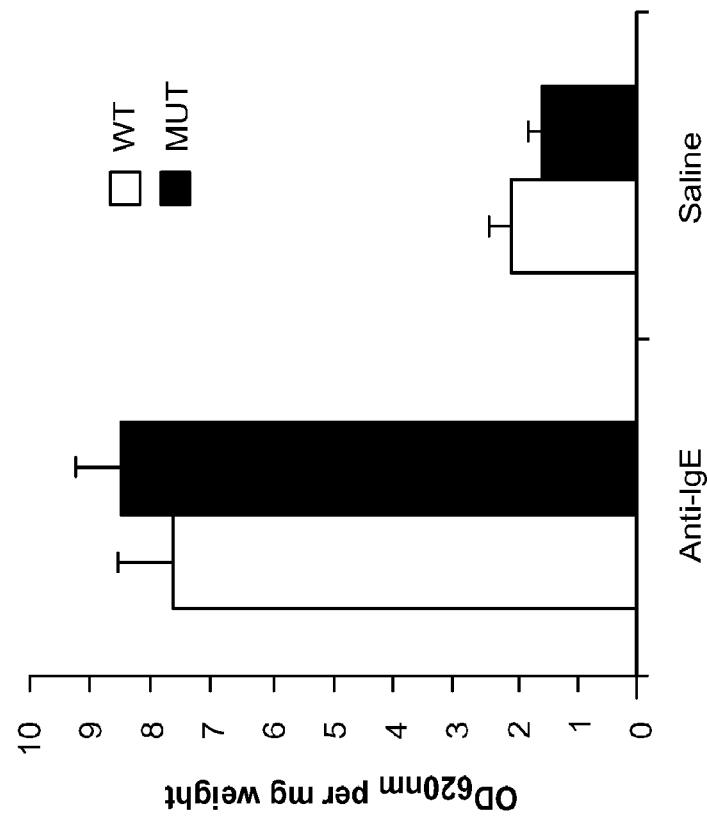
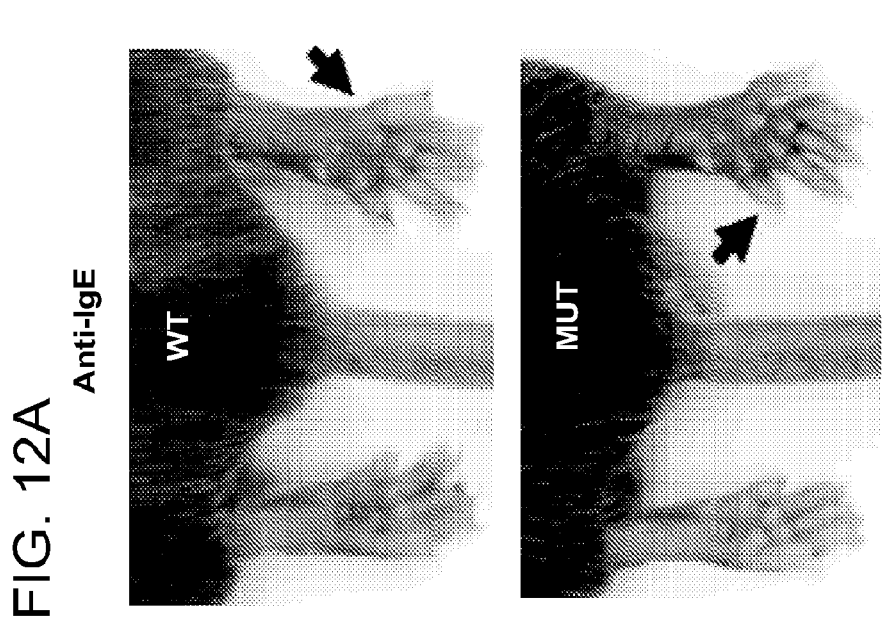
FIG. 12A
FIG. 12B

FIG. 15A
Cationic peptidergic drug families

| class | name | Treatment for | Net charge | Dosage or concentration | Route | ISRs? |
|---|---|---|---|---|---|---|
| GnRH receptor agonists | | | | | | |
| | Leuprolide | Prostate cancer | +1 | 5 mg/ml (for daily injection) | SC | |
| | Goserelin | Prostate carcinoma | +2 | 3.6-10.8 mg | SC depot | 25% |
| | Histrelin | Precocious puberty, prostate cancer | +1 | 50 mg | SC implant | ND, pain reported |
| | Triptorelin | Advamced prostate cancer | +1 | 1.8-11.25 mg | SC depot | 51% implant reactions |
| GnRH receptor antagonists | | | | | | 6% |
| | Cetrorelix | Assisted fertilization | +1 | 0.25-3 mg/ml | SC | Up to 94% |
| | Ganirelix | Assisted fertilization | +1 | 0.5 mg/ml | SC | Up to 12.5% |
| | Degarelix | Advamced prostate cancer | +1 | 20-40 mg/ml | SC depot | Up to 44% |
| Somatostatin mimics | | | | | | |
| | Octreotide | Acromegaly, symptoms of carcinoid tumors, VIP adenoma | +2 | 0.05-1 mg/ml | SC, IM, IV | Up to 38% |
| | Lanreotide | acromegaly | +2 | 60-120 mg/ml | SC depot | Up to 22% |
| | Pasireotide | Cushing's disease | +2 | 0.3-0.9 mg/ml | SC | 17% |
| GHRH mimics | | | | | | |
| | Sermorelin | Accelerating growth in children | +3 | 0.25-1.5 mg/ml | SC | ~15% |
| | Tesamorelin | HIV-associated lipodystrophy | +4 | 1 mg/ml | SC | Up to 24.5% |

FIG. 15B
Other cationic peptidergic drugs

| class | name | Treatment for | Net charge | Dosage or concentration | Route | ISRs? |
|---|---|---|---|---|---|---|
| Bradykinin receptor antagonist | Icatibant | Hereditary angioedema | +3 | 10 mg/ml | SC | 97-100% |
| Myelin basic protein mimic | Glatiramer acetate | Multiple sclerosis | +2 | 20 mg/ml | SC | > 40% |
| Parathyroid hormone | Teriparatide | osteoporosis | +2 | 0.25 mg/ml | SC | 5% reported rash |
| Amylin mimic | Pramlintide | diabetes | +2 | 0.6 mg/ml | SC | ND |
| Glycopeptide antibiotic | Bleomycin | Carcinomas and lymphomas | +2 | 3-15 mg/ml | IV, IM, SC | 50% |

Neutral and anionic peptidergic drugs

| class | name | Treatment for | Net charge | Dosage or concentration | Route | ISRs? |
|---|---|---|---|---|---|---|
| Glucagon/GLP-1 mimics | Exenatide | Type II diabetes | -3 | 0.25 mg/ml | SC | <2%, possibly antibody mediated |
|  | Glucagon | Severe hypoglycemia | 0 | 1 mg/ml | IV, IM, SC | - |
|  | Liraglutide | Type II diabetes | -3 | 6 mg/ml | SC | 2% |
| antiretroviral | Enfuviritide | HIV infection | -5 | 90 mg/ml | SC | 98% |
| antibiotic | Colistimethate | Gram-Negative bacterial infections | -5 | 75 mg/ml | IM, IV | Rash reported |

FIG. 16

| Type | Name | Clinical Conc. |
|---|---|---|
| agonist | succinylcholine | 20 mg/ml |
| Non-steroidal antagonist | tubocurarine | --- |
| | atracurium | 10 mg/ml |
| | mivacurium | 2 mg/ml |
| Steroidal antagonist | rocuronium | 5 mg/ml |

MRGPRX2/MRGPRB2 EXPRESSING CELL BASED ASSAY TO DETECT PSEUDO-ALLERGIC DRUG REACTIONS AND TO IDENTIFY BLOCKERS TO PREVENT THE ADVERSE REACTIONS

CROSS REFERENCE TO RELATED APPLICATIONS

This application is a national stage application, filed under 35 U.S.C. § 371, of International Application No. PCT/US2015/043116, filed on Jul. 31, 2015, which claims the benefit of priority under 35 U.S.C. § 119(e) to U.S. Provisional Application No. 62/032,350, filed Aug. 1, 2014. The entire contents of each of which are hereby incorporated by reference in their entireties.

FIELD OF THE INVENTION

The present invention relates to cells and methods for detecting compounds that induce a pseudo-allergic-type reaction and methods for reducing the severity of a pseudo-allergic-type reaction.

BACKGROUND OF THE INVENTION

Many food and drug administration (FDA)-approved drugs are associated with pseudo-allergic-type reactions as part of their side effect profiles. Prior to the invention described herein, cell lines and methods for determining which drugs are likely to cause a pseudo-allergic-type reaction were needed. Additionally, prior to the invention described herein, methods for reducing the severity of a pseudo-allergic-type reaction and screens for discovering antagonists that block these responses were needed.

SUMMARY OF THE INVENTION

The invention is based, in part, on the an isolated cell comprising a recombinant nucleic acid that expresses mas-related G-protein coupled receptor member X2 (MrgprX2) or MrgprB2. For example, the recombinant nucleic acid expresses MrgprX2. Alternatively, the recombinant nucleic acid expresses MrgprB2. In some cases, the cell further comprises a recombinant nucleic acid that expresses GTP-binding protein alpha 15 (Gα15). In other cases, the recombinant nucleic acid that expresses MrgprX2 comprises one or more mutations. For example, the one or more mutations produces an MrgprX2 protein incapable of activating a signal transduction pathway. Alternatively, the recombinant nucleic acid that expresses MrgprB2 comprises one or more mutations. For example, the one or more mutations produces an MrgprB2 protein incapable of activating a signal transduction pathway. In some cases, this cell further comprises a recombinant nucleic acid that expresses GTP-binding protein alpha 15 (Gα15).

Preferably, the isolated cell comprises a human embryonic kidney 293 (HEK 293) cell.

Also provided are methods for reducing the severity of a pseudo-allergic-type reaction in a subject that is induced by administering a compound by administering the compound to a subject; administering an MrgprB2 or MrgprX2 antagonist to the subject, thereby reducing the severity of a pseudo-allergic-type reaction in the subject.

For example, the methods described herein reduce the severity of a pseudo-allergic-type reaction by at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

The subject is preferably a mammal in need of such treatment, e.g., a subject that has been diagnosed with a pseudo-allergic-type reaction or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The inhibitors or antagonists may include but are not limited to nucleic acids, peptides, antibodies, or small molecules that bind to their specified target or the target's natural ligand and modulate the biological activity.

In one aspect, the antagonist comprises an antibody or fragment thereof, a binding protein, a polypeptide, or any combination thereof. Described herein are anti-MrgprX2 antibodies. Suitable anti-MrgprX2 antibodies include SAB2900154-50UG (Sigma-Aldrich®, St. Louis, Mo.), PA5-32930 (Thermo Scientific, Waltham, Mass.), TA317038 (Origene, Rockville, Md.), and 038585 (United States Biological, Boston, Mass.), each of which is incorporated herein by reference. However, the skilled artisan could readily identify additional anti-MrgprX2 (or anti-MrgprB2) antibodies for use in the methods described herein. In some cases, the anti-MrgprX2 (or anti-MrgprB2) antibodies described herein are administered at a concentration of 0.1 µg/ml to 500 mg/ml.

In some cases, the antagonist comprises a small molecule. A small molecule is a compound that is less than 2000 Daltons in mass. The molecular mass of the small molecule is preferably less than 1000 Daltons, more preferably less than 600 Daltons, e.g., the compound is less than 500 Daltons, less than 400 Daltons, less than 300 Daltons, less than 200 Daltons, or less than 100 Daltons.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecules can be synthetically engineered to consist of a fragment, or small portion, or a longer amino acid chain to fill a binding pocket of an enzyme. Typically small molecules are less than one kilodalton.

In some cases, the antagonist comprises a nucleic acid molecule. For example, ribonucleic acid (RNA) or deoxyribonucleic acid (DNA) inhibit the expression of MrgprX2 or MrgprB2 polypeptide, thereby inhibiting the activity of MrgprX2 or MrgprB2. In some cases, the nucleic acid comprises small interfering RNA (siRNA), RNA interference (RNAi), messenger RNA (mRNA), small hairpin RNA or short hairpin RNA (shRNA), double stranded ribonucleic acid (dsRNA), antisense RNA or microRNA, or any portion thereof. Thus, suitable MrgprX2 antagonists include MrgprX2 siRNA and MrgprX2 shRNA, each of which is available from, e.g., Origene, Rockville, Md. or Life Technologies, Grand Island, N.Y., and incorporated herein by reference. Similarly, suitable MrgprB2 antagonists include MrgprB2 siRNA and MrgprB2 shRNA, each of which is available, e.g., Origene, Rockville, Md. or Life Technologies, Grand Island, N.Y., and incorporated herein by reference. However, the skilled artisan could readily identify additional nucleic acids that inhibit/antagonize MrgprX2 or MrgprB2.

The antagonist is administered prior to, simultaneously with, or subsequent to administering the compound to the subject.

A variety of administration routes are available. For example, the antagonist is administered topically, orally, via inhalation, or via injection.

The effective amount of the antagonist is from 0.001 mg/kg to 250 mg/kg body weight, e.g., 0.001 mg/kg, 0.05 mg/kg 0.01 mg/kg, 0.05 mg/kg, 1 mg/kg, 5 mg/kg, 10 mg/kg, 25 mg/kg, 50 mg/kg, 75 mg/kg, 100 mg/kg, 125 mg/kg, 150 mg/kg, 175 mg/kg, 200 mg/kg, 225 mg/kg, or 250 mg/kg body weight. Ultimately, the attending physician or veterinarian decides the appropriate amount and dosage regimen.

In some cases, the antagonist is administered at least once per day, at least once per week, or at least once per month. The antagonist is administered for a duration of one day, one week, one month, two months, three months, six months, 9 months, or one year. In some cases, the antagonist is administered daily, e.g., every 24 hours. Or, the antagonist is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

Methods of treating a pseudo-allergic-type reaction in a subject are carried out by administering an MrgprB2 or MrgprX2 antagonist to the subject, thereby treating the pseudo-allergic-type reaction in the subject.

Methods for determining whether a compound induces a pseudo-allergic-type reaction are carried out by contacting the isolated cell described herein with a candidate compound, detecting activation of MrgprX2 or MrgprB2, wherein activation of MrgprX2 or MrgprB2 determines that the candidate compound induces a pseudo-allergic-type reaction.

For example, activation of MrgprX2 or MrgprB2 is detected by identifying an increase in intracellular calcium relative to the level of intracellular calcium in the absence of the compound. In some cases, the level of intracellular calcium increases by at least 1%, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Intracellular calcium concentration is determined utilizing the methods described herein or those available to the skilled artisan.

Exemplary candidate compounds include leuprolide, goserelin, histrelin, triptorelin, cetrorelix, ganirelix, degarelix, octreotide, lanreotide, pasireotide, sermorelin, tesamorelin, icatibant, glatiramer acetate, teriparatide, pramlintide, bleomycin, exenatide, glucagon, liraglutide, enfuvirtide, and colistimethate.

Other exemplary candidate compounds include succinylcholine, tubocurarine, atracurium, mivacurium, and rocuronium.

A candidate MrgprX2 antagonist is screened to confirm that it counteracts or inhibits, decreases, or suppresses the biological activity of a MrgprX2 polypeptide. Also provided are methods for identifying an antagonist of MrgprX2 or MrgprB2 comprising contacting the isolated cell described herein with a compound that induces a pseudo-allergic-type reaction, contacting the isolated cell described herein with a candidate antagonist, detecting activation of MrgprX2 or MrgprB2, wherein a decrease in activation of MrgprX2 or MrgprB2 relative to the activation of MrgprX2 or MrgprB2 in the absence of the candidate antagonist determines that the candidate compound is an antagonist.

Also provided are methods for identifying an agonist of MrgprX2 or MrgprB2 comprising: contacting the isolated cell described herein with a compound that induces a pseudo-allergic-type reaction, contacting the isolated cell described herein with a candidate agonist, detecting activation of MrgprX2 or MrgprB2, wherein an increase in activation of MrgprX2 or MrgprB2 relative to the activation of MrgprX2 or MrgprB2 in the absence of the candidate agonist determines that the candidate compound is an agonist.

Definitions

Unless defined otherwise, all technical and scientific terms used herein have the meaning commonly understood by a person skilled in the art to which this invention belongs. The following references provide one of skill with a general definition of many of the terms used in this invention: The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Antibodies and fragments thereof described herein include, but are not limited to, polyclonal, monoclonal, chimeric, dAb (domain antibody), single chain, Fab, Fab' and F(ab')2 fragments, Fv, scFvs. A fragment of an antibody possess the immunological activity of its respective antibody. In some embodiments, a fragment of an antibody contains 1500 or less, 1250 of less, 1000 or less, 900 or less, 800 or less, 700 or less, 600 or less, 500 or less, 400 or less, 300 or less, 200 or less amino acids. For example, a protein or peptide inhibitor contains 1500 or less, 1250 of less, 1000 or less, 900 or less, 800 or less, 700 or less, 600 or less, 500 or less, 400 or less, 300 or less, 200 or less, 100 or less, 80 or less, 70 or less, 60 or less, 50 or less, 40 or less, 30 or less, 25 or less, 20 or less, 10 or less amino acids. For example, a nucleic acid inhibitor of the invention contains 400 or less, 300 or less, 200 or less, 150 or less, 100 or less, 90 or less, 80 or less, 70 or less, 60 or less, 50 or less, 40 or less, 35 or less, 30 or less, 28 or less, 26 or less, 24 or less, 22 or less, 20 or less, 18 or less, 16 or less, 14 or less, 12 or less, 10 or less nucleotides.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally, the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Also provided are variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, $Fc_\varepsilon RI$.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (Ann. N.Y. Acad. Sci. USA 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist antibody" is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains.

Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, an scFv, or a T-cell receptor. Epitopic determinants consist of chemically active surface groupings of molecules such as amino acids or sugar side chains and have specific three dimensional structural characteristics, as well as specific charge characteristics. For example, antibodies may be raised against N-terminal or C-terminal peptides of a polypeptide, linear or non-linear peptide sequences of a protein, as well as epitopes that comprise amino acids of a first antigen and those of a second antigen. As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (Nature 361:186-87 (1993)). The ratio of $K_{off}/K_{on}$ enables the cancellation of all parameters not related to affinity, and is equal to the dissociation constant $K_d$. Davies et al. (1990) Annual Rev Biochem 59:439-473). An antibody of the present invention is said to specifically bind to an antigen or epitope described herein (e.g., a CTLA, PD1, PDL1, or other immune inhibitory protein and/or tumor antigen) when the equilibrium binding constant ($K_d$) is ≤1 µM, preferably ≤100 nM, more preferably ≤10 nM, more preferably ≤1 nM, and most preferably ≤100 pM to about 1 pM, as measured by assays such as radioligand binding assays or similar assays known to those skilled in the art.

The invention also comprises polypeptides and nucleic acid fragments, so long as they exhibit the desired biological activity (i.e., antagonize MrgprX2 or MrgprB2) of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic complementary DNA (cDNA), a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof.

The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20th edition, (ed. A. R. Gennaro), Mack Publishing Co., Easton, Pa., 2000.

By "secretagogue" is meant a substance that causes another substance to be secreted.

By "G protein-coupled receptors (GPCR)" is meant a protein receptor that senses molecules outside a cell and activates, inside the cell, signal transduction pathways and, ultimately, cellular responses. GPCRs are called seven-transmembrane receptors because they pass through the cell membrane seven times.

By "agonist" is meant a chemical that binds to a receptor and activates the receptor to produce a biological response. Whereas an agonist causes an action, an "antagonist" blocks the action of the agonist and an inverse agonist causes an action opposite to that of the agonist. As used herein, the terms "antagonist" and "inhibitor" are used interchangeably to refer to any molecule that counteracts or inhibits, decreases, or suppresses the biological activity of its target molecule. Suitable MrgprX2 or MrgprB2 antagonists include soluble receptors, peptide inhibitors, small molecule inhibitors, ligand fusions, and antibodies.

By "wild type" or "WT" is meant the phenotype of the typical form of a species as it occurs in nature. Alternately, the wild type is conceptualized as a product of the standard, "normal" allele at a locus, in contrast to that produced by a non-standard, "mutant" allele.

The term "pseudo-allergic" refers to a condition named for its similar presentation to a true allergy, though due to different causes. It may be due to alterations in the metabolism of histamine. "Pseudo-allergic" means an antibody IgE-independent allergy-like reaction. In other words, pseudo-allergic does not require IgE to induce an allergy-like reaction.

The term "administering," as used herein, refers to any mode of transferring, delivering, introducing, or transporting an MrgprB2 or MrgprX2 antagonist, for example, to a subject in need of reduced pseudo-allergic-type reaction severity. Such modes include, but are not limited to, oral, topical, intravenous, intraperitoneal, intramuscular, intradermal, intranasal, and subcutaneous administration.

By "MrgprB2 or MrgprX2 antagonist" is meant any small molecule, chemical compound, antibody, nucleic acid molecule, or polypeptide, or fragments thereof that is capable of blocking, preventing, lessening, and altering MrgprB2's or MrgprX2's ability to activate a signal transduction pathway.

By "alteration" is meant a change (increase or decrease) in the activity of polypeptide, e.g., MrgprB2 or MrgprX2, as detected by standard methods known in the art such as those described herein. As used herein, an alteration includes a 10% or more change in expression levels or activity of a gene or polypeptide, preferably a 25% change, more preferably a 40% change, and most preferably a 50% or greater change in activity of polypeptide.

As used herein an "alteration" also includes a 2-fold or more change in expression levels or activity of a gene or polypeptide, for example, 5-fold, 10-fold, 20-fold, 30-fold, 40-fold, 50-fold, 100-fold, 500-fold, 1000-fold or more.

By "ameliorate" is meant decrease, suppress, attenuate, diminish, arrest, or stabilize the development or progression of a disease such as, for example, a pseudo-allergic-type reaction.

By "amplify" is meant to increase the number of copies of a molecule. In one example, the polymerase chain reaction (PCR) is used to amplify nucleic acids.

By "binding" is meant having a physicochemical affinity for a molecule. Binding is measured by any of the methods of the invention, e.g., a drug/compound with a receptor expressed on a cell.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

"Detect" refers to identifying, either directly or indirectly, the presence, absence, or amount of MrgprB2 or MrgprX2 activation of a signal transduction pathway to be detected.

By "effective amount" is meant the amount required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "recombinant" is meant nucleic acid molecules formed by laboratory methods of genetic recombination (such as molecular cloning) to bring together genetic material from multiple sources, creating sequences that would not otherwise be found in biological organisms.

A "heterologous promoter" is a promoter which is different from the promoter to which a gene or nucleic acid sequence is operably linked in nature. The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. A "heterologous polynucleotide" or a "heterologous gene", as used herein, is one that originates from a source foreign to the particular host cell, or, if from the same source, is modified from its original form.

By "reduces" is meant a negative alteration of at least 10%, 25%, 50%, 75%, or 100%.

By "reference" is meant a standard or control condition.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 2A (Middle) shows representative imaging traces. Each color line represents an individual cell. Black lines in "anti-IgE" panels are average traces for each genotype. Note: [Ca2+]i traces are similar between WT and MUT groups. FIG. 2A (right) shows quantification of percentage of responding cells. Cells were identified as responding if the $[Ca^{2+}]i$ rose by at least 50% for at least 10 seconds, which clearly distinguishes a ligand-induced response from random flickering events. Group data for these and all other experiments are expressed as mean±standard error of the mean. One-tailed unpaired Student's t-test was used to determine significance in statistical comparisons, and differences were considered significant at $p<0.05$. , $p<0.01$ (n=3 for each genotype; over 150 cells counted for each condition). Anti-IgE responses were not significantly different. Scale bar is 10 µm. FIG. 2C (top) shows representative traces showing contractions of trachea isolated from WT and MrgprB2$^{MUT}$ mice (previously sensitized to ovalbumin (ova)), in response to 48/80 (30 µg/ml) or ova (10 µg/ml; i.e. IgE-dependent). FIG. 2C (bottom) shows the average data of maximum total contraction determined as response to 10 µM carbamycholine added at the end of the experiment. n=5 for 48/80 WT, 3 for 48/80 MrgprB2$^{MUT}$. FIG. 2D (right) shows quantification of Evans Blue leakage into the paw and paw thickness increase after 15 minutes. *, $p<0.02$ (n=5/WT, n=6/MrgprB2$^{MUT}$). Differences after saline injection were not significant.

FIG. 3A shows the percentage of responding cells from WT and MrgprB2$^{MUT}$ peritoneal mast cells after drug application, assayed using Fluo-4 imaging. Concentrations of drugs (in µg/ml): icatibant, 50; cetrorelix, 20; leuprolide, 100; octreotide, 10; sermorelin, 60; insulin, 80. n=3/genotype; >150 cells counted/substance, except >100 cells counted for insulin. Difference between insulin responsiveness was not significant. FIG. 3B (right) shows quantification of Evans Blue leakage into the paw after 15 minutes. **, $p<0.01$ (n=6 for each genotype). Difference after saline injection was not significant.

FIG. 4A is a series of structures of Compound 48/80 and a cyclized variant, which is reported to be more potent. The tetrahydroisoquinoline (THIQ) motif is highlighted in blue. FIG. 4C shows the percentage of responding cells from WT and MrgprB2$^{MUT}$ peritoneal mast cells after application of various NMBDs, assayed using Fluo-4 imaging. Concentrations of drugs (in µg/ml): atracurium, 50; mivacurium, 20; tubocurarine, 30; rocuronium, 500. n=3 mice/genotype; >150 cells counted/substance.

FIG. 5A shows results from a low-stringency RT-PCR screen in peritoneal mast cells for expression of the MrgprX1 orthologues MrgprA3 and MrgprC11. Arrow points to expected band sizes. FIG. 5C is a chart summarizing responses to MrgprX2 ligands and the MrgprX1 ligand chloroquine (CQ) by HEK293 cells transiently transfected with plasmids driving expression of MrgprX2, MrgprB2, and other mouse Mrgprs (i.e. MrgprB1, B10, and B11) most closely related to MrgprB2. Positive and negative responses are indicated as "checks" and "crosses", respectively. Responses were considered positive if at least half of the transfected cells showed a 50% increase in [Ca2+]i. No cells transfected with MrgprB1, B10, and B11 responded to any listed drug.

FIG. 6A shows example traces showing changes in [Ca2+]i, as measured by Fluo-4 imaging, from HEK293 cells expressing MrgprB2 and Gα15. FIG. 6C is a table of EC50s of basic secretagogues and drugs associated with pseudo-allergic reactions to activate MrgprB2 and MrgprX2-expressing HEK293 cells. The EC50s were determined from dose response studies which were repeated three times. Data are expressed as mean±SEM.

FIG. 7 shows representative confocal images from two other BAC transgenic mouse lines. BAC mice expressing eGFP-Cre in the MrgprB2 open reading frame were mated to tdTomato reporter mice and tdTomato (red) expression was compared to avidin staining (green), a marker for mast cells. Scale bar is 20 µm.

FIG. 8A shows representative images of a stomach section from an MrgprB2-tdTomato mouse stained with an anti-MCPT1 (β-chymase) antibody to label mucosal mast cells. White arrows indicate positive cells. No cells were double-labeled (296 Mcpt1-labeled cells and 275 tdTomato-positive cells counted, n=3 mice). Scale bar is 40 µm. FIG. 8B shows representative images of a Cytospin preparation of peripheral white blood cells from an MrgprB2-tdTomato mouse doubly labeled with tdTomato for MrgprB2-expressing cells (red; left image) and Hoechst 33342 nuclear staining (blue; right image). No peripheral white blood cell expressed MrgprB2 (n=3 mice; >4000 cells examined). Scale bar is 40 µm.

FIG. 9A, FIG. 9B, FIG. 9C, and FIG. 9D show that MrgprB2$^{MUT}$ mice are functional knockouts. FIG. 9A is an illustration of the genomic region in and around the MrgprB2 locus. Note that repetitive sequences including long interspersed elements (LINEs), short interspersed elements (SINEs), and long tandem repeats (LTRs) begin immediately after the 3' side of the MrgprB2 gene, and in addition are present within 2.5 kb of the 5' side. A BLASTN search in March 2014 using the 500 bases adjacent to the 3' end of MrgprB2 as a query turned up more than 269,000 hits in the mouse genome. FIG. 9B is a comparison of the WT and MUT genomic sequences that shows the location of the four base pair deletion in the mutant. Numbers correspond to the MrgprB2 open reading frame. FIG. 9C is a sequencing result from WT and MUT cDNA sampled from mice born 18 months after the mutant line was established. The bases missing in the mutant are highlighted in red. FIG. 9D is an amino acid translation of the MrgprB2$^{MUT}$ open reading frame that reveals that the deletion creates a frameshift mutation and an early termination codon (*) shortly after the first transmembrane region. Mut—site of the frameshift deletion. TM1—transmembrane region 1.

FIG. 10A (top) shows representative pictures of avidin staining in WT and MrgprB2$^{MUT}$ mice. Scale bar is 40 µm. FIG. 10A (bottom) shows quantification of mast cell numbers in various tissues. Differences are not significant, using a two-tailed unpaired Student's t test (n=3 mice for each genotype; over 3000 µm2 and 1000 µm2 counted for each genotype for hairy and glabrous skin, respectively; over 10,000 peritoneal cells counted). FIG. 10B shows that the tracheal histamine content averaged 5.9±0.9 and 5.5±1.6 ng/mg (n=5 for each genotype), respectively; the skin histamine content averaged 30.8±3.2 and 30.2±4.0 ng/mg (n=8 for each genotype), respectively. Differences were not significant. Group data are expressed as mean±standard error of the mean. Two-tailed unpaired Student's t test was used to determine significance in statistical comparisons.

FIG. 11A shows representative heat map images of mouse peritoneal mast cells showing changes in [Ca2+]i, as assayed by Fluo-4 imaging, induced by bath application of endothelin (1 µM). Scale bar is 10 µm. FIG. 11B shows averages of [Ca2+]i imaging traces for WT (red line) and MrgprB2$^{MUT}$ (black line). The [Ca2+]i traces are similar between WT and MUT groups. Traces were averaged as described for FIG. 2A. FIG. 11C shows quantification of percentage of responding cells. Group data are expressed as mean±standard error of the mean. Two-tailed unpaired Student's t test was used to determine significance in statistical comparisons (n=3 for each genotype; over 180 cells counted for each genotype). Endothelin-induced responses were not significantly different.

FIG. 12A and FIG. 12B show that IgE-mediated inflammation does not differ between wild type and MrgprB2$^{MUT}$ mice. FIG. 12A shows representative images of Evans Blue extravasation 15 minutes after intraplantar injection of anti-IgE antibody (right, arrow, 100 µg/ml, 7 µl in saline) or saline (left). FIG. 12B shows quantification of Evans Blue leakage into the paw after 15 minutes (n=6 for WT, n=7 for MrgprB2$^{MUT}$). Differences after anti-IgE antibody (p=0.49) and saline (p=0.23) injection are not significant. Group data are expressed as mean±standard error of the mean. Two-tailed unpaired Student's t test was used to determine significance in statistical comparisons.

FIG. 13A shows example traces showing changes in [Ca2+]i, as measured by Fluo-4 imaging, from WT and MrgprB2$^{MUT}$ peritoneal mast cells induced by the basic secretagogues from FIG. 2E. Each trace is a response from a unique cell. FIG. 13B shows representative Fluo-4 images (left) and fluorescence traces (right) from WT (top) and MrgprB2$^{MUT}$ (bottom) cultured peritoneal mast cells during application of icatibant (50 µg/ml). FIG. 9C shows example traces showing changes in [Ca2+]i, as measured by Fluo-4 imaging, from WT and MrgprB2$^{MUT}$ peritoneal mast cells induced by selected FDA-approved cationic peptidergic drugs. Each trace is a response from a unique cell. FIG. 13D is a series of photomicrographs and a line graph showing representative Fluo-4 images (left) and fluorescence traces (right) from WT (top) and MrgprB2$^{MUT}$ (bottom) cultured peritoneal mast cells during application of atracurium (50 µg/ml). FIG. 13E is a series of photomicrographs and a line graph showing representative Fluo-4 images (left) and fluorescence traces (right) from WT (top) and MrgprB2$^{MUT}$ (bottom) cultured peritoneal mast cells during application of ciprofloxacin (200 µg/ml).

FIG. 14B shows that knockdown of human MrgprX2 significantly reduced mast cell activation evoked by basic secretagogues and drugs associated with pseudo-allergic reactions, but not by IgE. Human LAD2 mast cells were first transfected with MrgprX2 siRNA or control siRNA. Two days after the transfection, the cells were treated with compound 48/80 (0.1 µg/ml), mastoparan (5 µg/ml), icatibant (10 µg/ml), atracurium (25 µg/ml), and ciprofloxacin (75 µg/ml). The activation of mast cells in response to these substances characterized by the release of 3-hexosaminidase was significantly reduced in MrgprX2 siRNA treated cells, compared to release in the control group. IgE-mediated mast cell degranulation was unaffected by MrgprX2 siRNA knockdown. Group data are expressed as mean±standard error of the mean. Two-tailed unpaired Student's t test was used to determine significance in statistical comparisons, and differences were considered significant at *$p<0.05$; $p<0.01$; *$p<0.005$ (the experiments were repeated three times).

FIG. 15 is a table of all FDA-approved therapeutic drugs under 50 amino acids. Charges calculated by ChemAxon. ISR data for cetrorelix, ganirelix, and octreotide are from the following references: Verschraegen, C. F. et al. Gynecologic oncology 90, 552-559 (2003); Fluker, M. et al. Fertility and sterility 75, 38-45 (2001); and Tuvia, S. et al. The Journal of clinical endocrinology and metabolism 97, 2362-2369, (2012), incorporated herein by reference. All other information was supplied by the FDA.

FIG. 16 is a chart listing all classes of FDA-approved neuromuscular blocking drugs (NMBDs), and representative members.

DETAILED DESCRIPTION OF THE INVENTION

Figure 1A:
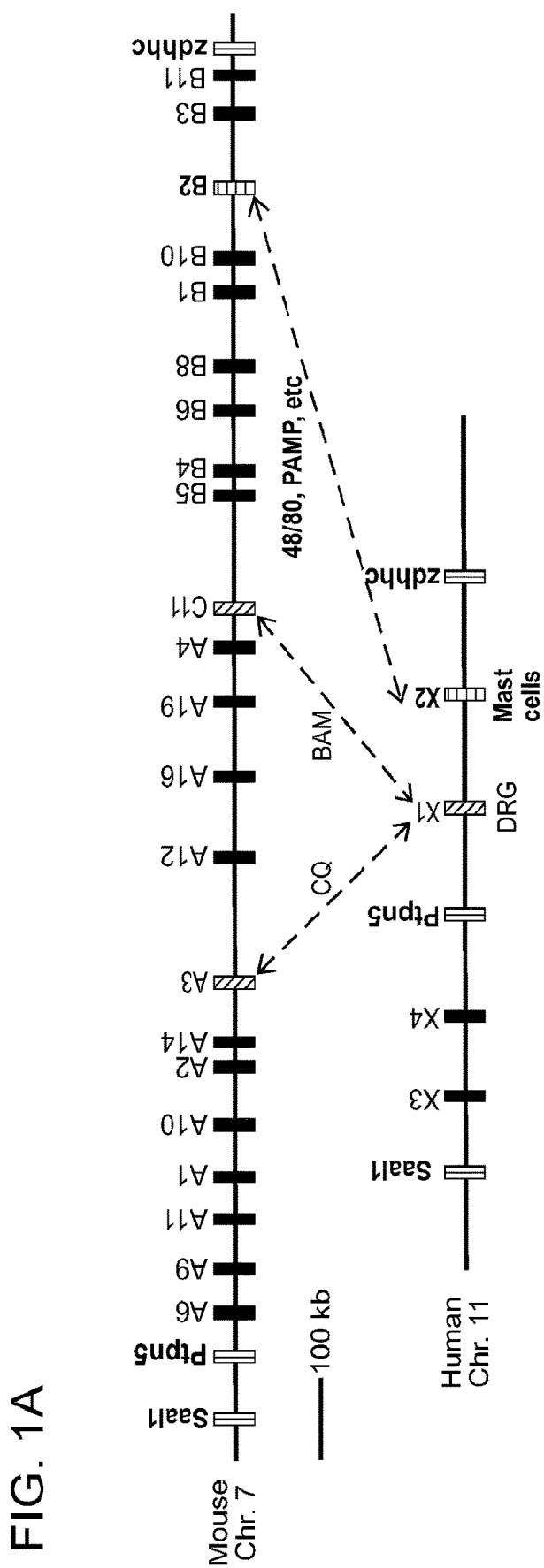
FIG. 1A is diagram of the mouse and human Mrgpr genomic loci, illustrating the expanded gene family in mice and their identified human orthologues based on similar expression patterns and agonist specificity. The mouse Mrgpr genes (shown as vertical bars with names on top) are clustered on chromosome 7. Mouse MrgprA3 (A3) and MrgprC11 (C11) are the orthologues of human MrgprX1 (X1) and are expressed specifically in dorsal root ganglion (DRG) neurons, and function as itch receptors mediating chloroquine (CQ) and BAMS-22 (BAM) induced itch. The expression and agonist specificity of mouse MrgprB2 (B2), the orthologue of human MrgprX2 (X2), are described below.

The invention features cells and methods for determining whether a compound induces a pseudo-allergic-type reaction and methods for reducing the severity of a pseudo-allergic-type reaction in a subject. The present invention is based, at least in part, on the discovery of a G protein coupled receptor, i.e., MrgprB2 in mice and MrgprX2 in humans, exclusively expressed in a type of immune cell called the mast cell, which is linked closely to allergic-type reactions to foreign substances. The inventors determined that this single receptor is activated by at least 13 different FDA-approved drugs associated with allergic-type reactions as part of their side effect profiles.

Prior to the invention described herein, the role of MrgprX2/MrgprB2 in pseudo-allergic drug reactions was completely unknown. Described herein is the use of MrgprX2/MrgprB2 expressing cell-based assays to screen for drugs that induce pseudo-allergic drug reactions, and to screen for antagonists of MrgprX2 that block these reactions. In order to make the assay work, the inventors added the GTP-binding protein alpha 15 (Gα15) in MrgprX2/MrgprB2 expressing cells to convert receptor-based signals to increases in intracellular calcium, making the cell lines compatible with high-throughput screening devices. MrgprX2/MrgprB2's role in pseudo-allergic drug reactions was unknown prior to the present invention. Accordingly, it is not surprising that MrgprX2/Gα15 cells have not been reported. While Gα15 expression in other isolated cell lines has been reported, it only is utilized when the receptor does not induce a rise in intracellular calcium. MrgprX2 induces such a rise which would suggest that including Gα15 in an isolated cell as unnecessary. However, inventors found that MrgprX2 normally induces such a rise in response to some agonists but not others, making co-expression essential for the assay to work.

The isolated cells of the present invention express the human G-protein coupled receptor (GPCR) MrgprX2 or the mouse GPCR MrgprB2, along with expression of the GTP-binding protein Gα15, which allows easy visualization of receptor activation in a calcium-based screening assay. These cell lines permit the screening of FDA-approved drugs and drugs in development for MrgprX2 agonist and antagonist activity. This is desirable because off-target activation of MrgprX2 induces allergic-type side effects in the body that can result in significant adverse events.

Using these cells in a cell-based assay for drug screens, a positive result (i.e., activation of the cell line as measured by, e.g., calcium release) would indicate that the drug would normally activate mast cells and potentially cause an allergic-type reaction in a patient. Screens of drugs in development would predict their side effect profile; screens of drugs currently in use would identify a cause of the adverse effects of these drugs; screens of antagonists would lead to new therapeutic drugs that can be provided at the same time as drugs that induce allergic-type reactions, thus blocking activation of mast cells while not interfering with their intended uses.

As described in detail below, local and systemic allergic-type responses in wild-type mice in response to these drugs are abolished in mice that lack MrgprB2, the mouse orthologue of human MrgprX2. This highly unexpected finding demonstrates that MrgprX2 is an attractive drug target, since an antagonist can be co-applied with a very wide range of drugs to block their allergic-type side effects.

Described herein are cell lines that are used to screen for FDA-approved drugs and investigational compounds that activate or antagonize this receptor. These will be useful to determine whether a drug will induce allergic-type responses, and in screens to develop antagonists that block these responses.

Described herein are results demonstrating that basic secretagogues activate mouse mast cells in vitro and in vivo through a single receptor, MrgprB2, the orthologue of the human G-protein coupled receptor (GPCR) MrgprX2. Secretagogue-induced histamine release, inflammation, and airway contraction are abolished in MrgprB2 null mutant mice. Further, as described in detail below, most classes of FDA-approved peptidergic drugs associated with allergic-type injection-site reactions also activate MrgprB2 and MrgprX2, and that injection-site inflammation is absent in mutant mice. The results described herein demonstrate that MrgprB2 and MrgprX2 are targets of many small molecule drugs associated with systemic pseudo-allergic, or anaphylactoid, reactions; that drug-induced symptoms of anaphylactoid responses are significantly reduced in knockout mice. Also described herein is the identification of a common chemical motif in several of these molecules that helps predict side effects of other compounds. Described in detail below is the introduction of a mouse model to study mast cell activation by basic secretagogues and identification of MrgprX2 as a therapeutic target to reduce a subset of drug-induced adverse effects.

Mast Cells

Mast cells are primary effectors in allergic reactions, and may have significant roles in diseases by secreting histamine and various inflammatory and immunomodulatory substances (Metcalfe, et al., 1997 *Physiological reviews* 77, 1033-1079; Galli et al., 2005 *Nature immunology* 6, 135-142). While classically they are activated by IgE antibodies, a unique property of mast cells is their antibody-independent responsiveness to a range of cationic substances, collectively called basic secretagogues, including inflammatory peptides and drugs associated with allergic-type reactions (Metcalfe, et al., 1997 *Physiological reviews* 77, 1033-1079; Lagunoff et al., 1983 *Annual review of pharmacology and toxicology* 23, 331-351). Roles for these substances in pathology have prompted a decades-long search for their receptor(s).

A mast cell (also known as a mastocyte or a labrocyte) is derived from the myeloid stem cell. It is a part of the immune system and contains many granules rich in histamine and heparin. Although best known for their role in allergy and anaphylaxis, mast cells play an important protective role as well, being intimately involved in wound healing, including angiogenesis, and defense against pathogens. The mast cell is very similar in both appearance and function to the basophil, another type of white blood cell. These cells differ in that mast cells are tissue resident, e.g., in mucosal tissues, while basophils are found in the blood. Both cells are granulated cells that contain histamine and heparin, an anticoagulant. Both cells also release histamine upon binding to immunoglobulin E.

Mast cells are present in most tissues characteristically surrounding blood vessels and nerves, and are especially prominent near the boundaries between the outside world and the internal milieu, such as the skin, mucosa of the lungs, and digestive tract, as well as the mouth, conjunctiva, and nose.

Mast cells play a key role in the inflammatory process. When activated, a mast cell rapidly releases its characteristic granules and various hormonal mediators into the interstitium. Mast cells can be stimulated to degranulate by direct injury (e.g., physical or chemical (such as opioids, alcohols, and certain antibiotics such as polymyxins]), cross-linking of immunoglobulin E (IgE) receptors, or complement proteins.

Mast cells express a high-affinity receptor (FcεRI) for the Fc region of IgE, the least-abundant member of the antibodies. This receptor is of such high affinity that binding of IgE molecules is in essence irreversible. As a result, mast cells are coated with IgE, which is produced by plasma cells (the antibody-producing cells of the immune system).

In allergic reactions, mast cells remain inactive until an allergen binds to IgE already coated upon the cell. Other membrane activation events can either prime mast cells for subsequent degranulation or act in synergy with FcεRI signal transduction. In general, allergens are proteins or polysaccharides. The allergen binds to the antigen-binding sites, which are situated on the variable regions of the IgE molecules bound to the mast cell surface. The clustering of the intracellular domains of the cell-bound Fc receptors, which are associated with the cross-linked IgE molecules, causes a complex sequence of reactions inside the mast cell that lead to its activation. The molecules released into the extracellular environment include: preformed mediators (from the granules) (e.g., serine proteases, such as tryptase, histamine (2-5 pg/cell), serotonin, proteoglycans, heparin (active as anticoagulant)), newly formed lipid mediators (eicosanoids) (i.e., thromboxane, prostaglandin D2, leukotriene C4, platelet-activating factor), and cytokines (e.g., eosinophil chemotactic factor).

Histamine dilates post-capillary venules, activates the endothelium, and increases blood vessel permeability. This leads to local edema (swelling), warmth, redness, and the attraction of other inflammatory cells to the site of release. Histamine also depolarizes nerve endings (leading to itching or pain). Cutaneous signs of histamine release include the "flare and wheal"-reaction. The bump and redness immediately following a mosquito bite are a good example of this reaction, which occurs seconds after challenge of the mast cell by an allergen.

MrgprX2

As described herein, mas-related G-protein coupled receptor member X2 (MrgprX2) is a mast cell-specific receptor for basic secretagogues, i.e., cationic amphiphilic drugs, as well as endo- or exogenous peptides, consisting of a basic head group and a hydrophobic core. See, McNeil B. D., 2015 Nature, 519: 237-241, incorporated herein by reference. As described in detail below, MrgprX2 recognizes and binds small molecules containing a cyclized tetrahydroisoquinoline (THIQ), such as non-steroidal neuromuscular blocking drugs (NMBDs), including tubocurarine and atracurium. As described in detail below, in response to these compounds, MrgprX2 mediates pseudo-allergic reactions characterized by histamine release, inflammation and airway contraction. As described herein, MrgprX2 also acts as a receptor for a number of other ligands, including peptides and alkaloids, such as cortistatin-14, proadrenomedullin N-terminal peptides PAMP-12 and, at lower extent, PAMP-20, antibacterial protein LL-37, PMX-53 peptide, beta-defensins, and complanadine A.

An exemplary human MrgprX2 amino acid sequence is provided below (NP_001290544.1 (GI:746816153), incorporated herein by reference (SEQ ID NO: 1)):

```
 1  mdpttpawgt esttvngndq allllcgket lipvflilfi alvglvgngf vlwllgfrmr
61  rnafsvyvls lagadflflc fqiinclvyl snffcsisin fpsffttvmt caylaglsml
```

-continued

```
121 stvstercls vlwpiwyrcr rprhlsavvc vllwalslll silegkfcgf lfsdgdsgwc
181 qtfdfitaaw liflfmvlcg sslallvril cgsrglpltr lyltilltvl vfllcglpfg
241 iqwflilwiw kdsdvlfchi hpvsvvlssl nssanpiiyf fvgsfrkqwr lqqpilklal
301 qralqdiaev dhsegcfrqg tpemsrsslv
```

An exemplary human MrgprX2 nucleic acid sequence is provided below (NM_001303615.1 (GI:746816152), incorporated herein by reference (SEQ ID NO: 2)):

```
   1 tggctacagg aaagggccac caggcagggc tatgtcctta ggtagaaaaa cactgccact
  61 gccaactcac agcccttcag ggcgcaggga gagagccagg aaattttaa aaaatcatcc
 121 cccaatctac tgtcaatgtg tccctttggc tgaaaaaaaa agtcaccctc caatctcctg
 181 tcaatgtgta ccctttggag cctgagtgaa agacagccca ttgacgaggc acagacatgt
 241 ctcctcccag gatgcaaagt gtcacttctt tggactagtc tctcactatc atcataaatg
 301 ccttgagaat ggaatgtggt tgggaaaaaa agggattggg agtacatagg tactcccagc
 361 tataagtaca caggggcacc agtggaggtt ttctgagcat ggatccaacc accccggcct
 421 ggggaacaga aagtacaaca gtgaatggaa atgaccaagc ccttcttctg ctttgtggca
 481 aggagaccct gatcccggtc ttcctgatcc ttttcattgc cctggtcggg ctggtaggaa
 541 acgggtttgt gctctggctc ctgggcttcc gcatgcgcag gaacgccttc tctgtctacg
 601 tcctcagcct ggccggggcc gacttcctct cctctgctt ccagattata aattgcctgg
 661 tgtacctcag taacttcttc tgttccatct ccatcaattt ccctagcttc ttcaccactg
 721 tgatgacctg tgcctacctt gcaggcctga gcatgctgag caccgtcagc accgagcgct
 781 gcctgtccgt cctgtggccc atctggtatc gctgccgccg ccccagacac ctgtcagcgg
 841 tcgtgtgtgt cctgctctgg gccctgtccc tactgctgag catcttggaa gggaagttct
 901 gtggcttctt atttagtgat ggtgactctg gttggtgtca gacatttgat ttcatcactg
 961 cagcgtggct gatttttttta ttcatggttc tctgtgggtc cagtctggcc ctgctggtca
1021 ggatcctctg tggctccagg ggtctgccac tgaccaggct gtacctgacc atcctgctca
1081 cagtgctggt gttcctcctc tgcggcctgc cctttggcat tcagtggttc ctaatattat
1141 ggatctggaa ggattctgat gtcttatttt gtcatattca tccagtttca gttgtcctgt
1201 catctcttaa cagcagtgcc aaccccatca tttacttctt cgtgggctct tttaggaagc
1261 agtggcggct gcagcagccg atcctcaagc tggctctcca gagggctctg caggacattg
1321 ctgaggtgga tcacagtgaa ggatgcttcc gtcagggcac cccggagatg tcgagaagca
1381 gtctggtgta gagatggaca gcctctactt ccatcagata tatgtggctt tgagaggcaa
1441 ctttgcccct gtctgtctga tttgctgaac tttctcagtc ctgattttaa aacagttaag
1501 agagtccttg tgaggattaa gtgagacagt gcctatgaaa caaacactaa gtgcagtgtc
1561 tctggaactg ccttactcac aggcttccac cacagcccta tgagagcttt gccaactctg
1621 cggtccatga ctgttcccac ttttaatgaa tcctacccttt cgcagaaggc tgaaagcagg
1681 gcagaaaaga tctacatttc tttggacact gcacttgata gggactcaaa gaatgttata
1741 ttttttaatta atttcttttt ctcttccgta caatttctgt ctcaacaaaa ttagaagaat
1801 taaatttaaa actagctcca aaagagcagt cgtctttcat tttggcagac cttagaatat
1861 cccctagct taataaatct tgttgaatg gcttaatgaa tgaataaact ggttaatgtt
1921 taagttaaac ctctgaaaag tctccattta ccagatttga gtcactaaat ttattgcttt
```

-continued

```
1981  cactactttt gaattttgca aacatgaaat taagttttat aattagataa atcaatgtca
2041  acacatattt aaagtttgag gtacactgtc ttcctgtggt ttcctttcac atgccatccc
2101  ttaaaatccc agctacacgc cttcccattc cttcccttt gcctttgttc taatcttccc
2161  tctctggggg ctctctaatt cgtcctggaa gtttccagtg gtcttataga ctccatgttc
2221  ttggaggaca ggctgtatgt cagatttacc ttttattccg aagaactcgg agcatttatt
2281  ttgttaatta aattgcacat atttttaaaa gttacgtgtt ccacagaata aaatactaat
2341  tgtaaaaaaa aaaaaaaaaa aaaaaaaaaa aaaaaaaaaa aaaaaaaaaa aaaaaaaaaa
2401  aaaaaaaaaa aaaaaaaaaa aaaaaaaaaa aaaaaaaaaa
```

An exemplary mouse MrgprB2 amino acid sequence is provided below (NP_780740.2 (GI:229094244), incorporated herein by reference (SEQ ID NO: 3)):

```
  1 msgdfliknl stsawktnit vlngsyyidt svcvtrnqam illsiiislv gmglnaivlw
 61 flgirmhtna ftvyilnlam adflylcsqf viclliafyi fysidinipl vlyvvpifay
121 lsglsilsti sierclsviw piwyrckrpr htsaitcfvl wvmslllgll egkacgllfn
181 sfdsywcetf dvitniwsvv ffgvlcgssl tllvrifcgs qripmtrlyv titltvlvfl
241 ifglpfgiyw ilyqwisnfy yveicnfyle ilflscvnsc mnpiiyflvg sirhrrfrrk
301 tlklllqram qdtpeeeqsg nksssehpee letvqscs
```

An exemplary mouse MrgprB2 nucleic acid sequence is provided below (NM_175531.4 (GI:229094243), incorporated herein by reference (SEQ ID NO: 4)):

```
   1 agaggactct tctctttgtc acagaccagt ttaacacttc ccataagaag aatagagcaa
  61 aggaacatga gtggagattt cctaatcaag aatctaagca cctcagcctg gaaaacgaac
 121 atcacagtgc tgaatggaag ctactacatc gatacttcag tttgtgtcac caggaaccaa
 181 gccatgattt tgctttccat catcatttcc ctggttggga tgggactaaa tgccatagtg
 241 ctgtggttcc tgggcatccg tatgcacacg aatgccttca ctgtctacat tctcaacctg
 301 gctatggctg actttctta cctgtgctct cagtttgtaa tttgtcttct tattgccttt
 361 tatatcttct actcaattga catcaacatc cctttggttc tttatgttgt gccaatattt
 421 gcttatcttt caggtctgag cattctcagc accattagca ttgagcgctg cttgtctgta
 481 atatggccca tttggtatcg ctgtaaacgt ccaagacaca atcagctat cacatgtttt
 541 gtgctttggg ttatgtcctt attgttgggt ctcctggaag ggaaggcatg tggcttactg
 601 tttaatagct ttgactctta ttggtgtgaa acatttgatg ttatcactaa tatatggtca
 661 gttgtttttt ttggtgttct ctgtgggtct agcctcaccc tgcttgtcag gatcttctgt
 721 ggctcacagc gaattcctat gaccaggctg tatgtgacta ttacactcac agtcttggtc
 781 ttcctgatct ttggtcttcc ctttgggatc tattggatac tctatcagtg gattagcaat
 841 ttttattatg ttgaaatttg taattttat cttgagatac tattcctatc ctgtgttaac
 901 agctgtatga accccatcat ttatttcctt gttggctcca ttaggcaccg aaggttcagg
 961 cggaagactc tcaagctact tctgcagaga gccatgcaag acacccctga ggaggaacaa
1021 agtggaaata agagttcttc agaacaccct gaagaactgg aaactgttca gagctgcagc
1081 tgacaactgc ttgatcagac aaaaatggtt ttgatggaaa tacttttct tatccgtgtg
1141 gaccattttt acaaccttta ttcagtttgt tatctcatct tcaattgttt aattaggaca
```

-continued

```
1201  ataatttttg taaaagttga gagaaatggg tcttgtcata ctaatactga atgtagcatt
1261  tctgaagctg tgttacttag ggatttacca tctccttttc atgggactcc ttgtaagtat
1321  tctgtggtag agaacttctc ctattgttga caaactctcc tttagaaggc aaatggaaat
1381  acaaggaagg gctgtatttc tttacccact gaaatgtata atgagtacac aaatgttaca
1441  tctagcaaat attcttttag aacacccttc tcaatgttta agacttaaat agaaacactt
1501  tataatccta gtccttatta atttcttcag gttataaaga atatatgaag tgatagtttt
1561  tttacgtaaa ttttttacta aacaaataaa atttctcaaa agaagactgt taaatctctc
1621  ttaacccagc tgagtcctca ctgtgaacat caagttcact gtgtctctaa ttttaaaat
1681  ttgaagagtg cacttagatt tggcaatgag atccatcaaa atccatgtcc acatgaaggt
1741  gaagagagtc agacttctgt gtttctcttc acaatgcctt ctttagcatt ccatggtcga
1801  gtgttttccc tttactccct gcctttgctg tgatttctgc tctctctgac tgtctaattc
1861  ttcatgagaa gtttccacta ggtcctctag acaatcctgt ctcaaattta aatcaccctc
1921  agataattta ttatgtgaat ttgttacttg cattgataac aatcattgta attgaatatg
1981  aatattttt gtaacacttt ctataaaata atatttgttt taagctgta ctatgtgata
2041  ttttcagttg aagcataatt aaaagagttc aaccaaaaaa aaaaaaaaa
```

Gα15

GTP-binding protein alpha 15 (Gα15) is a modulator or transducer in various transmembrane signaling systems.

An exemplary human Gα15 amino acid sequence is provided below (NP_002059.3 (GI:597709771), incorporated herein by reference (SEQ ID NO: 5)):

```
  1  marsltwrcc pwcltedeka aarvdqeinr illeqkkqdr gelklllllgp gesgkstfik
 61  qmriihgagy seeerkgfrp lvyqnifvsm ramieamerl qipfsrpesk hhaslvmsqd
121  pykvttfekr yaaamqwlwr dagiracyer rrefhlldsa vyylshleri teegyvptaq
181  dvlrsrmptt gineycfsvq ktnlrivdvg gqkserkkwi hcfenviali ylaslseydq
241  cleennqenr mkeslalfgt ilelpwfkst svilflnktd ileekiptsh latyfpsfqg
301  pkqdaeaakr fildmytrmy tgcvdgpegs kkgarsrrlf shytcatdtq nirkvfkdvr
361  dsvlarylde inll
```

An exemplary human Gα15 nucleic acid sequence is provided below (NM_002068.3 (GI:597709770), incorporated herein by reference (SEQ ID NO: 6)):

```
  1  cagaaggagg aagaagggcc ctgctggtca cacaggaccc agtctgcggt gggggttttc
 61  ccgccaccgc cccgccctcc ctggggcccc cacctcaccc tctcctggca ccttcaccg
121  tcaacctgtc gggccgggtc tgagcaggtc tggaggtggg cggggagccc tggcctcccc
181  acctcctccc gtccccaccc tgttcccagc actcaagcct tgccaccgcc gagccgggct
241  tcctgggtgt ttcaggcaag gaagtctagg tccctggggg gtgacccccca aggaaaaggc
301  agcctccctg cgcacccggt gcccggagc cctctccagg gccggctggg ctgggggttg
361  ccctggccag caggggcccg ggggcgatgc caccggtgc cgactgaggc caccgcacca
421  tggcccgctc gctgacctgg cgctgctgcc cctggtgcct gacggaggat gagaaggccg
481  ccgccgggt ggaccaggag atcaacagga tcctcttgga gcagaagaag caggaccgcg
541  gggagctgaa gctgctgctt ttgggcccag gcgagagcgg gaagagcacc ttcatcaagc
```

-continued

```
 601 agatgcggat catccacggc gccggctact cggaggagga gcgcaagggc ttccggcccc
 661 tggtctacca gaacatcttc gtgtccatgc gggccatgat cgaggccatg gagcggctgc
 721 agattccatt cagcaggccc gagagcaagc accacgctag cctggtcatg agccaggacc
 781 cctataaagt gaccacgttt gagaagcgct acgctgcggc catgcagtgg ctgtggaggg
 841 atgccggcat ccgggcctgc tatgagcgtc ggcgggaatt ccacctgctc gattcagccg
 901 tgtactacct gtcccacctg agcgcatca ccgaggaggg ctacgtcccc acagctcagg
 961 acgtgctccg cagccgcatg cccaccactg gcatcaacga gtactgcttc tccgtgcaga
1021 aaaccaacct gcggatcgtg gacgtcgggg gccagaagtc agagcgtaag aaatggatcc
1081 attgtttcga gaacgtgatc gccctcatct acctggcctc actgagtgaa tacgaccagt
1141 gcctggagga gaacaaccag gagaaccgca tgaaggagag cctcgcattg tttgggacta
1201 tcctggaact accctggttc aaaagcacat ccgtcatcct ctttctcaac aaaaccgaca
1261 tcctggagga gaaaatcccc acctcccacc tggctaccta tttccccagt ttccagggcc
1321 ctaagcagga tgctgaggca gccaagaggt tcatcctgga catgtacacg aggatgtaca
1381 ccgggtgcgt ggacggcccc gagggcagca agaagggcgc acgatcccga cgcctcttca
1441 gccactacac atgtgccaca gacacacaga acatccgcaa ggtcttcaag gacgtgcggg
1501 actcggtgct cgcccgctac ctggacgaga tcaacctgct gtgacccagg ccccacctgg
1561 ggcaggcggc accggcgggc gggtgggagg tgggagtggc tgcagggacc cctagtgtcc
1621 ctggtctatc tctccagcct cggcccacac gcaagggagt cgggggacgg acggcccgct
1681 gctggccgct ctcttctctg cctctcacca ggacagccgc ccccagggt actcctgccc
1741 ttgcttgact cagtttccct cctttgaaag ggaaggagca aaacggccat ttgggatgcc
1801 agggtggatg aaaaggtgaa gaaatcaggg gattgaggac ttgggtgggt gggcatctct
1861 caggagcccc atctccgggc gtgtcacctc ctgggcaggg ttctgggacc ctctgtgggt
1921 gacgcacacc ctgggatggg gctagtagag ccttcaggcg ccttcgggcg tggactctgg
1981 cgcactctag tggacaggag aaggaacgcc ttccaggaac ctgtggacta ggggtgcagg
2041 gacttccctt tgcaaggggt aacagaccgc tggaaaacac tgtcactttc agagctcggt
2101 ggctcacagc gtgtcctgcc ccggtttgcg gacgagaaa atcgcggccc acaagcatcc
2161 ccccatccct tgcaggctgg gggctgggca tgctgcatct taaccttttg tatttattcc
2221 ctcaccttct gcagggctcc gtgcgggctg aaattaaaga tttcttagag gctgcgtcgc
2281 cagcgtcctg tttaaaaaaa aaaaaaaaa a
```

An exemplary mouse Gα15 amino acid sequence is provided below (NP_034434.1 (GI:6754010), incorporated herein by reference (SEQ ID NO: 7)):

An exemplary mouse Gα15 amino acid sequence is provided below (NM_010304.3 (GI:34328487), incorporated herein by reference (SEQ ID NO: 8)):

```
  1 marsltwgcc pwclteeekt aaridqeinr illeqkkqer eelklllllgp gesgkstfik
 61 qmriihgvgy seedrrafrl liyqnifvsm qamidamdrl qipfsrpdsk qhaslvmtqd
121 pykvstfekp yavamqylwr dagiracyer rrefhlldsa vyylshleri sedsyiptaq
181 dvlrsrmptt gineycfsvk ktklrivdvg gqrserrkwi hcfenviali ylaslseydq
241 cleendqenr meeslalfst ilelpwfkst svilflnktd iledkihtsh latyfpsfqg
301 prrdaeaaks fildmyarvy ascaepqdgg rkgsrarrff ahftcatdtq svrsvfkdvr
361 dsvlarylde inll
```

```
   1  gctggagctt ccaccaccga cctgtctggc gggcagggcc aggtctgggc aagttggagg
  61  gggcgggaag cagcacccag gtccccgccc tgtttccagc acccaggcct cttgaagccc
 121  ttgcctgggc tcccacaggc cctaggcagg gacacggagg gccctggggt gacctccacc
 181  cccacctcca ctccatccgg agaagaaaga gtcccacagt tgggctctgc aggccctgtg
 241  atgtcacctg gtggtctgtg aagcgcccac catggcccgg tccctgactt ggggctgctg
 301  tccctggtgc ctgacagagg aggagaagac tgccgccaga atcgaccagg agatcaacag
 361  gattttgttg gaacagaaaa aacaagagcg cgaggaattg aaactcctgc tgttggggcc
 421  tggtgagagc gggaagagta cgttcatcaa gcagatgcgc atcattcacg gtgtgggcta
 481  ctcggaggag gaccgcagag ccttccggct gctcatctac cagaacatct tcgtctccat
 541  gcaggccatg atagatgcga tggaccggct gcagatcccc ttcagcaggc ctgacagcaa
 601  gcagcacgcc agcctagtga tgacccagga cccctataaa gtgagcacat tcgagaagcc
 661  atatgcagtg gccatgcagt acctgtggcg ggacgcgggc atccgtgcat gctacgagcg
 721  aaggcgtgaa ttccaccttc tggactccgc ggtgtattac ctgtcacacc tggagcgcat
 781  atcagaggac agctacatcc ccactgcgca agacgtgctg cgcagtcgca tgcccaccac
 841  aggcatcaat gagtactgct tctccgtgaa gaaaaccaaa ctgcgcatcg tggatgttgg
 901  tggccagagg tcagagcgta ggaaatggat tcactgtttc gagaacgtga ttgccctcat
 961  ctacctggcc tccctgagcg agtatgacca gtgcctagag gagaacgatc aggagaaccg
1021  catggaggag agtctcgctc tgttcagcac gatcctgagg ctgccctggt tcaagagcac
1081  ctcggtcatc ctcttcctca acaagacgga catcctggaa gataagattc acacctccca
1141  cctggccaca tacttcccca gcttccaggg accccggcga gacgcagagg ccgccaagag
1201  cttcatcttg gacatgtatg cgcgcgtgta cgcgagctgc gcagagcccc aggacggtgg
1261  caggaaaggc tcccgcgcgc gccgcttctt cgcacacttc acctgtgcca cggacacgca
1321  aagcgtccgc agcgtgttca aggacgtgcg ggactcggtg ctggcccggt acctggacga
1381  gatcaacctg ctgtgacgcg ggacagggaa ccccaagcgc gacgcggtcg tggcgaggac
1441  atacctcccc ctggtggccg cgcgtggaac tgcaggtcca ggagctgcca agtggggaag
1501  ccagcccaca gggagagagt ccctgcttcc tactgggccc caagcccag ctcccctgta
1561  atttattccc tcgcccttct tctagttgtt ggagaaagga catgagccgg gtctttaacc
1621  ccagcgctcc ggaggcagag gcaggaggat ttctgtgagt tccaggacca tgttttcaaa
1681  aacaaacaaa accggataga actgtccggg accttgtgac ttcccagggg ccctgttcac
1741  atcttcctgt ggggaccatt tcatcttacc aaaggggaaa ccgaggtcgg caagatggct
1801  ggtgagagtg ccttgccacc aagcctgaca actggacttc aggacctgtt cagtggacag
1861  agagagggag cggagtccta ggagaagttc tctatctcct caggcgtgca tggtggtgac
1921  acacctaccc acacagataa ataaatgtaa tttaaaaaca aaaaaaaaa aaaa
```

HEK293 Cells

Human embryonic kidney 293 cells, also often referred to as HEK 293, HEK-293, 293 cells, or less precisely as HEK cells, are a specific cell line originally derived from human embryonic kidney cells (from an aborted human embryo) grown in tissue culture and from still born animals. HEK 293 cells are very easy to grow and transfect very readily and have been widely used in cell biology research for many years. They are also used by the biotechnology industry to produce therapeutic proteins and viruses for gene therapy.

Described herein are HEK293 cells stably expressing Gα15 and either MrgprB2 or MrgprX2.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Materials and Methods

The following materials and methods were used.

Animal Models

All experiments involving equal treatments in WT and mutant samples and animals were conducted by experimenters blind to conditions.

Analysis

Group data were expressed as mean±standard error of the mean. Two-tailed unpaired Student's t test was used to determine significance in statistical comparisons, and differences were considered significant at $p<0.05$. Statistical power analysis was used to justify the sample size. It was assumed that the data were normally distributed since the most outcome values were symmetrically distributed around the mean value within each group. The variance is similar between groups determined by the F test. Mast cells deemed to be damaged, either by visible lack of fibronectin adherence or by abnormally high resting calcium levels, were excluded from analysis. Otherwise, no samples or animals subjected to successful procedures and/or treatments were excluded from the analysis. No randomization was used for animal studies since it is not applicable for the studies.

Peptides and Drugs

Compound 48/80, vespid mastoparan, rocuronium, tubocurarine, ciprofloxacin, levofloxacin, moxifloxacin, and ofloxacin were from Sigma. Cortistatin was from Tocris Biosciences. PAMP (9-20) was custom synthesized and purified to ≥98% by Genscript. Leuprolide was from Genscript. Substance P, kallidin, mastoparan, cetrorelix, octreotide, sermorelin (growth hormone releasing factor 1-29), icatibant (HOE-140) were from Anaspec. Atracurium and mivacurium were from Santa Cruz Biotechnology. Recombinant human insulin was from Roche. Goat anti-mouse IgE (Ab9162) was from Abcam.

Drug Preparation and Storage

Atracurium, mivacurium, tubocurarine, and all fluoroquinolone solutions were prepared on the day of the experiment because the potencies of the first three were found to be susceptible to oxidation and/or freeze-thaw effects, while the solubility of the fluoroquinolones was best when prepared fresh. Propranolol also was prepared fresh on the day of the experiment to minimize the chances of a loss in potency. All fluoroquinolones except levofloxacin were dissolved into CIB adjusted to pH 3.5. All other drugs were prepared as 100×-1000× aliquots and stored at −80° C. before thawing at 4° C. and diluting into calcium imaging buffer or saline.

Mrgpr RT-PCR Screen

Ribonucleic acid (RNA) was purified from $4 \times 10^4$ mouse peritoneal mast cells with a Qiagen RNEasy Micro column, according to the manufacturer's suggestions. RNA was treated for 20 minutes with DNAse I (New England Bio-Labs) and re-purified on another RNEasy Micro column. 8 ng of RNA was used to generate first strand cDNA using a SuperScript III kit (Invitrogen) according to the manufacturer's instructions, using oligo dT primers and scaling the recommended 10 μl reaction up to 60 μl. The negative control reaction was the same except that SuperScript III reverse transcriptase was replaced by water. 25 μl PCR reactions were run with 12.5 μl RedTaq ReadyMix (Sigma), 0.5 μl DMSO, 0.25 μl each of 50 μM gene-specific forward and reverse primers, 10 μl water, and 2 μl mixture from the cDNA or negative control synthesis reactions. All reactions used a 4 minute initial step at 95° C., 30 seconds annealing at specific temperatures (described below), 40 seconds extension at 72° C., and 25 seconds at 95° C. (with the last three steps repeated 39 times), and a final 4 minute step at 72° C. Low stringency PCR was set to 60° C. annealing; otherwise, annealing temperatures were: 62° C. for MrgprA1, MrgprA10, MrgprB2, and MrgprB6; 64° C. for MrgprA2, MrgprA3, MrgprA4, MrgprA6, MrgprA16, MrgprA18, and MrgprB11; 65° C. for MrgprA9, MrgprA19, MrgprB1, MrgprB3, MrgprB5, and MrgprB8; 66° C. for MrgprA12 and MrgprB10; 63° C. for MrgprB4; 61° C. for MrgprA14; and 65.5° C. for MrgprC11.

Primers were as follows.

```
MrgprA1 (for atccagcaagaggaatgggg (SEQ ID NO: 9),
rev tgtgacctaggaggaagaagaag (SEQ ID NO: 10));

MrgprA2 (for cctcctacacaagccagcaa (SEQ ID NO: 11),
rev aagcacaagtgaaagatgatgct (SEQ ID NO: 12));

MrgprA3 (for gctacatccagcaagaggaatg (SEQ ID NO: 13),
rev gcaaaaattcctttgggtagggt (SEQ ID NO: 14));

MrgprA4 (for cctgtgtgctgtgatctggt (SEQ ID NO: 15),
rev tcacggttaatccagggcac (SEQ ID NO: 16));

MrgprA6 (for cattttcctcccccaacagt (SEQ ID NO: 17),
rev atgcctgaatgagcccacaa (SEQ ID NO: 18));

MrgprA9 (for cagtgatctacatccagcaaaagg (SEQ ID NO: 19),
rev gcgtggaagctatgatgcga (SEQ ID NO: 20));

MrgprA10 (for cagtggtccaccatctccaa (SEQ ID NO: 21),
rev acaggcaagagagtcatggtt (SEQ ID NO: 22));

MrgprA12 (for tcagggatcgggtgaagcac (SEQ ID NO: 23),
rev gagcatttgaaggtgttgttgga (SEQ ID NO: 24));

MrgprA14 (for ggttgccctgtgtttcttc (SEQ ID NO: 25),
rev tattgccagtcagtaagctgag (SEQ ID NO: 26));

MrgprA16 (for gccctctggttcccattact (SEQ ID NO: 27),
rev gtttttggaccactgaggcatt (SEQ ID NO: 28));
```

-continued

```
MrgprA18 (for tgctctggttttctcctttgc (SEQ ID NO: 29),
rev tgaggcatgtcaagtcagtca (SEQ ID NO: 30));

MrgprA19 (for caggacccagatcacgacac (SEQ ID NO: 31),
tcctgggcttccgatttcac (SEQ ID NO: 32));

MrgprB1 (for attagccttcatcaggcacca (SEQ ID NO: 33),
ccagcccaactaaggcaatg (SEQ ID NO: 34));

MrgprB2 (for gtcacagaccagataacacttcc (SEQ ID NO: 35),
cagccatagccaggttgagaa (SEQ ID NO: 36));

MrgprB3 (for acctggctgtggctgatat (SEQ ID NO: 37),
rev gctgaacccacagagaacca (SEQ ID NO: 37));

MrgprB4 (for tctggctggtgctgatttctt (SEQ ID NO: 38),
rev accacgaggctcaacaataga (SEQ ID NO: 39));

MrgprB5 (for ctgtggttccttctgtgtcca (SEQ ID NO: 40),
rev tttccagttccccagacctt (SEQ ID NO: 41));

MrgprB6 (for tctgtctacatcctcaacctgg (SEQ ID NO: 42)),
rev attatctcatgaggaaggctcaa (SEQ ID NO: 43));

MrgprB8 (for agagaatgcaaagcatgcga (SEQ ID NO: 44),
rev gaggaagtttgccccagaca (SEQ ID NO: 45));

MrgprB10 (for cactggtcacattgccaacc (SEQ ID NO: 46,
rev ggggatggaatcaatgtccaaga (SEQ ID NO: 47);

MrgprB11 (for accacttgctattatccctcca (SEQ ID NO: 48),
rev aggatgagactggacccaca (SEQ ID NO: 49));

MrgprC11 (for cagcacaagtcagctcctcaa (SEQ ID NO: 50),
rev atgcccatgagaaaggacagaacc (SEQ ID NO: 51)).
```

Expression Constructs

Mrgpr genes were cloned and inserted into the pcDNA3.1 mammalian expression plasmid using standard techniques. All mouse genes had a Kozak sequence at their N-terminus and also encoded a C-terminal FLAG tag separated from the genes by the amino acid linker DIIL.

cDNA Constructs

First strand cDNA was prepared as described for RT-PCR screens, and amplification was performed using the Q5 HotStart High Fidelity Master Mix (New England Biolabs). At least five different clones each prepared from wild type and mutant mice were sequenced to verify the presence of the deletion in the mutant and the absence of any other mutation from wild type or mutant.

Calcium Imaging in HEK293 Cells

In initial screens, HEK293 cells (not tested for *Mycoplasma* but rapidly dividing) were transiently transfected with gene constructs including a C-terminal FLAG tag, and plated on 100 μg/ml poly-D-lysine coated glass cover slips six hours after transfection. 24 hours later, cells were loaded with AM esters of the calcium indicators Fura-2 or Fluo-4 (Molecular Probes) along with 0.02% Pluronic F-127 (Molecular Probes) for 45 minutes at 37° C. Fura-2 loaded cells were imaged during 340 and 380 nm excitation, and Fluo-4 loaded cells were imaged during 488 nm excitation. Later experiments utilized cell lines stably expressing receptors along with transient or stable expression of the promiscuous G protein Gα15. Cells were imaged in calcium imaging buffer (CIB; NaCl 125 mM, KCl 3 mM, $CaCl_2$ 2.5 mM, $MgCl_2$ 0.6 mM, HEPES 10 mM, glucose 20 mM, $NaHCO_3$ 1.2 mM, sucrose 20 mM, brought to pH 7.4 with NaOH). Unless otherwise specified, drugs were perfused into the chamber for 45 to 60 seconds and responses were monitored at 5-second intervals for an additional 60-90 seconds.

$EC_{50}$ Determination

HEK293 cells stably expressing Galpha15 and either MrgprB2 or MrgprX2 were plated at $4\times10^4$ cells per well in 96-well plates and incubated overnight. The next day, media was removed and replaced with imaging solution from the FLIPR Calcium 5 assay kit (Molecular Devices), diluted according to manufacturer's suggestions in Hank's Balanced Salt Solution (HBSS) with 20 mM HEPES, pH 7.4. Cells were incubated at 37° C. for 60 minutes, and allowed to recover for 15 minutes at room temperature before imaging in a Flexstation 3 (Molecular Devices). Wells were imaged according to manufacturer's specifications for 120 seconds, with 50 μl of test substances at 3× concentration added 30 seconds after imaging began. Responses were determined by subtracting the minimum signal from the maximum signal. Substances were tested in duplicate wells, the signals were averaged, and $EC_{50}$s were determined for each trial by normalizing to the peak response to the substance in that trial. All drugs were dissolved in HBSS+HEPES solution, with the following exceptions due to solubility issues: cetrorelix acetate was dissolved in saline containing 2.5 mM $CaCl_2$ and 0.6 mM $MgCl_2$, and fluoroquinolones except ofloxacin were dissolved in the same solution except that the pH was adjusted with HCl to 3.5; ofloxacin required 100 μg/ml of lactic acid for full solubility. Peptides sometimes lost potency after a freeze-thaw cycle, so most peptides were prepared directly from lyophilized stock.

Peritoneal Mast Cell Purification and Imaging

Adult male and female mice 2-5 months of age were sacrificed through $CO_2$ inhalation. A total of 12 mls of ice cold mast cell dissociation media (MCDM; HBSS with 3% fetal bovine serum and 10 mM HEPES, pH 7.2) were used to make two sequential peritoneal lavages, which were combined and cells were spun down at 200 g. The pellet from each mouse was resuspended in 2 mls MCDM, layered over 4 mls of an isotonic 70% Percoll suspension (2.8 mls Percoll, 320 µls 10×HBSS, 40 µl 1 M HEPES, 830 µl MCDM), and spun down for 20 minutes, 500 g, 4° C. Mast cells were recovered in the pellet. Purity was >95%, as assayed by avidin staining and by morphology. Mast cells were resuspended at $5 \times 10^5$-$1 \times 10^6$ cells/ml in DMEM with 10% fetal bovine serum and 25 ng/ml recombinant mouse stem cell factor (Sigma), and plated onto glass cover slips coated with 30 µg/ml fibronectin (Sigma). For counting, instead of plating, suspended mast cells were diluted 1/10 and affixed to slides by spinning at 1000 rpm for 5 minutes at 4° C. on a CytoSpin (Thermo Scientific).

For imaging, after two hours of incubation at 37° C., 5% $CO_2$, mast cells were loaded with Fluo-4 along with 0.02% Pluronic F-127 for 30 minutes at room temperature, washed 3 times in CIB and used immediately for imaging. Cells were used within two hours of loading. Cells were identified as responding if the $[Ca^{2+}]_i$ rose by at least 50% for at least 10 seconds, which clearly distinguishes a ligand-induced response from random flickering events. Average traces were calculated by taking the average response from each cell in a mouse, and averaging those.

BAC Transgenic Mice Generation

The BAC clone RP23-65I23 was purchased from Children's Hospital Oakland Research Institute. This clone contains the MrgprB2 locus, ~60 kb of 5' genomic sequence and over 100 kb of 3' genomic sequence. Recombineering in bacteria was used to introduce eGFP-Cre and a polyA signal immediately after the MrgprB2 start codon (Metcalfe, D. D., Baram, D. & Mekori, Y. A. Mast cells. *Physiological reviews* 77, 1033-1079 (1997)). The BAC was linearized with NotI (New England Biolabs) and injected into pronuclei from single cell fertilized C57Bl/6 eggs. Eggs were implanted into pseudopregnant females. Three BAC mouse lines were established. Though mice were already in a C57Bl/6 background, they were crossed for at least four generations to WT and tdTomato reporter mice in the C57Bl/6 background before use in experiments. BAC mice were mated to ROSA26$^{Tdtomato}$ mice purchased from Jackson Labs for imaging studies. Experiments for FIG. 1 used mice homozygous for ROSA26$^{Tdtomato}$ because the tdTomato signal often was heterogeneous and weak in heterozygous mice. Genotyping reactions for BAC mice were run at 61° C. annealing, and primers were: forward, tatatcatggccgacaagca; reverse, cagaccgcgcgcctgaaga. Both primers are in the eGFP-Cre reading frame but the entire gene and correct placement in the MrgprB2 locus was verified by previous sequencing.

MrgprB2 Mutant Mice Generation mRNAs encoding zinc finger nucleases targeting MrgprB2 were purchased from Sigma. The binding sites were GTTCCTGGGCATCCG (SEQ ID NO: 52) and TGCACACGAATGCCTTCACTG (SEQ ID NO: 53), corresponding to bases 180-194 and 196-216, respectively, of the MrgprB2 open reading frame. mRNA was diluted to 2 ng/ml in 1 mm Tris-HCl buffer, pH 7.4, with 0.25 mm EDTA, and injected into the pronuclei of single cell fertilized eggs in the C57Bl/6 strain. No overt signs of toxicity were observed. Embryos were implanted into pseudopregnant females. DNA flanking the binding sites was amplified from founder mice and screened for mutations using the Cel-1 assay kit (Transgenomics), according to the manufacturer's suggestions. 3 of the first 28 mice were identified and confirmed by DNA sequencing to carry small mutations, and no more screening was performed. In addition to the 4 bp mutation used in this study, a mouse carrying a 1 bp deletion and another with a 2 bp deletion were identified.

Wild Type and MrgprB2$^{MUT}$ Mouse Genotyping

Primers used for wild type mice were GGTTCCTGGGCATCCGTAT (SEQ ID NO: 54) and GGTTCCTGGGCATCCGTAT (SEQ ID NO: 55), and reactions were run at an annealing temperature of 62.8° C.

Primers for MrgprB2$^{MUT}$ mice were GTTCCTGGGCATCCGCAC (SEQ ID NO: 56) and CTTCCGCCTGAACCTTCGGT (SEQ ID NO: 57), and reactions were run at 64.0° C. annealing temperature.

Avidin Labeling of Tissue

Adult male and female mice up to 8 months of age were anesthetized with pentobarbital and perfused with 20 ml 0.1 M PBS (pH 7.4, 4° C.) followed with 25 ml of fixative (4% formaldehyde (vol/vol), 4° C.). Heart, trachea, and skin sections were dissected from the perfused mice. Tissues were post-fixed in fixative at 4° C. overnight. When skin sections were the only tissues needed, they were dissected and placed in fixative directly after asphyxiation of mice by $CO_2$ inhalation, eliminating the perfusion step. Tissues were cryoprotected in 20% sucrose (wt/vol) for more than 24 h and were sectioned (20 µm width) with a cryostat. The sections on slides were dried at 37° C. for 30 min, and fixed with 4% paraformaldehyde at 21-23° C. for 10 min. The slides were pre-incubated in blocking solution (10% normal goat serum (vol/vol), 0.2% Triton X-100 (vol/vol) in PBS, pH 7.4) for 1 or 2 h at 21-23° C., then incubated with 1/500 FITC-avidin (Sigma) or rhodamine-avidin (Vector Labs) for 45 minutes. Sections were washed three times with water or PBS and a drop of Fluoromount G (SouthernBiotech) was added before cover slips were placed on top. Heart mast cells were examined near cavities because the density was much higher than elsewhere in the tissue; avidin-positive, tdTomato-negative cells were observed embedded in muscle tissue in very low numbers, but their identity was unclear.

For avidin labeling of peritoneal mast cells, cells were plated as described in the mast cell purification section, fixed with 4% paraformaldehyde at 21-23° C. for 10 min, incubated with 1/1000 avidin in PBS for 30 minutes at 21-23° C., and washed with PBS before immediate imaging.

Stomach Section Immunocytochemistry

Adult male and female mice up to 8 months of age were anesthetized with pentobarbital and perfused with 20 ml 0.1 M PBS (pH 7.4, 4° C.) followed with 25 ml of fixative (4% formaldehyde (vol/vol), 4° C.). Stomach sections were removed, washed thoroughly, postfixed in 4% formaldehyde for two hours, and prepared for sectioning by incubation in a 30% sucrose solution for 48 hours. Tissue samples were mounted in cryoembedding media and frozen, and 14 µm sections were made using a crytostat and then fixed onto slides. Slides were washed with a 0.2% Triton X-100 PBS solution, incubated for one hour in a 10% normal goat serum solution, and then incubated overnight at 4° C. with a 1:20 dilution of rat monoclonal anti-mouse MCPT1 (monoclonal antibody RF6.1, eBiosciences) in a 0.2% Triton/1% normal goat serum solution. Slides were washed with the 0.2% Triton solution and incubated for two hours at room temperature in Triton solution with a 1:500 dilution of a goat anti-rat IgG Alexa Fluor 488 conjugated antibody (Life Technologies). Slides were washed in PBS before cover slips were added with an anti-fade solution for imaging.

Peripheral White Blood Cell Preparation

Blood was collected from MrgprB2-tdTomato mice via cardiac punctures with a syringe containing PBS with 30 units/ml heparin and 5 mM EDTA, diluted 1:1 with the same solution, and allowed to cool to room temperature before layering over 6 mls of a Histopaque-1119 solution in a 15 ml conical tube. Tubes were centrifuged at 700 g for 30 minutes, and white blood cells were collected at the interface between the PBS and Histopaque solutions. Cells were washed with PBS and spun down at 500 g for 10 minutes a total of three times. Cells were spun onto poly-lysine coated slides in a Cytospin 4 (Thermo Scientific) at 600 rpm for 3-5 minutes, dried overnight on a 37° C. heating block, and incubated for 2 minutes with Hoechst 33342 diluted to 0.5 µg/ml in PBS before coverslip mounting with an anti-fade solution. In parallel, cells were also stained in suspension with Hoechst 33342, spun the cells down, and mixed the resuspended cells directly in a PBS/anti-fade solution before placing directly onto slides and mounting coverslips on the suspension. No tdTomato-positive cells were seen in any preparation using either method.

Tissue Histamine Release Studies

Whole tracheae or segments of skin isolated from the abdominal aspect of shaved male and female mice up to 6 months of age (4-8 mg wet weight) were dissected and cleaned of connective tissue. After a 60 minutes in incubation period in oxygenated Kreb's bicarbonate buffer solution (37° C.), the tissue was treated with either vehicle or Compound 48/80 for 30 min. The supernatant solution was saved for histamine analysis. The tissue was then subjected to 8% percholoric acid in a 37° C.-waterbath for 15 minutes to obtain total histamine content. Histamine was assayed by the automated fluorometric technique previously described[2].

Tracheal Contractions

Tracheal contractions were carried out as previously described (Lagunoff, D., Martin, T. W. & Read, G. Agents that release histamine from mast cells. *Annual review of pharmacology and toxicology* 23, 331-351). For allergen (ovalbumin, OVA) responses, mice were actively sensitized by injecting 0.2 mL of an OVA solution (3.75 µg/mL) mixed with Al(OH)$_3$ three times at an interval of 2 days. Experiments were conducted on male and female animals 8-12 weeks of age beginning two weeks following the first injection. Trachea were cleaned of connective tissue and tracheal rings (whole or laterally divided in half), were suspended between two tungsten stirrups in 10 mL organ chambers filled with Krebs' that was warmed to 37° C. and bubbled with 95% O$_2$-5% CO$_2$ to maintain a pH of 7.4. One stirrup was connected to a strain gauge (model FT03; Grass Instruments, Quincy, Mass.), and tension was recorded on a Grass Model 7 polygraph (Grass Instruments, Quincy, Mass.). Preparations were stretched to a resting tension of 0.2 g, and washed with fresh Krebs' buffer at 15-minute intervals during a 60 minute equilibration period. After equilibration, trachea were challenged with either OVA (10 µg/mL), or Compound 48/80. At the end of each experiment, all trachea were maximally contracted with carbachol (1 µM). All results are expressed as a percentage of maximum contraction.

Hindpaw Swelling and Extravasation

Adult male mice up to 8 months of age were anesthetized with an i.p. injection of 50 mg/kg pentobarbital (Sigma). 15 minutes after induction of anesthesia, mice were injected i.v. with 50 µl of 12.5 mg/ml Evans Blue (Sigma) in saline. 5 minutes later, 5 µl of the test substance (or 7 µl of anti-IgE) was administered by intraplantar injection in one paw and saline was administered in the other paw. Paw thickness was measured by calipers immediately after injection. 15 minutes later (30 minutes after anti-IgE), paw thickness was measured again and mice were sacrificed by decapitation. Paw tissue was collected, dried for 24 hours at 50° C., and weighed. Evans Blue was extracted by a 24 hour incubation in formamide at 50° C., and the O.D. was read at 620 nm using a spectrophotometer. For studies using ketotifen, mice were injected i.p. with 25 µl of a 10 mg/ml solution of ketotifen at the same time as pentobarbital.

Systemic Anaphylaxis Assay

To minimize stress, animals were transported to the procedure area the day before injections. Adult male and female mice up to 8 months of age (25 to 35 grams) were given an intraperitoneal injection of 80 µg propranolol in saline (2 mg/ml) immediately after removal from their cages, and then placed back in their cages for 30 minutes before intravenous injections. The intravenous injections were performed on one mouse at a time. For each injection, a mouse was placed in a transport box and brought to a room with no other mice, to minimize stress from vocalizations during injection. The mouse was then placed in a restrainer, and the injection was performed within 4 minutes of restraint because it was observed that longer restraint times affected body core temperature independent from the injection. Tail veins were dilated by repeated wiping of tail with a tissue soaked in 100% ethanol, followed by injection of ciprofloxacin in a 0.25 ml Hamilton syringe fit with a 30.5 gauge needle (BD Biosciences). The injection was determined to be successful only when all of the criteria were met: blood appeared in the syringe after needle insertion, all tail veins were visible after injection, and the mouse bled slightly from the injection site after needle withdrawal. The injection site was swabbed until blood stopped flowing, the mouse was placed in a separate cage from its housing cage, one mouse per cage, and returned to the room it was brought from. At least one wild type and one mutant mouse were used for each experimental session. Body core temperature was measured with a rectal thermometer.

Mouse Peritoneal Mast Cell Histamine Release Assay

Mast cells were purified as with the calcium imaging assay and allowed to recover for 2 hours in DMEM with 10% FBS and 25 ng/ml mouse stem cell factor in a 37° C. incubator with 5% CO$_2$. Cells were then spun down, resuspended in CIB, counted, and plated at 300 cells/well in 75 µl CIB in 96-well plates coated with 20 µg/ml fibronectin (Sigma). They were allowed to adhere to the substrate for 45 minutes at 37° C. in atmospheric conditions (i.e. CO$_2$ levels were not adjusted) before assay. For the assays, cells were removed to room temperature and 75 µl of 2× concentrations of tested substances (all in CIB except for ciprofloxacin, which was in saline with 2.5 mM CaCl$_2$ and 0.6 mM MgCl$_2$, pH 3.5) were added. After 5 minutes, 40 µl of supernatant was aspirated, diluted with 40 µl CIB and frozen at −80° C. until histamine levels were determined. Anti-IgE treatment was similar, except that cells were incubated for 30 minutes at 37° C. after anti-IgE was added before aspiration of supernatant. Histamine content was determined by using an HTRF histamine assay kit (Cisbio Assays) according to the manufacturer's instructions.

Human Mast Cell Culture

LAD2 (Laboratory of Allergic Diseases 2) human mast cells were cultured in StemPro-34 SFM medium (Life Technologies) supplemented with 2 mM L-glutamine, 100 U/ml penicillin, 50 µg/ml streptomycin, and 100 ng/ml recombinant human stem cell factor (Peprotech). The cell suspensions were seeded at a density of 0.1×10$^6$ cells/ml and maintained at 37° C. and 5% CO$_2$, and periodically tested for the expression of CD117 and FcεRI by flow cytometry. Cell culture medium was hemi-depleted every week with fresh medium.

LAD2 Degranulation Assay

LAD2 cells were sensitized for 20 hours with 0.5 µg/ml biotin-conjugated human IgE (Abbiotec). Cells were washed, resuspended in Hepes buffer (10 mM HEPES, 137 mM NaCl, 2.7 mM KCl, 0.38 mM $Na_2HPO_4.7H_2O$, 5.6 mM glucose, 1.8 mM $CaCl_2.H_2O$, 1.3 mM $MgSO_4.7H_2O$, 0.4% BSA, pH 7.4) at $0.025\times10^6$ per well, and then stimulated with 0.1 µg/ml streptavidin (Life Technologies) or other agonists at the indicated concentrations for 30 minutes at 37° C./5% $CO_2$. The β-hexosaminidase released into the supernatants and in cell lysates was quantified by hydrolysis of p-nitrophenyl N-acetyl-β-D-glucosamide (Sigma-Aldrich) in 0.1 M sodium citrate buffer (pH 4.5) for 90 minutes at 37° C. The percentage of β-hexosaminidase release was calculated as a percent of total content. Agonists tested were Compound 48/80, mastoparan, icatibant, atracurium bessylate, and ciprofloxacin hydrochloride.

EIA and ELISA

LAD2 cells were washed with medium, suspended at $0.25\times10^6$ cells per well, and incubated with Compound 48/80, mastoparan, icatibant, atracurium or ciprofloxacin at the indicated concentrations for 3-24 hours at 37° C./5% $CO_2$. Cell-free supernatants were harvested and analyzed for $PGD_2$ release by an EIA (Cayman chemical), while TNF content was quantified using an ELISA kit (eBioscience) according to the manufacturer's instruction. The minimum detection limits were 55 pg/ml for $PGD_2$ and 5.5 pg/ml for TNF.

Measurement of Histamine Release from LAD2 Cells

LAD2 cells were washed, suspended in BSA-free Hepes buffer at $0.1\times10^6$ per well, and incubated with Compound 48/80, mastoparan, icatibant, atracurium or ciprofloxacin at the indicated concentrations for 30 minutes at 37° C./5% $CO_2$. A histamine (Sigma-Aldrich) stock solution of 100 µg/ml was prepared and stored at −20° C. The working standards of 4000 ng/ml to 7.8 ng/ml were freshly prepared using two-fold serial dilution. O-phthalaldehyde (OPT; Sigma-Aldrich) was dissolved in acetone-free methanol (10 mg/ml) and kept in dark at 4° C. Histamine standards and cell-free supernatants (60 µL) were transferred to a flat bottom 96 black well microplate and mixed with 12 µl 1M NaOH and 3 µl OPT. After 4 minutes at room temperature, 6 µl 3M HCl was added to stop the histamine-OPT reaction. Fluorescence intensity was measured using a 355 nm excitation filter and a 460 emission filter.

siRNA Transfection of LAD2 Cells

Expression of MrgprX2 was down-regulated with ON-TARGET plus SMARTpool siRNA against MrgprX2 and control siRNA from Dharmacon. LAD2 cells were washed with medium, suspended at $0.5\times10^6$ cells per well, and transfected with 100 nm MrgprX2 siRNA and control siRNA in antibiotic-free StemPro medium using Lipofectamine 3000 (Life Technologies) according to the manufacturer's instruction at 37° C./5% $CO_2$. At 48 hours, knockdown was confirmed by reverse-transcriptase PCR, and the cells were used for degranulation assays.

Example 2: MrgprB2 is the Orthologue of Human MrgprX2

Figure 1B:
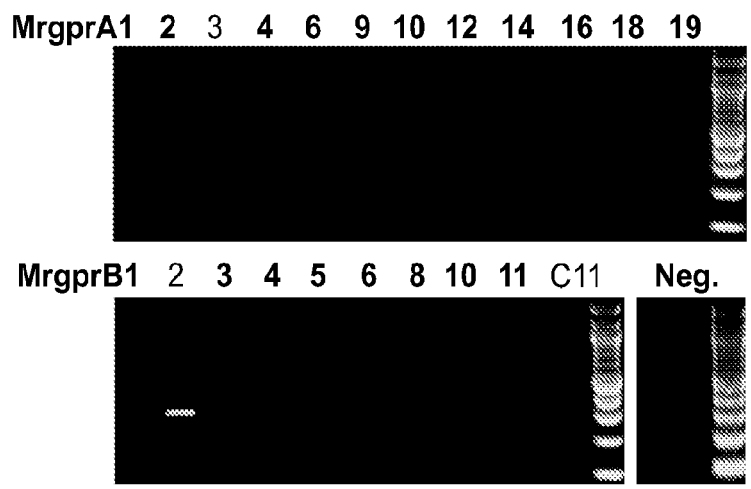
FIG. 1B shows results from a stringent reverse transcription polymerase chain reaction (RT-PCR) screen that identified expression of MrgprB2 transcript (arrow) in mouse peritoneal mast cells. The Mrgpr gene names are indicated on the top of the gel pictures. No band was seen when reverse transcriptase was omitted from the cDNA synthesis reaction (Neg.).
Figure 5A:
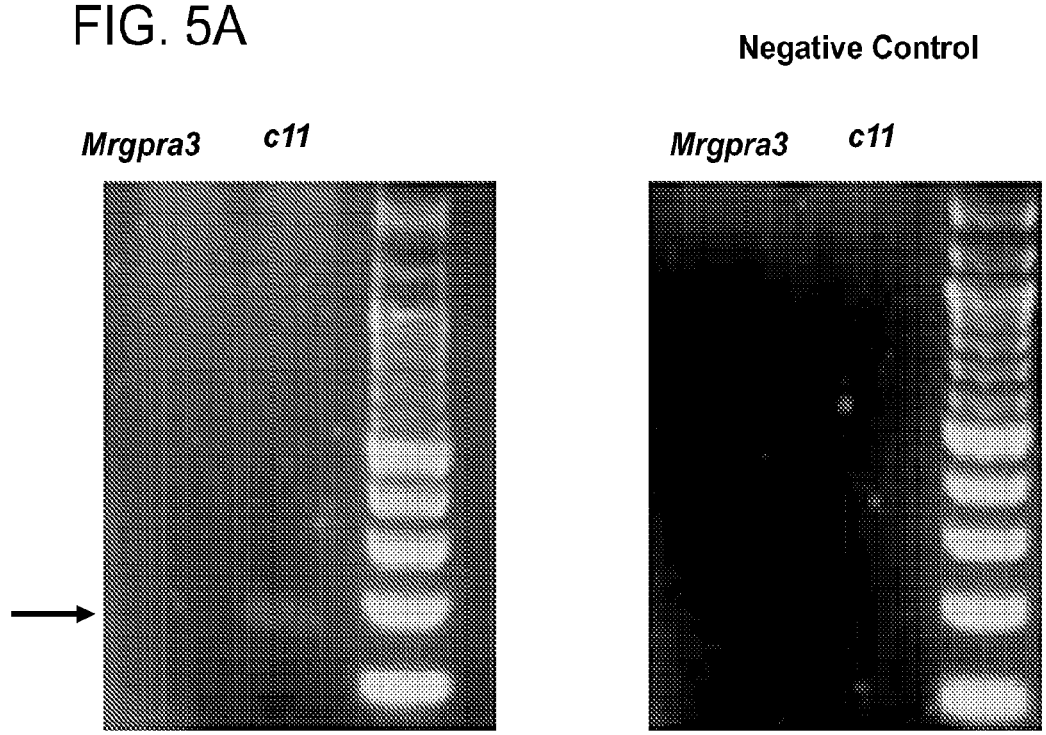
FIG. 5A is a photograph of a blot showing that MrgprX1 orthologues are not expressed at relevant levels in mast cells under naive conditions.
Figure 5B:
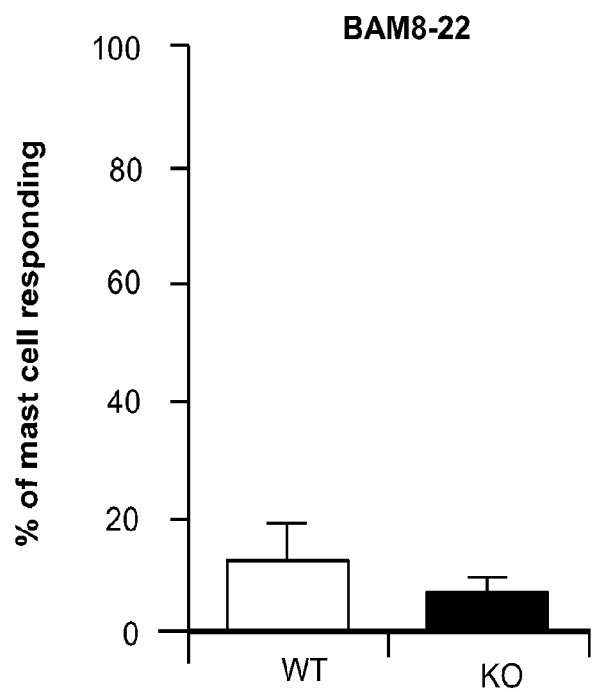
FIG. 5B is a bar chart showing the percentages of peritoneal mast cells responding to the MrgprX1 and MrgprC11 agonist Bovine Adrenal Medulla derived peptide, fragment 8-22 (BAMS- 22, 500 nM). Activation was assayed by measuring rises in intracellular calcium, using imaging of the Fluo-4 dye. Differences are not significant (p=0.39). Group data are expressed as mean±standard error of the mean. Two-tailed unpaired Student's t test was used to determine significance in statistical comparisons.

Responsiveness to basic secretagogues is conserved among mammals (Halpern, B. N. & Wood, D. R. The action of promethazine (phenergan) in protecting mice against death due to histamine. *British journal of pharmacology and chemotherapy* 5, 510-516 (1950)), and also is found in birds (Taneike, T., Miyazaki, H., Oikawa, S. & Ohga, A. Compound 48/80 elicits cholinergic contraction through histamine release in the chick oesophagus. *General pharmacology* 19, 689-695 (1988)), indicating an ancient, fundamental role for its mechanism. Many basic secretagogues are endogenous peptides, often linked to inflammation; however, they activate connective tissue mast cells only at high concentrations and independent of their canonical receptors, so another mechanism of stimulation must exist (Ferry, X., Brehin, S., Kamel, R. & Landry, Y. G protein-dependent activation of mast cell by peptides and basic secretagogues. *Peptides* 23, 1507-1515 (2002)). Several candidates which bind polycationic compounds have been proposed as basic secretagogue receptors (Ferry, X., Brehin, S., Kamel, R. & Landry, Y. G protein-dependent activation of mast cell by peptides and basic secretagogues. *Peptides* 23, 1507-1515 (2002); Purcell, W. M., Doyle, K. M., Westgate, C. & Atterwill, C. K. Characterisation of a functional polyamine site on rat mast cells: association with a NMDA receptor macrocomplex. *Journal of neuroimmunology* 65, 49-53 (1996); Tatemoto, K. et al. Immunoglobulin E-independent activation of mast cell is mediated by Mrg receptors. *Biochemical and biophysical research communications* 349, 1322-1328, (2006); Sick, E., Niederhoffer, N., Takeda, K., Landry, Y. & Gies, J. P. Activation of CD47 receptors causes histamine secretion from mast cells. *Cellular and molecular life sciences: CMLS* 66, 1271-1282, (2009). Among these, MrgprX2 has been screened with the most compounds (Tatemoto, K. et al. Immunoglobulin E-independent activation of mast cell is mediated by Mrg receptors. *Biochemical and biophysical research communications* 349, 1322-1328, (2006); Robas, N., Mead, E. & Fidock, M. MrgX2 is a high potency cortistatin receptor expressed in dorsal root ganglion. *The Journal of biological chemistry* 278, 44400-44404, (2003); Subramanian, H., Gupta, K., Guo, Q., Price, R. & Ali, H. Mas-related gene X2 (MrgX2) is a novel G protein-coupled receptor for the antimicrobial peptide LL-37 in human mast cells: resistance to receptor phosphorylation, desensitization, and internalization. *The Journal of biological chemistry* 286, 44739-44749, (2011); Kashem, S. W. et al. G protein coupled receptor specificity for C3a and compound 48/80-induced degranulation in human mast cells: roles of Mas-related genes MrgX1 and MrgX2. *European journal of pharmacology* 668, 299-304, (2011); Subramanian, H. et al. beta-Defensins activate human mast cells via Mas-related gene X2. *Journal of immunology* 191, 345-352, (2013); Kamohara, M. et al. Identification of MrgX2 as a human G-protein-coupled receptor for proadrenomedullin N-terminal peptides. *Biochemical and biophysical research communications* 330, 1146-1152, (2005)), and siRNA knockdown studies support at least a partial role for MrgprX2 in activation by four non-canonical basic secretagogues (Subramanian, H., Gupta, K., Guo, Q., Price, R. & Ali, H. Mas-related gene X2 (MrgX2) is a novel G protein-coupled receptor for the antimicrobial peptide LL-37 in human mast cells: resistance to receptor phosphorylation, desensitization, and internalization. *The Journal of biological chemistry* 286, 44739-44749, (2011); Subramanian, H. et al. beta-Defensins activate human mast cells via Mas-related gene X2. *Journal of immunology* 191, 345-352, (2013)). However, no direct in vivo study or knockout model has been employed for any candidate. The investigation of MrgprX2 in mice is complicated because the gene cluster containing the four human MrgprX members is dramatically expanded in mice, consisting of 22 potential coding genes, many with comparable sequence identity to MrgprX2 (FIG. 1A). Therefore, a mouse MrgprX2 orthologue must be determined by expression pattern and pharmacology. A stringent RT-PCR screen in mouse primary mast cells uncovered a band for a single family member, MrgprB2 (FIG. 1B), while MrgprX1 orthologues were not expressed at relevant levels (FIG. 5A and FIG. 5B).

Figure 1C:
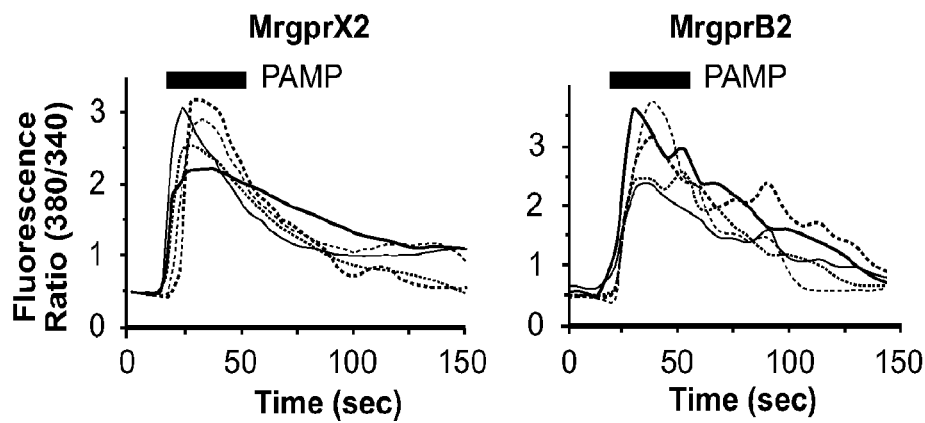
FIG. 1C shows exemplary traces of intracellular calcium concentrations [$Ca^{2+}$]i, as measured by ratiometric Fura-2 imaging, from HEK293 cells transiently transfected with a plasmid driving expression of MrgprB2 or MrgprX2 and exposed to bath application of 20 μM PAMP(9-20) (duration indicated by black line on top). Each trace is a response from a unique cell.
Figure 1D:
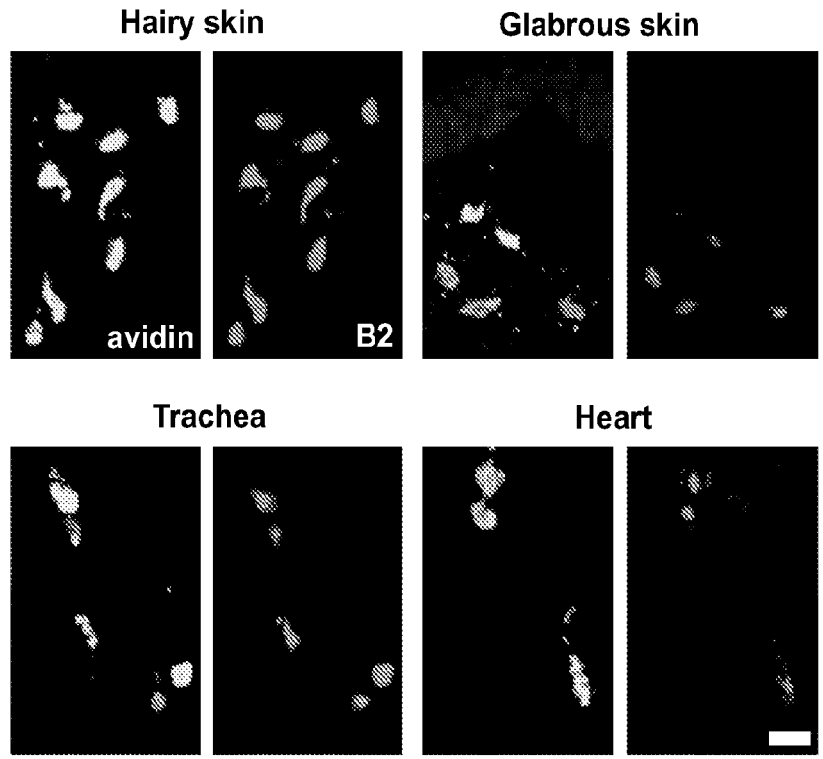
FIG. 1D is a series of photomicrographs showing shows representative confocal images from BAC transgenic mouse tissues. BAC mice expressing eGFP-Cre in the MrgprB2 open reading frame were mated to Rosa26-loxP-STOP-loxP-tdTomato reporter mice. Therefore, the expression of tdTomato is determined by the expression pattern of Cre, which is under control of MrgprB2 promoter. tdTomato (red) expression was compared to avidin staining (green), a marker for mast cells. Nearly 100% overlap between the two markers suggests that MrgprB2 is specifically contained in mast cells. Three mice were examined for all tissues except heart, where two mice were examined Percentages of avidin-positive mast cells that also were tdTomato-positive: glabrous skin, 97.5%; hairy skin, 90.1%; trachea, 97.2%; heart, 87.1%. Percentages of tdTomato-positive cells that also were avidin-positive: glabrous skin, 99.2%; hairy skin, 100%; trachea, 98.3%; heart, 99%. Total number of cells counted in each tissue was over 300, except for heart which was over 100. Heart mast cells were examined near cavities because the density was much higher than elsewhere in the tissue; avidin-positive cells that were negative for tdTomato were observed embedded in muscle tissue in very low numbers, but their identity was unclear. Scale bar is 20 µm.
Figure 6A:
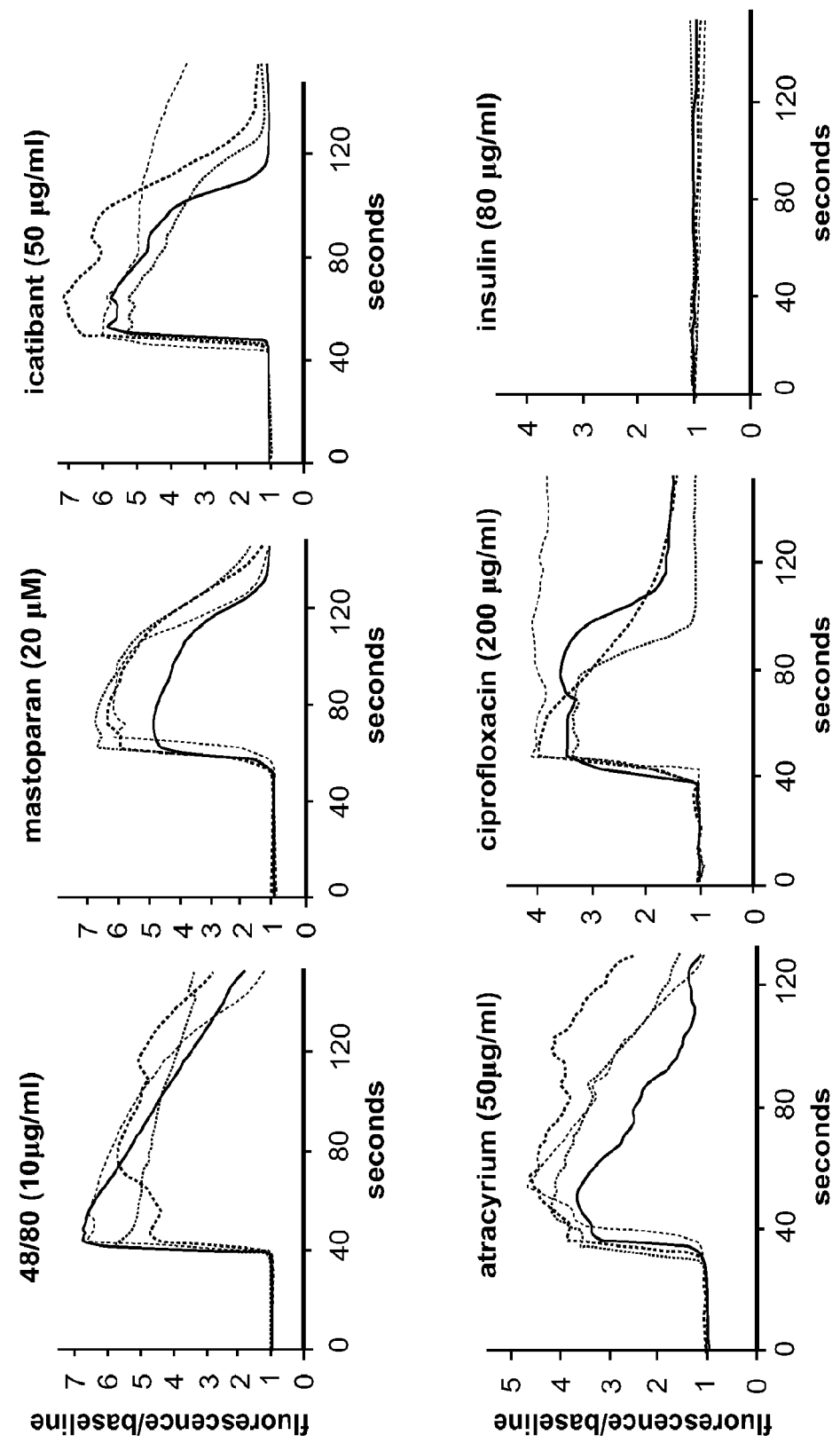
FIG. 6A is a series of line graphs that show basic secretagogues and drugs that induce pseudo-allergic reactions activate mouse MrgprB2 and human MrgprX2 expressed in HEK293 cells.
Figure 6B:
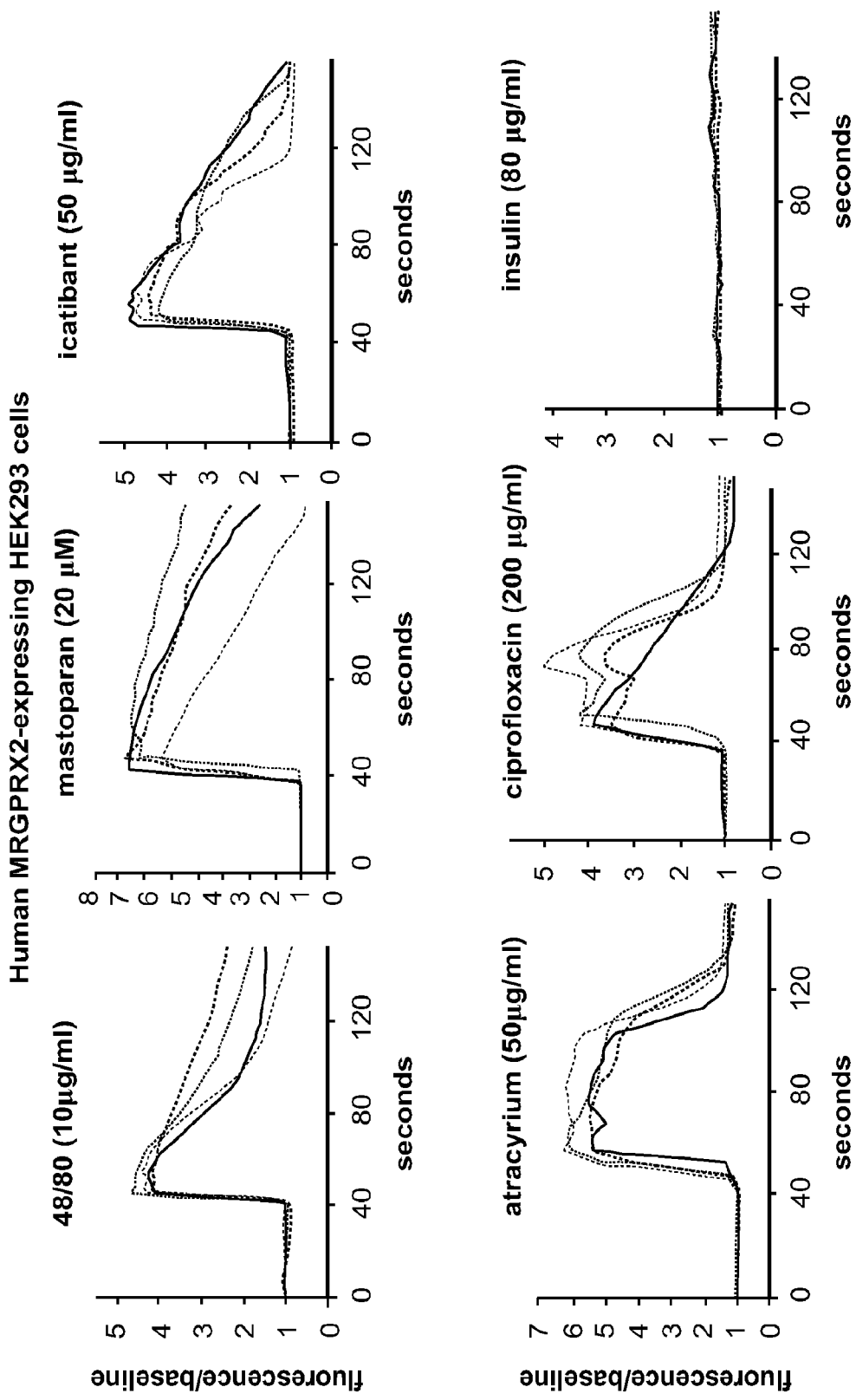
FIG. 6B shows example traces showing changes in [Ca2+]i, as measured by Fluo-4 imaging, from HEK293 cells expressing MrgprX2 and Gα15. Substances were perfused from the 30 to 90 second time period, except for ciprofloxacin, which was perfused between the 30 and 60 second time periods to minimize exposure to the low pH solutions it was dissolved in. Insulin was used as a negative control.
Figure 7:
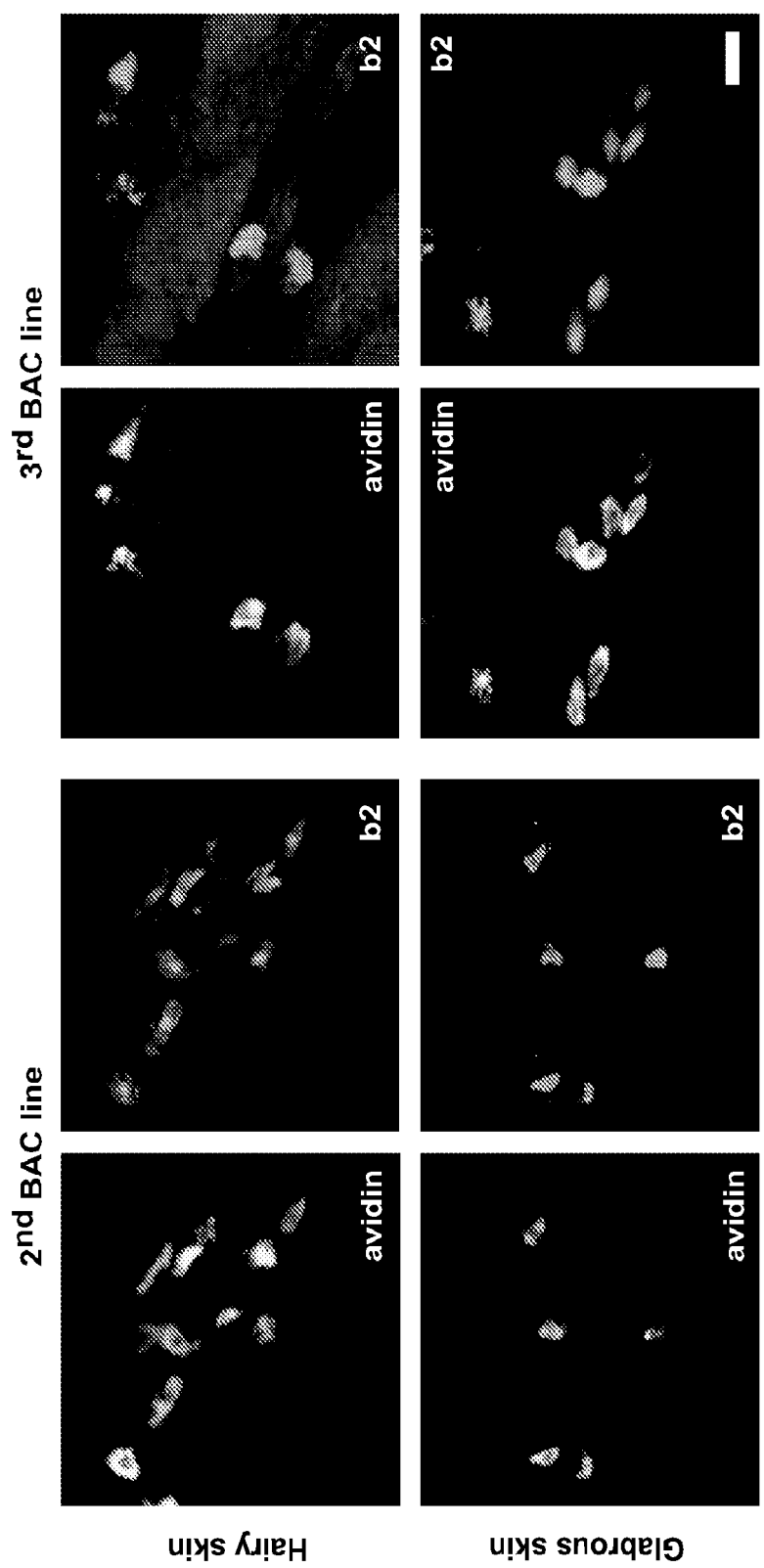
FIG. 7 is a series of photomicrographs showing that multiple lines of BAC transgenic mice confirm mast cell specific MrgprB2 expression.
Figure 8A:
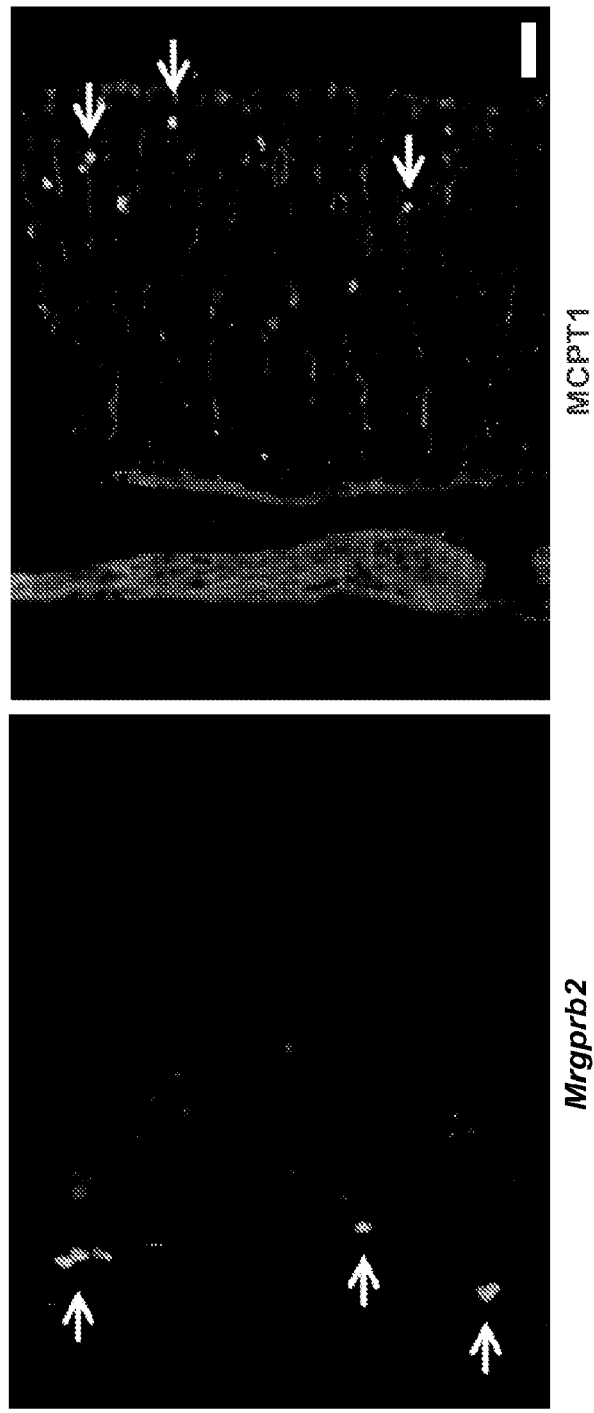
FIG. 8A-FIG. 8B show that MrgprB2 is not expressed in mucosal mast cells or peripheral white blood cells.
Figure 8B:
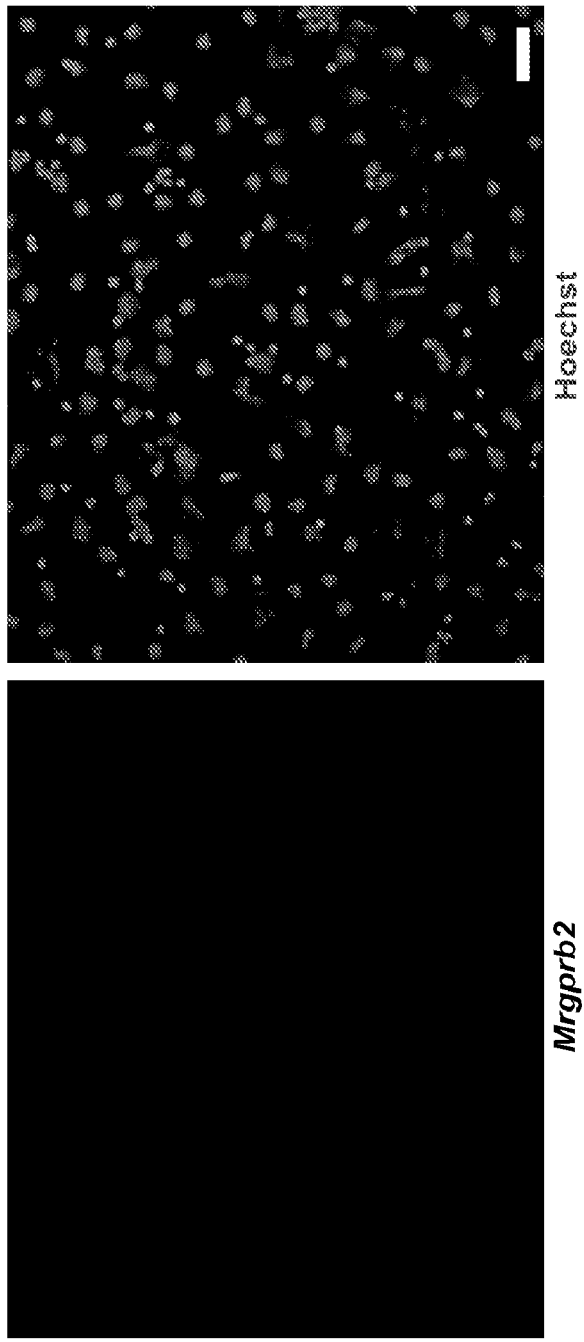

Functionally, HEK293 cells heterologously expressing MrgprB2 (MrgprB2-HEK) responded to the MrgprX2 agonist PAMP (9-20)[14] (FIG. 1C) and Compound 48/80 (48/80), a classical mast cell activator and canonical basic secretagogue (FIG. 6A, FIG. 6B, and FIG. 6C). MrgprB2-HEK cells also responded to other MrgprX2 ligands, including the basic secretagogue Substance P, but had no response to the MrgprX1 ligand chloroquine (CQ) (Liu, Q. et al. Sensory neuron-specific GPCR Mrgprs are itch receptors mediating chloroquine-induced pruritus. *Cell* 139, 1353-1365, (2009)); no closely related family members in mice responded to any compound (FIG. 5C, FIG. 6A, and FIG. 6C). To determine the expression of MrgprB2, MrgprB2 BAC transgenic mice in which the expression of eGFP-Cre recombinase was under the control of the MrgprB2 promoter were generated. Strikingly, Cre expression patterns indicate that MrgprB2 expression is highly specific to connective tissue mast cells (FIG. 1D, FIG. 7, FIG. 8A, and FIG. 8B). Together, the pharmacological and expression data indicate that MrgprB2 is the mouse orthologue of MrgprX2.

Example 3: MrgprB2 is the Mouse Mast Cell Basic Secretagogue Receptor

Figure 2A:
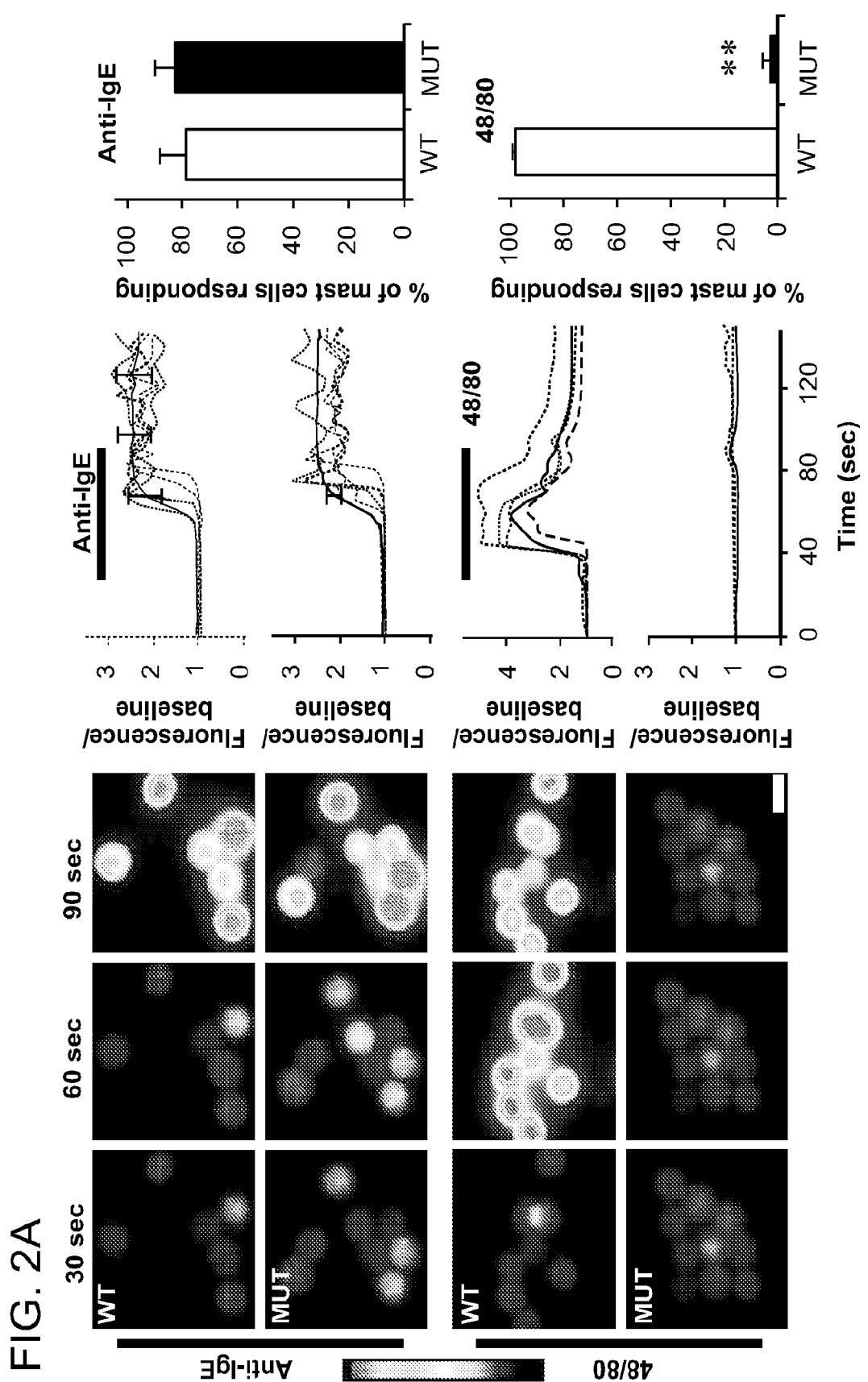
FIG. 2A (left) is a series of photomicrographs showing representative heat map images of mouse peritoneal mast cells showing changes in $[Ca^{2+}]i$, as assayed by Fluo-4 imaging, induced by bath application of anti-IgE (5 µg/ml) or Compound 48/80 (10 µg/ml).
Figure 2C:
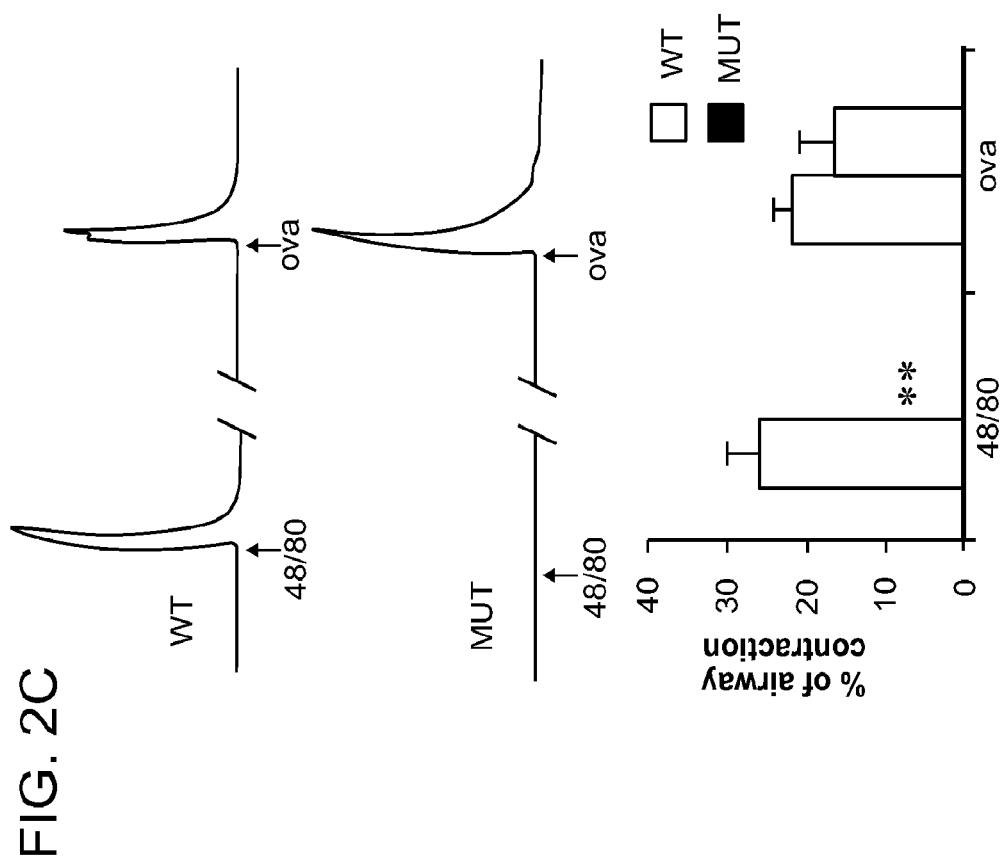
FIG. 2C is a series of graphs.
Figure 2B:
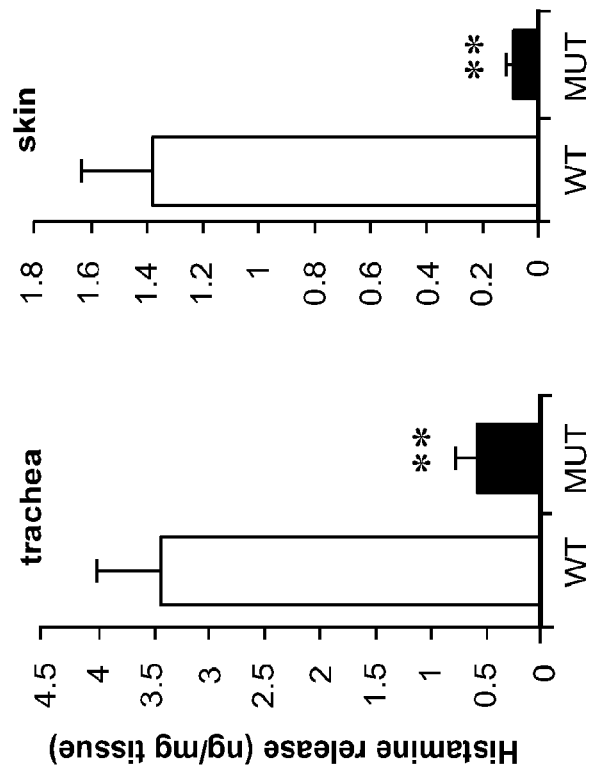
FIG. 2B is a bar graph that shows histamine release into the supernatant from trachea and abdominal skin from WT and MrgprB2$^{MUT}$ mice after exposure to 48/80 (30 µg/ml) for 30 minutes at 37° C. The amount of histamine released into the supernatant was quantified and expressed ng/mg tissue (wet weight). , $p<0.01$ (n=5 for trachea, n=8 for skin).
Figure 2D:
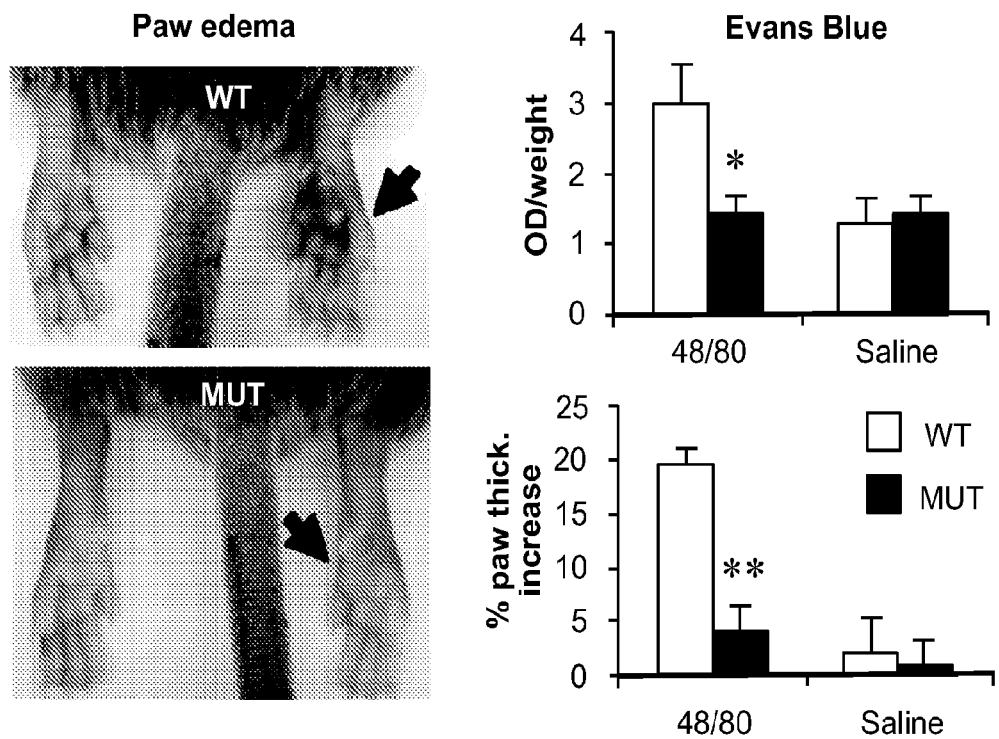
FIG. 2D is a series of photographs and a bar chart showing (left) representative images of Evans Blue extravasation 15 minutes after intraplantar injection of 48/80 (right, arrow, 10 µg/ml, 5 µl in saline) or saline (left).
Figure 2E:
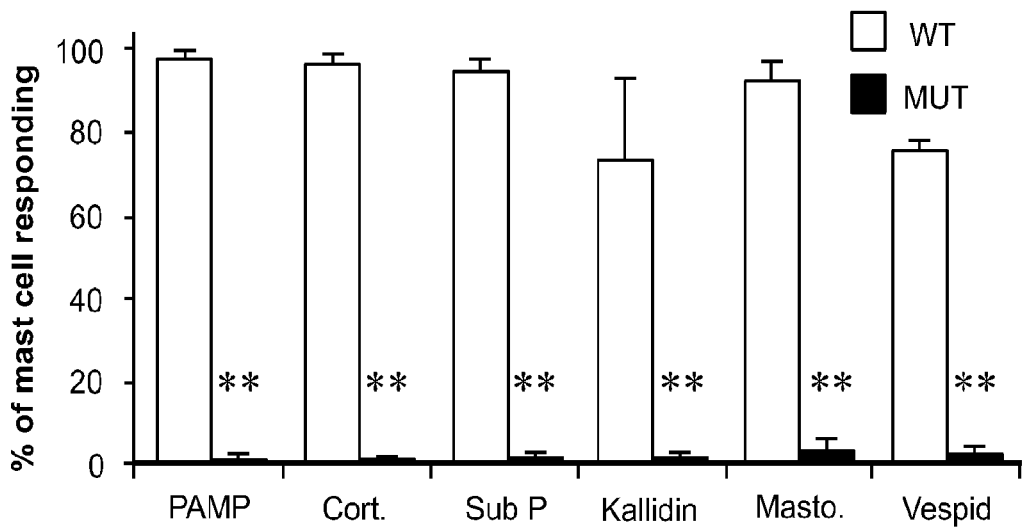
FIG. 2E is a bar chart showing quantification of WT and MrgprB2$^{MUT}$ mast cell responsiveness to MrgprX2 ligands and basic secretagogues, assayed using Fluo-4 imaging. Concentrations of substances (in µM): PAMP(9-20), 20; cortistatin-14 (cort.), 20; Substance P (sub P), 200; kallidin, 200; mastoparan (masto., a component of wasp venom), 20; vespid mastoparan, 20. n=3/genotype; >150 cells counted/secretagogue. Data are presented as mean±standard error of mean (SEM). Two-tailed unpaired Student's t test was used to determine significance in statistical comparisons, and differences were considered significant at $p<0.05$. *, $p<0.05$. **, $p<0.01$ unless noted.
Figure 9A:
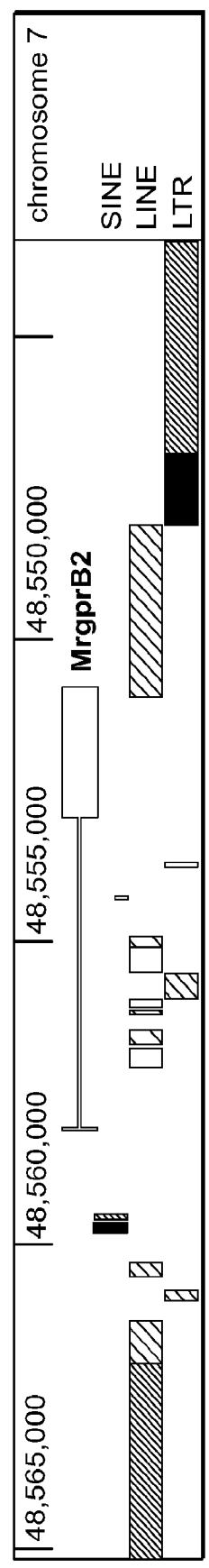
Figures 9B, 9C:
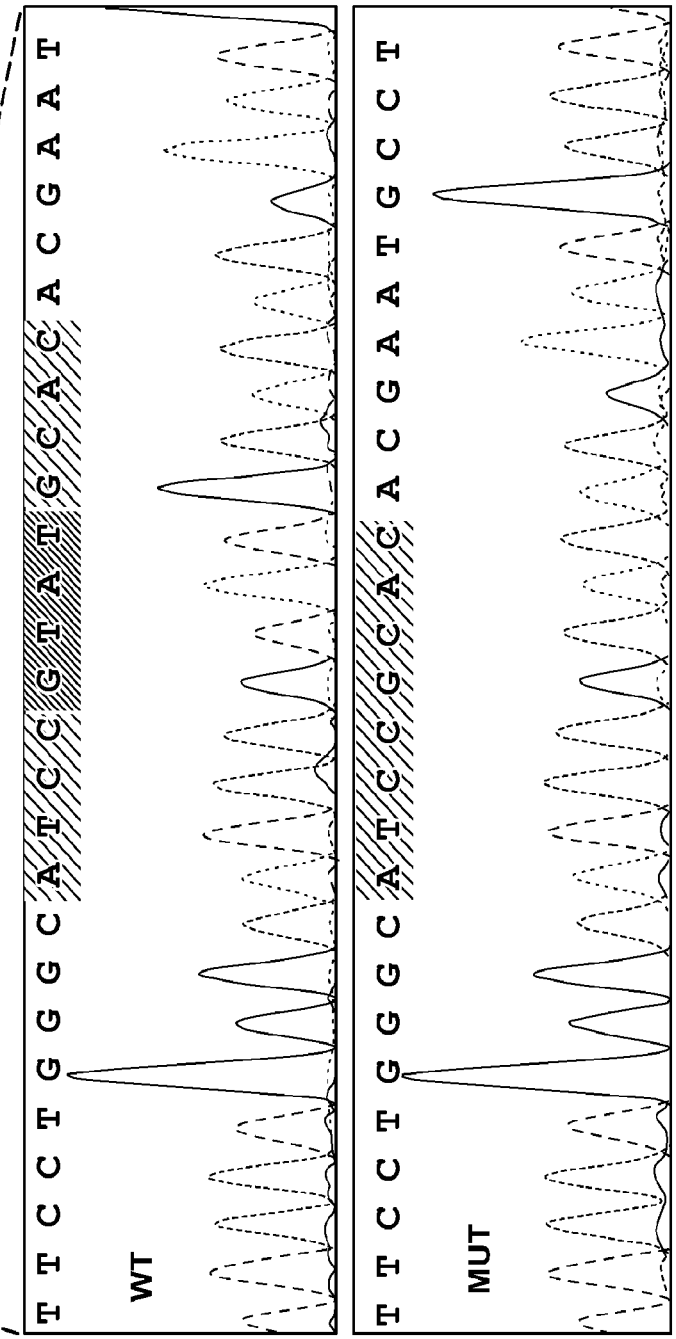
Figure 10A:
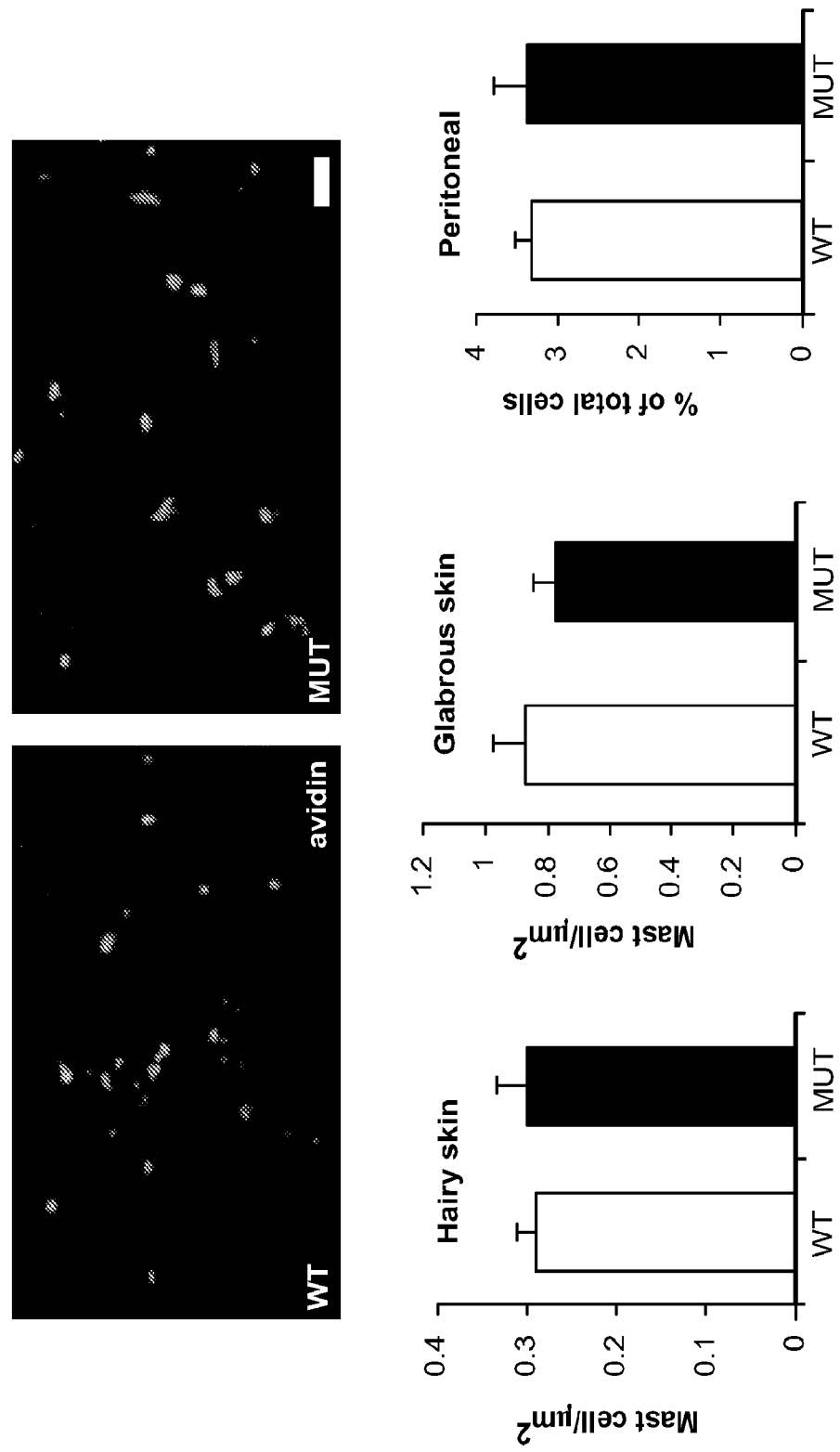
FIG. 10A-FIG. 10B is a series of photomicrographs and bar charts showing that the mast cell numbers and the histamine content of tracheal and skin tissue was not different between wild type and MrgprB2$^{MUT}$ animals.
Figure 10B:
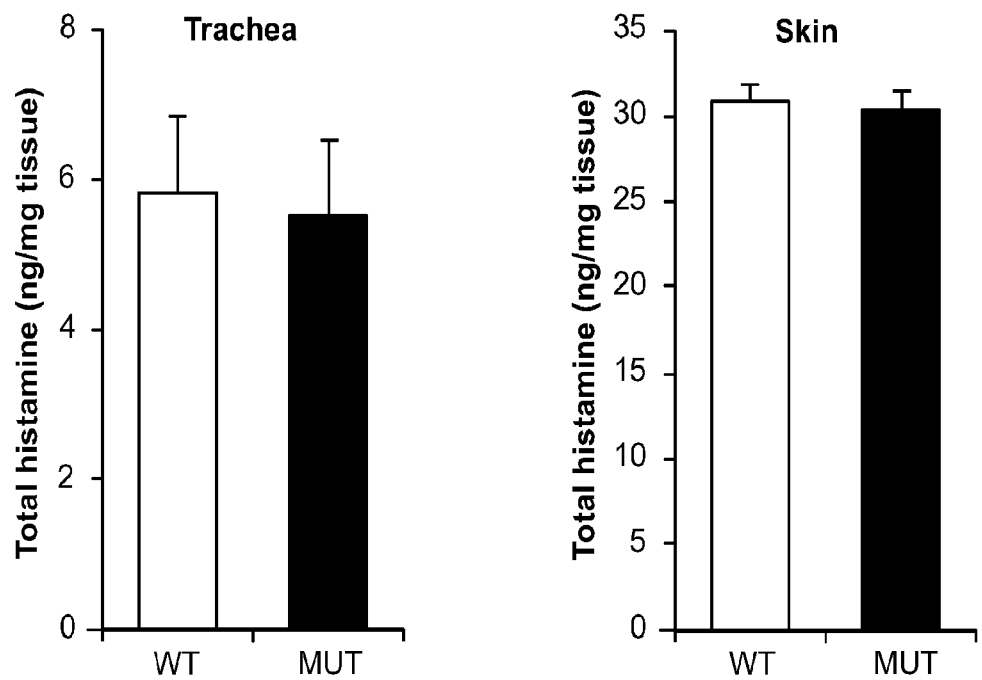
Figure 11A:
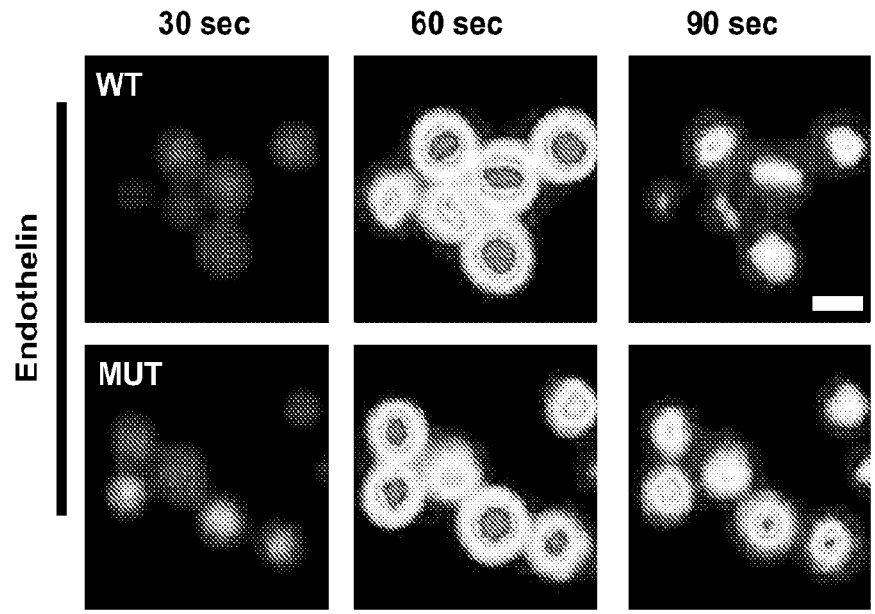
FIG. 11A, FIG. 11B, and FIG. 11C are a series of photomicrographs, a line graph, and a bar chart, respectively, which show endothelin acting through the ETA GPCR1 induced comparable activation in MrgprB2$^{MUT}$ and wild-type mast cells.
Figure 11B:
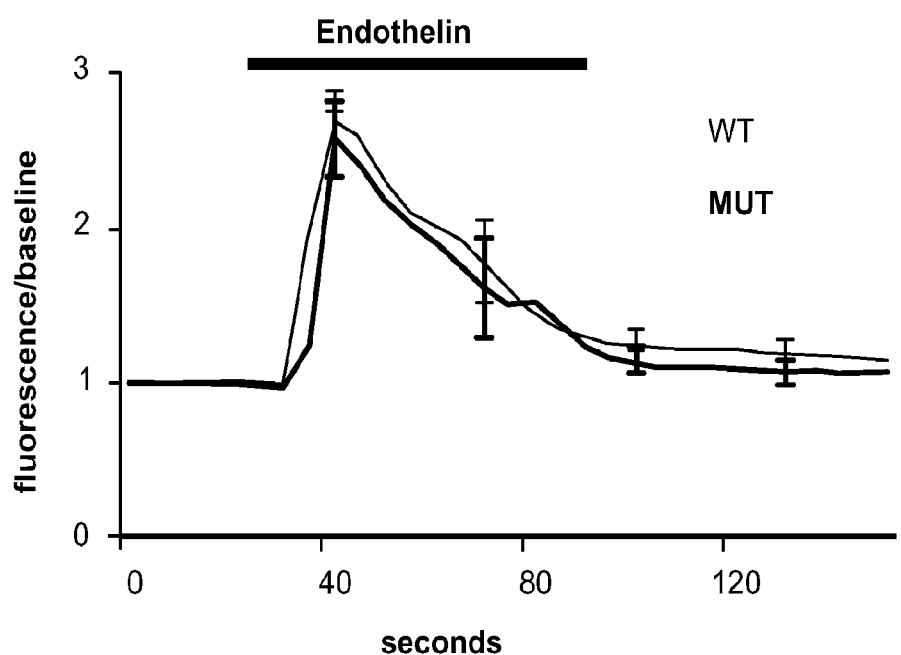
Figure 11C:
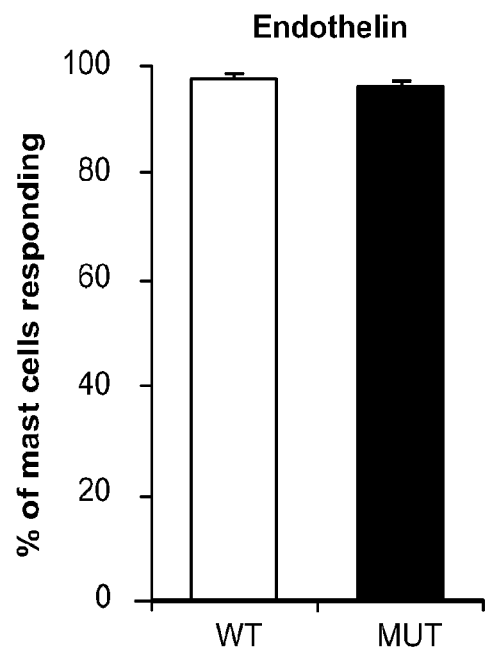
Figures 1, 13A:
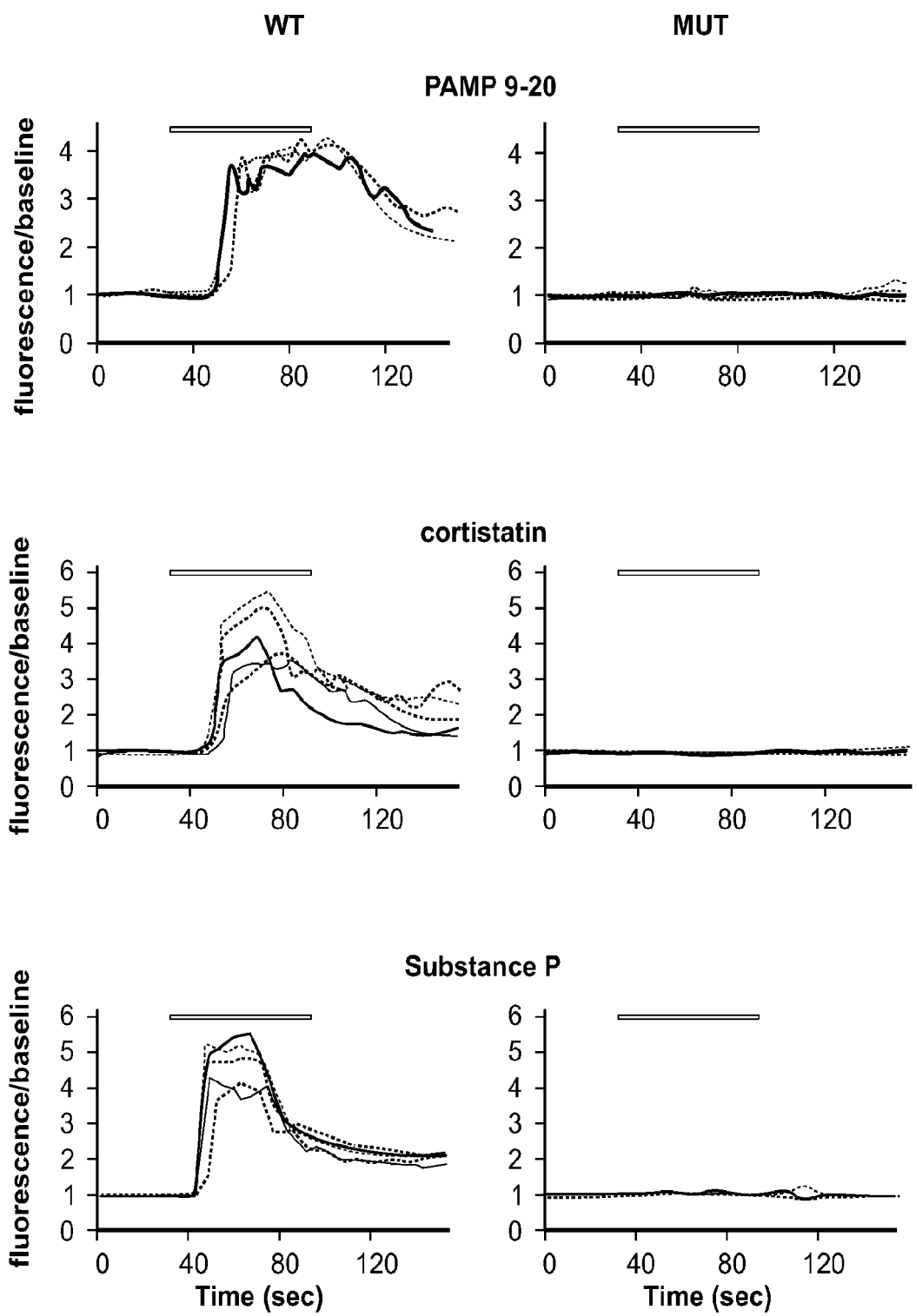
FIG. 13A, FIG. 13B, FIG. 13C, FIG. 13D, and FIG. 13E show that MrgprB2$^{MUT}$ mast cells are unresponsive to basic secretagogues and various therapeutic drugs.
Figures 2, 13A:
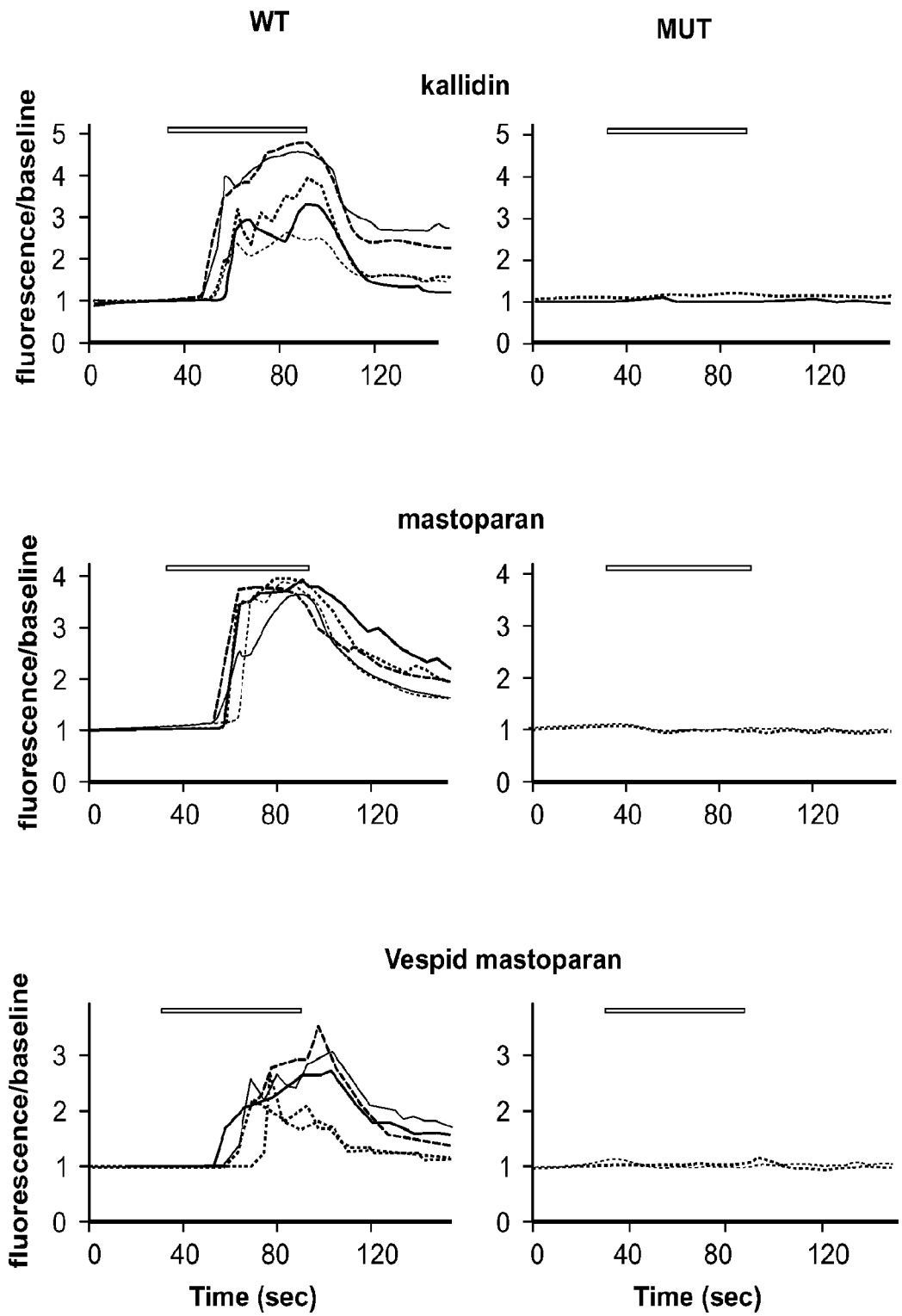

Next, it was determined whether MrgprB2 is the basic secretagogue receptor in mouse mast cells. The MrgprB2 genomic locus contains too much repetitive sequence to permit gene targeting through homologous recombination (FIG. 9A). Therefore, a zinc finger nuclease-based strategy was used to generate a mouse line with a 4 base pair deletion in the MrgprB2 coding region (MrgprB2$^{MUT}$ mice), resulting in a frameshift mutation and early termination shortly after the first transmembrane domain (FIG. 9B, FIG. 9C, and FIG. 9D). The mutation was stable and inheritable (FIG. 9C), so MrgprB2$^{MUT}$ was regarded as a functional null. Mast cell numbers were comparable in tissues of wild-type (WT) and MrgprB2$^{MUT}$ mice, indicating that MrgprB2 is not essential for mast cell survival or targeting to tissue (FIG. 10A). Responsiveness of peritoneal mast cells to anti-IgE antibodies (FIG. 2A) and endothelin (FIG. 11A, FIG. 11B, and FIG. 11C) also was comparable, demonstrating that MrgprB2 mutation does not globally impair IgE or GPCR-mediated mast cell signaling. However, 48/80-induced mast cell activation (FIG. 2A) and tissue histamine release essentially was abolished in mutant mast cells (FIG. 2B and FIG. 10B). Further, 48/80-evoked tracheal contraction (FIG. 2C) and hindpaw inflammation (extravasation and swelling; FIG. 2D) were almost completely absent in an MrgprB2$^{MUT}$ background, while antigen (FIG. 2C) and anti-IgE evoked responses (FIG. 12A and FIG. 12B) were comparable to WT mice. Finally, four additional basic secretagogues, as well as MrgprX2 agonists PAMP (9-20) and cortistatin (Robas, N., Mead, E. & Fidock, M. MrgX2 is a high potency cortistatin receptor expressed in dorsal root ganglion. *The Journal of biological chemistry* 278, 44400-44404, doi:10.1074/jbc.M302456200 (2003)), strongly activated WT but not MrgprB2$^{MUT}$ mast cells (FIG. 2E; FIG. 13A). HEK293 cells expressing MrgprB2 or MrgprX2 (MrgprX2-HEK) also responded to these secretagogues (FIG. 6A and FIG. 6B). Taken together, it was concluded that MrgprB2 is the mouse mast cell basic secretagogue receptor. It is likely that the list of small, basic peptides that activate MrgprB2 is greater than the number in this study; indeed, dozens of such peptides have been shown to activate mast cells (Lagunoff, D., Martin, T. W. & Read, G. Agents that release histamine from mast cells. *Annual review of pharmacology and toxicology* 23, 331-351, doi:10.1146/annurev.pa.23.040183.001555 (1983); Ferry, X., Brehin, S., Kamel, R. & Landry, Y. G protein-dependent activation of mast cell by peptides and basic secretagogues. *Peptides* 23, 1507-1515 (2002); Mousli, M., Hugh, T. E., Landry, Y. & Bronner, C. Peptidergic pathway in human skin and rat peritoneal mast cell activation. *Immunopharmacology* 27, 1-11 (1994); Pundir, P. & Kulka, M. The role of G protein-coupled receptors in mast cell activation by antimicrobial peptides: is there a connection? *Immunology and cell biology* 88, 632-640, doi: 10.1038/icb.2010.27 (2010)). Notably, human MrgprX2 is much more sensitive to Substance P than mouse MrgprB2 (FIG. 6C), suggesting a potential species-specific role for Substance P in mast cell signaling.

Given that micromolar concentrations of these peptides are required for MrgprB2 activation, it is unclear where such a signaling event might occur. However, mast cells are present in organs like the pancreas and adrenal glands that secrete large amounts of small, cationic peptides, and it is conceivable that concentrations close to the sites of release reach these levels. Described herein are high-affinity endogenous ligand(s) for MrgprB2. Identification of endogenous MrgprB2 and MrgprX2 ligands contributes significantly to understanding how mast cells interact with other cell types in disease states.

Example 4: MrgprB2 Mediates Mast Cell Responsiveness and Side Effects of Peptidergic Therapeutic Drugs The critical role of mast cells in allergic and pseudo-allergic (i.e., IgE-independent) reactions suggested a need for experiments demonstrating whether MrgprX2 is a factor in these events. Drug-induced reactions were addressed because many therapeutic drugs are cationic. Up to 15% of drug-induced adverse reactions appear to be allergic in nature; however, many are not well-correlated with IgE antibody titer, indicating that antibody-independent, or pseudo-allergic, mechanisms participate (Hausmann, O., Schnyder, B. & Pichler, W. J. Etiology and pathogenesis of adverse drug reactions. *Chemical immunology and allergy* 97, 32-46, doi:10.1159/000335614 (2012)).

Figure 3A:
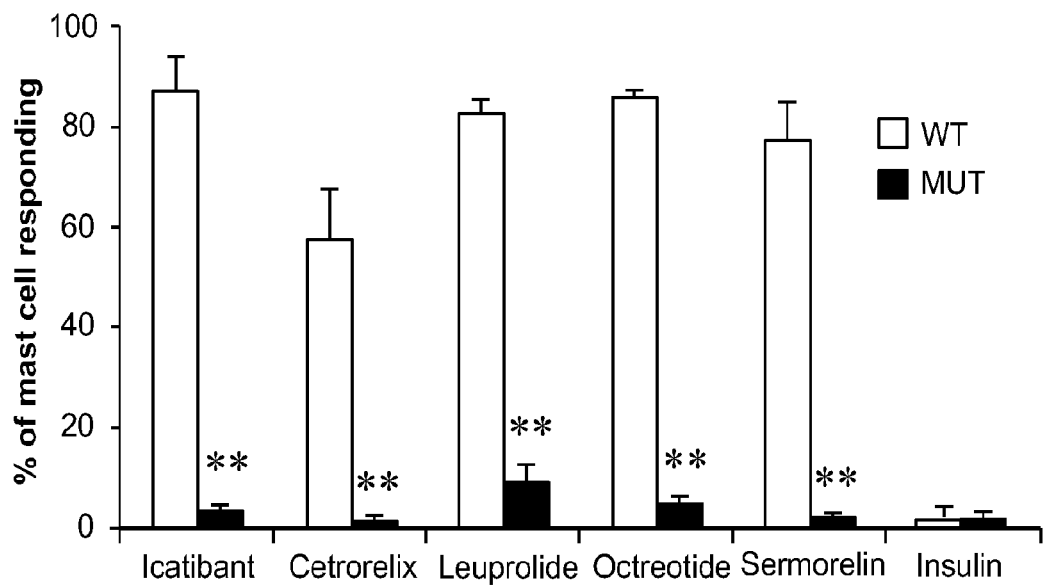
FIG. 3A is a bar chart showing that MrgprB2 mediates mast cell responsiveness and side effects of peptidergic therapeutic drugs.
Figure 3B:
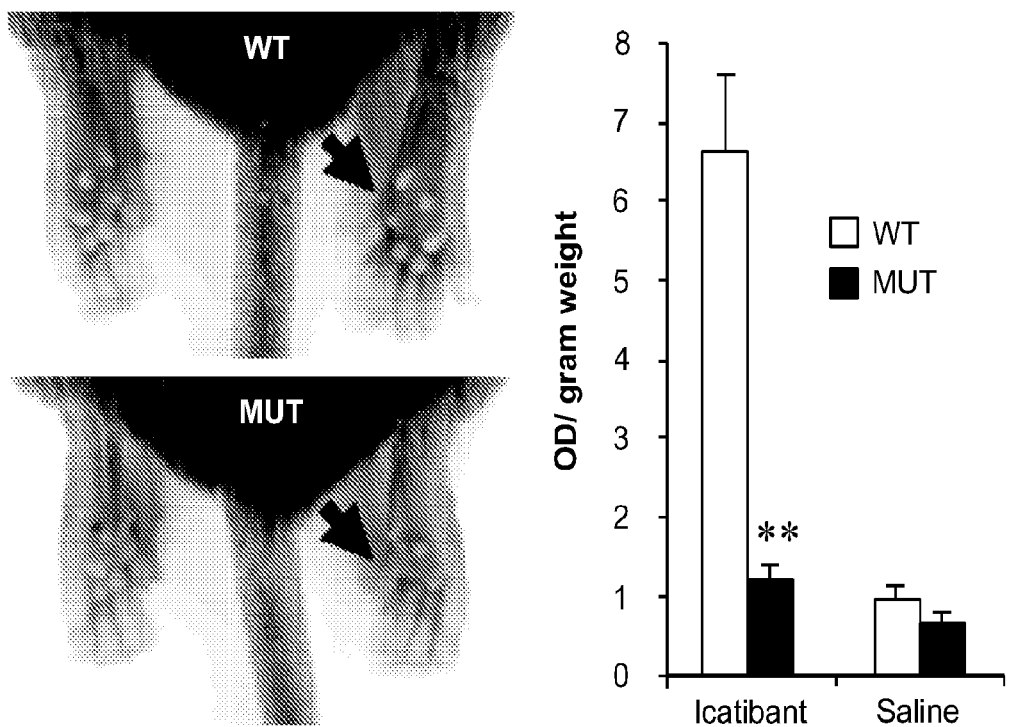
FIG. 3B (left) shows representative images of Evans Blue extravasation 15 minutes after intraplantar injection of icatibant (right, arrow, 10 mg/ml, 5 µl in saline) or saline (left).
Figure 3C:
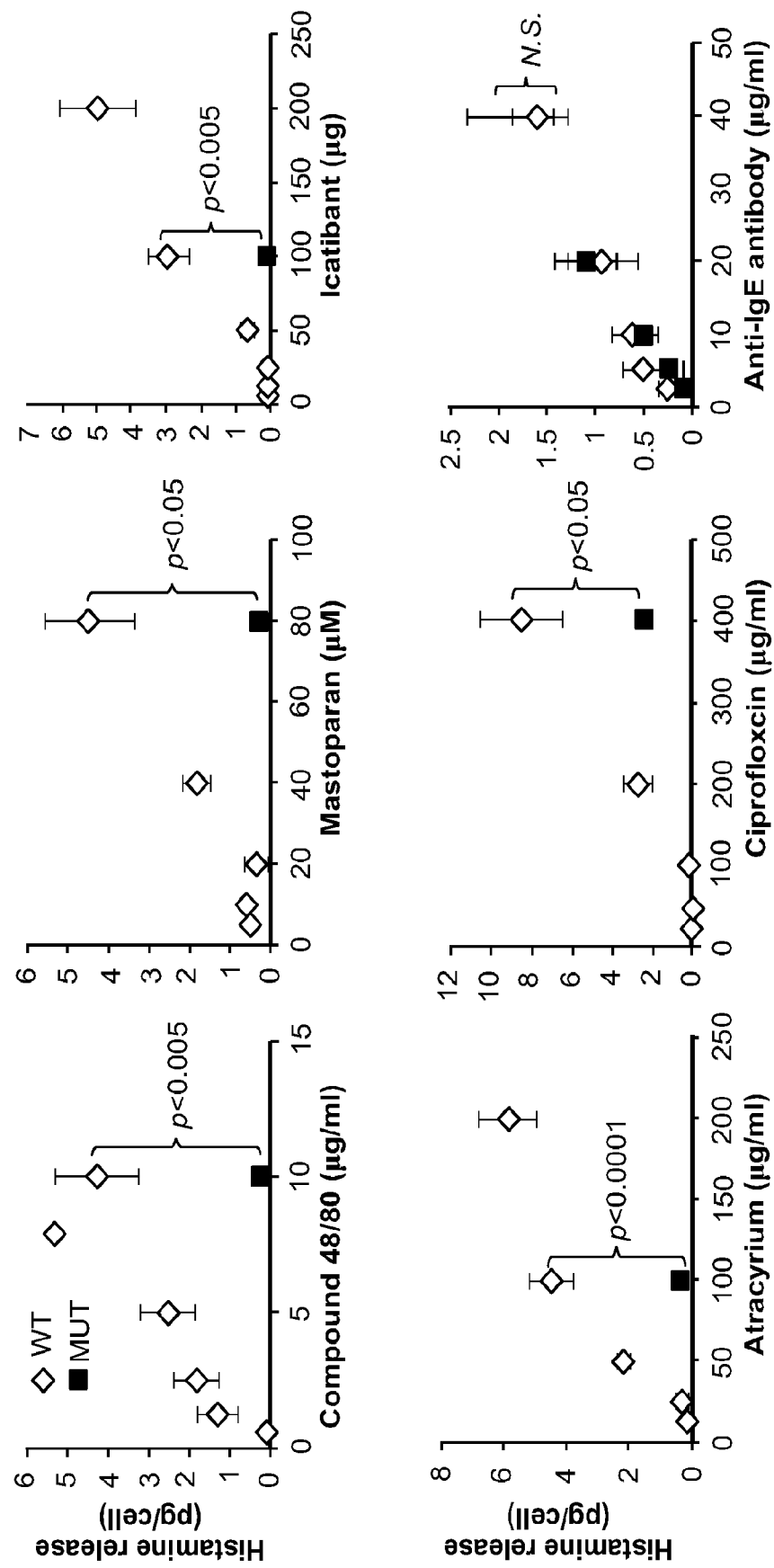
FIG. 3C is a series of dot plots showing total histamine release from WT (red diamonds) and MrgprB2$^{MUT}$ (black squares) mice after incubation with named substances. No significant difference between WT and MrgprB2$^{MUT}$ cells was found at any dose of anti-IgE antibody. Experiments were repeated >3 times. Data are presented as mean±SEM. Two-tailed unpaired Student's t test: *, $p<0.05$. **, $p<0.01$.
Figure 13B:
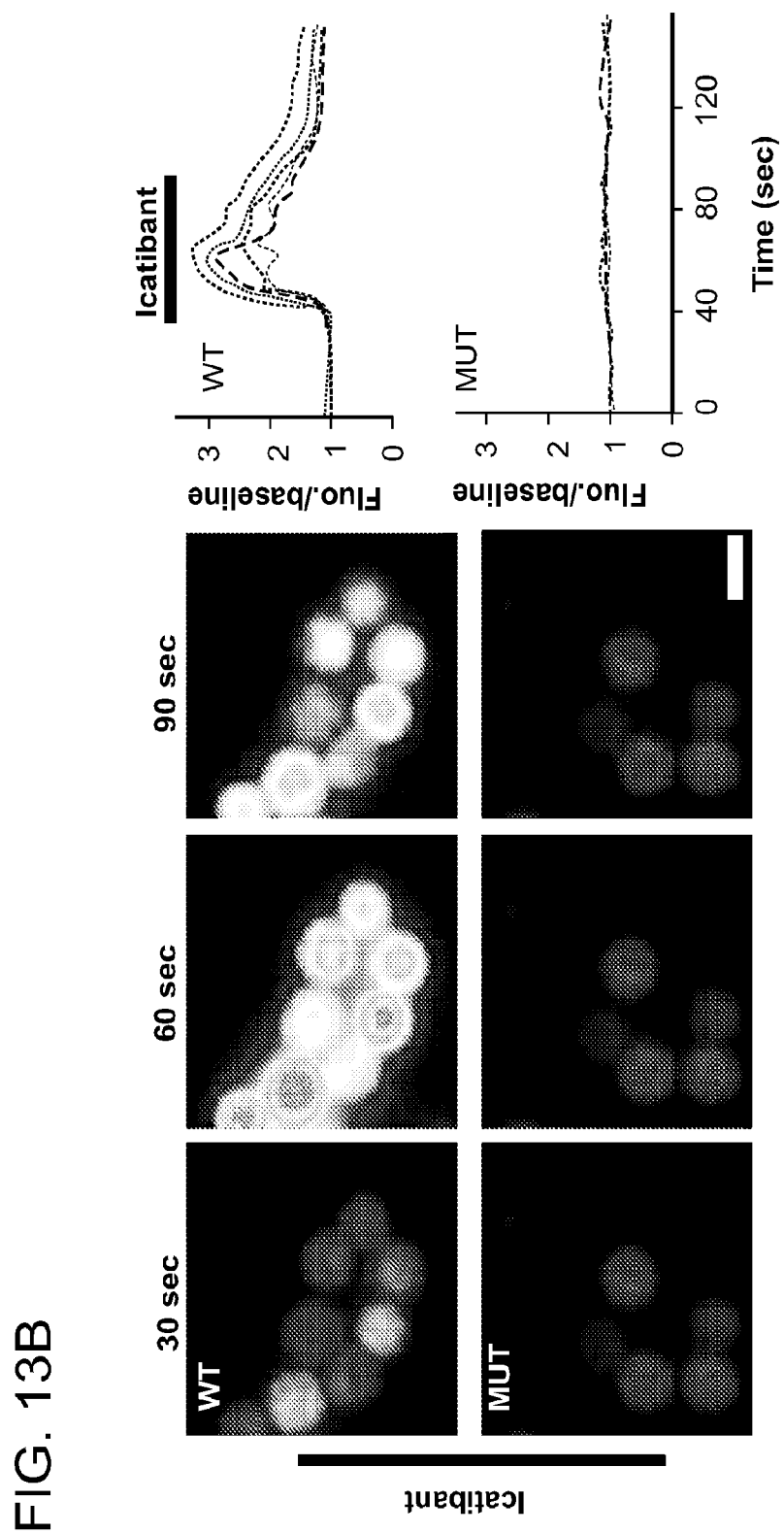
Figure 13C:
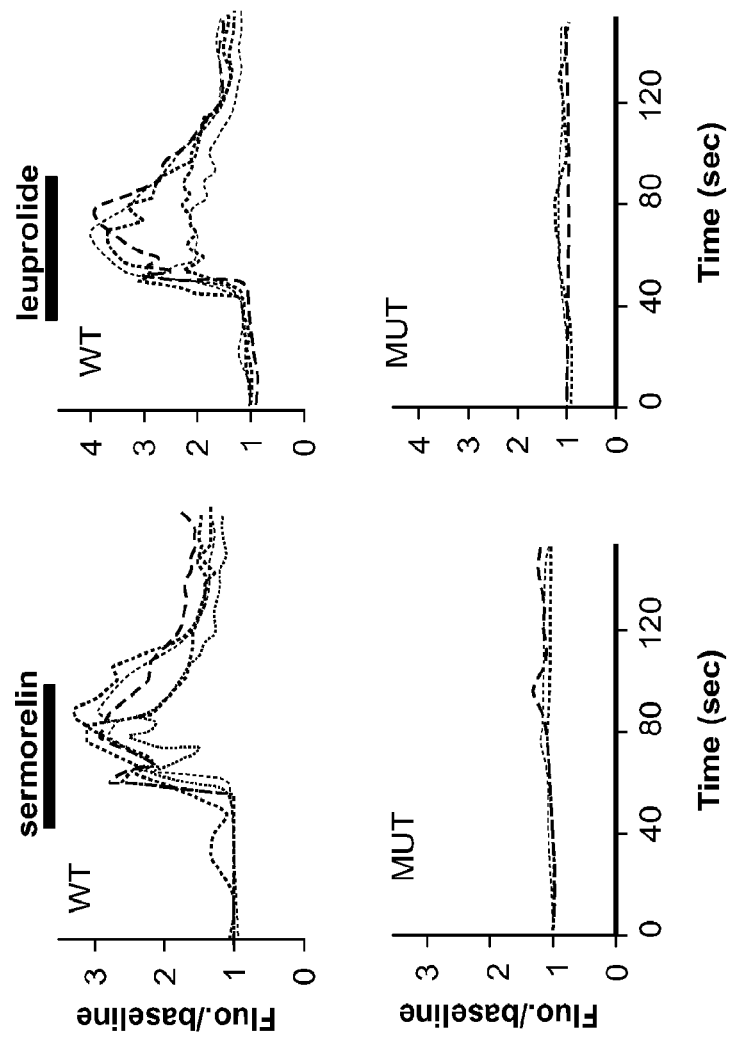

First, peptidergic drugs were analyzed because most are introduced subcutaneously or intramuscularly at millimolar concentrations (FIG. 15), high enough for cationic peptides to activate mast cells. The most frequent allergic-type response described in FDA labels of these drugs is an injection-site reaction (ISR), a local swelling and/or flare of variable size which can be accompanied by pain or pruritus. In a survey of FDA-approved peptidergic drugs, the vast majority associated with ISRs are cationic (FIG. 15). Representative members of all common, commercially available classes of these cationic drugs activated mast cells in an MrgprB2-dependent manner, while the innocuous protein insulin had no effect (FIG. 3A, FIG. 13B, and FIG. 13C). Consistently, all of these peptides except insulin activate both MrgprB2-HEK and MrgprX2-HEK cells (FIG. 6A, FIG. 6B, and FIG. 6C). The drug icatibant was chosen for further study because it induces ISRs nearly in every patient (Lumry, W. R. et al. Randomized placebo-controlled trial of the bradykinin B(2) receptor antagonist icatibant for the treatment of acute attacks of hereditary angioedema: the FAST-3 trial. *Annals of allergy, asthma & immunology: official publication of the American College of Allergy, Asthma, & Immunology* 107, 529-537, (2011)). Icatibant at the clinical concentration induced extensive extravasation and swelling, similar to human ISRs, in WT mice but not in MrgprB2$^{MUT}$ mice (FIG. 3B). Mice pretreated with the mast cell stabilizer ketotifen also showed no inflammation (without ketotifen: 40.7±2.1% increase in paw thickness; with ketotifen: 3.1±0.6% increase; n=4 each; p=2.2e-6), strongly indicating that mast cells mediated the inflammation. Furthermore, icatibant (as well as positive controls 48/80 and mastoparan) induced histamine release from WT peritoneal mast cells, while MrgprB2$^{MUT}$ mast cells released substantially less (FIG. 3C). However, IgE-mediated histamine release was unaffected by MrgprB2 deletion (FIG. 3C). These data anticipate that drug-induced ISRs may be alleviated by targeting MrgprX2 or by using peptides with less potent MrgprX2 agonist properties.

Figure 4B:
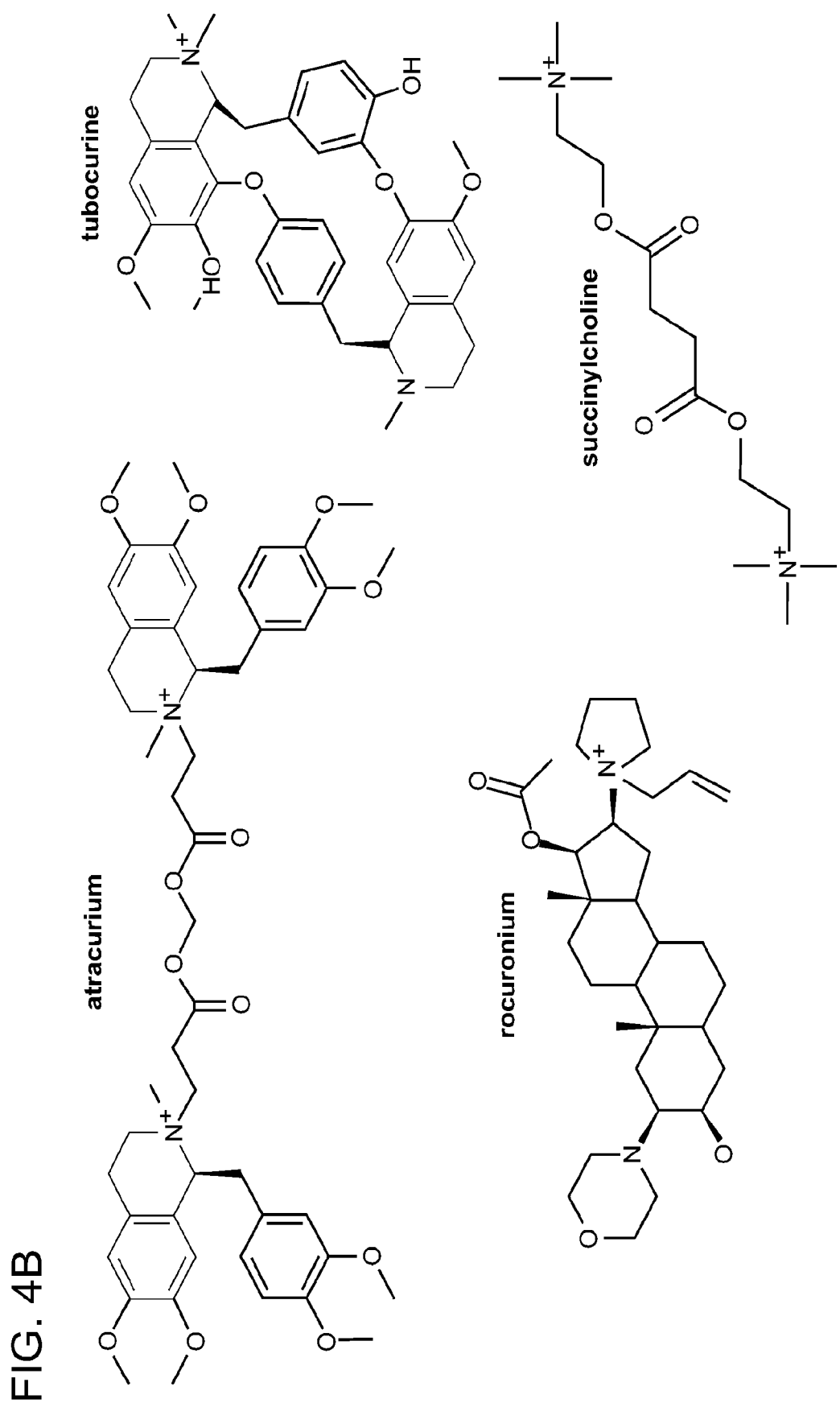
FIG. 4B is a series of structures of representative members of all NMBD classes. THIQ motifs are highlighted in blue. Note that only succinylcholine lacks a bulky hydrophobic group.
Figure 4C:
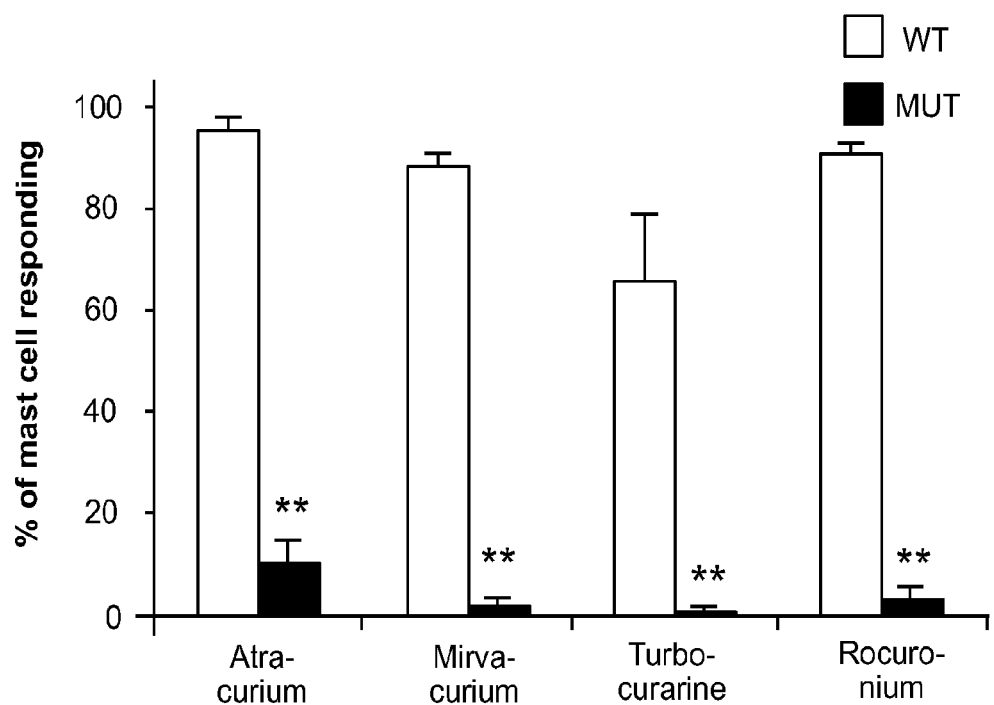
FIG. 4C is a bar chart showing that MrgprB2 mediates mast cell responsiveness and side effects of small molecule therapeutic drugs.
Figure 4D:
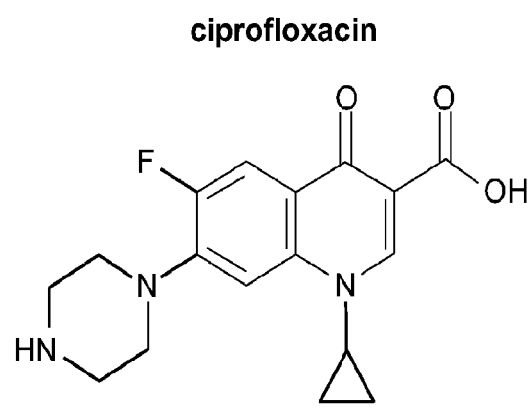
FIG. 4D is a depiction of the structure of ciprofloxacin, with the motif common to all fluoroquinolones highlighted in blue. Note nitrogens close to the quinolone motifs.
Figure 4E:
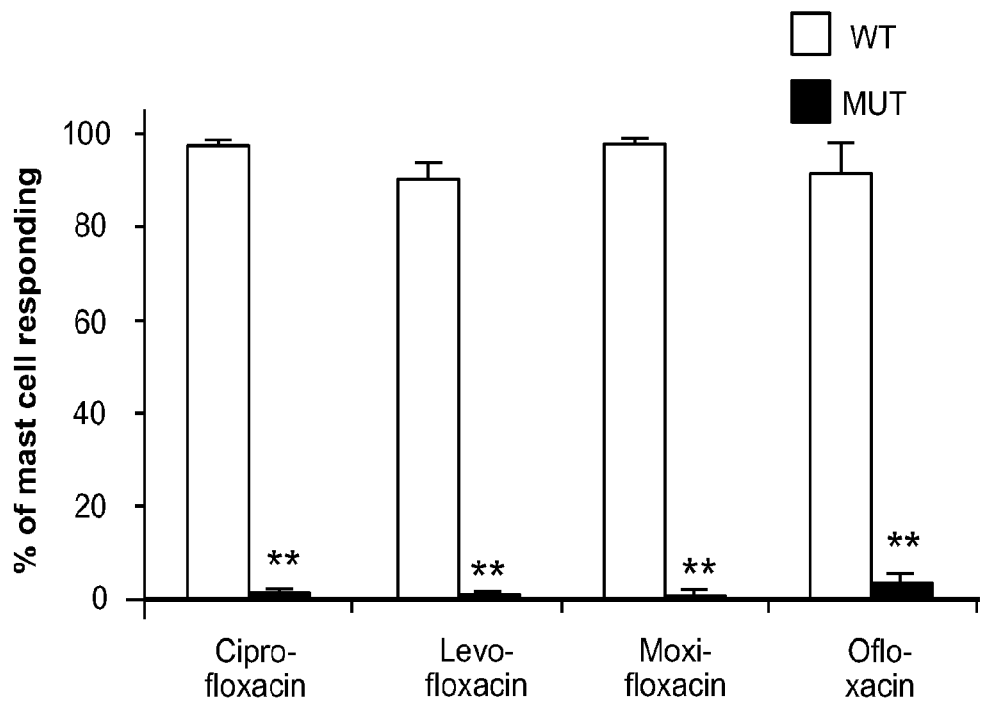
FIG. 4E is a bar chart showing the percentage of responding cells from WT and MrgprB2$^{MUT}$ peritoneal mast cells after fluoroquinolone application, assayed using Fluo-4 imaging. Concentrations of drugs (in µg/ml): ciprofloxacin, 200; levofloxacin, 500; moxifloxacin, 160; ofloxacin, 400. n=3 mice/genotype; >150 cells counted/substance.
Figure 4F:
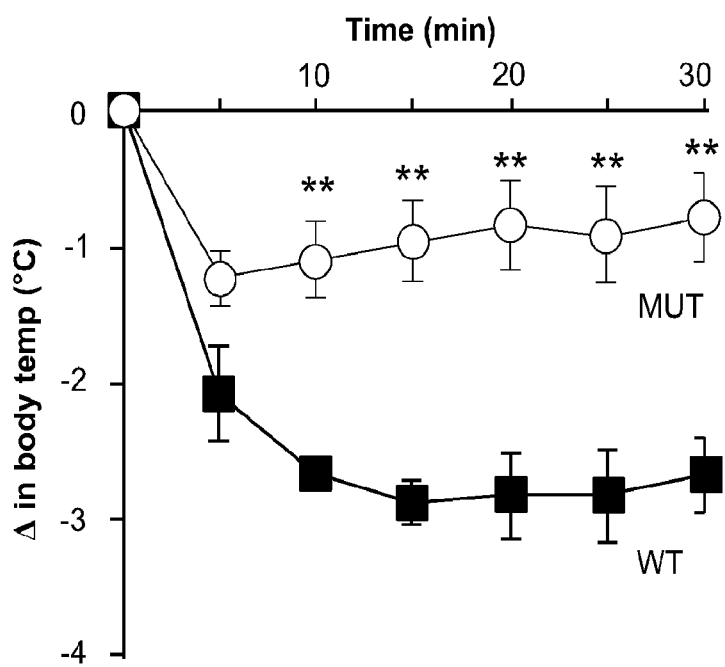
FIG. 4F is a line graph showing changes in body temperature after intravenous injection of ciprofloxacin (1.5 mg in 125 µl saline) at time 0. n=4 mice/genotype. Data are presented as mean±SEM. Two-tailed unpaired Student's t test: *, $p<0.05$. **, $p<0.01$.
Figure 13D:
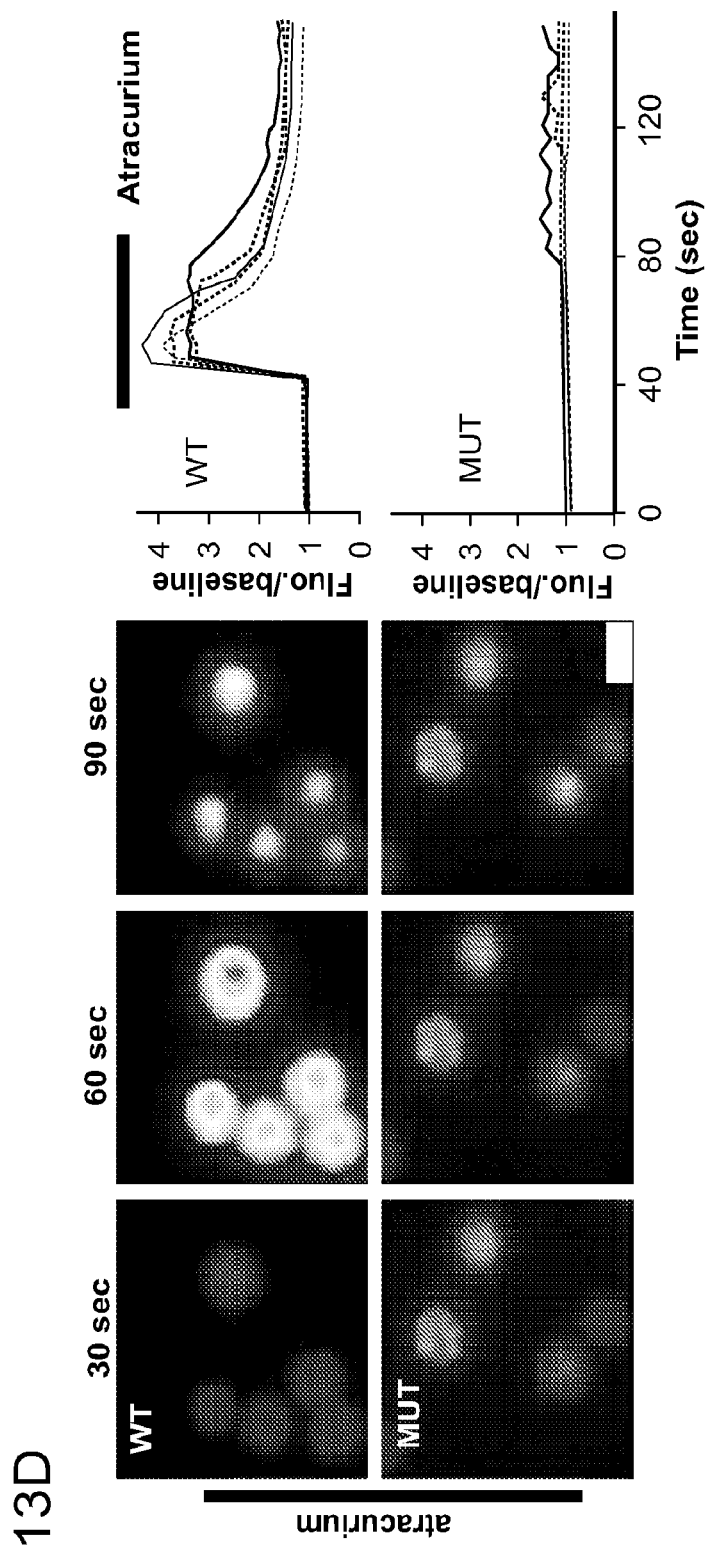
Figure 13E:
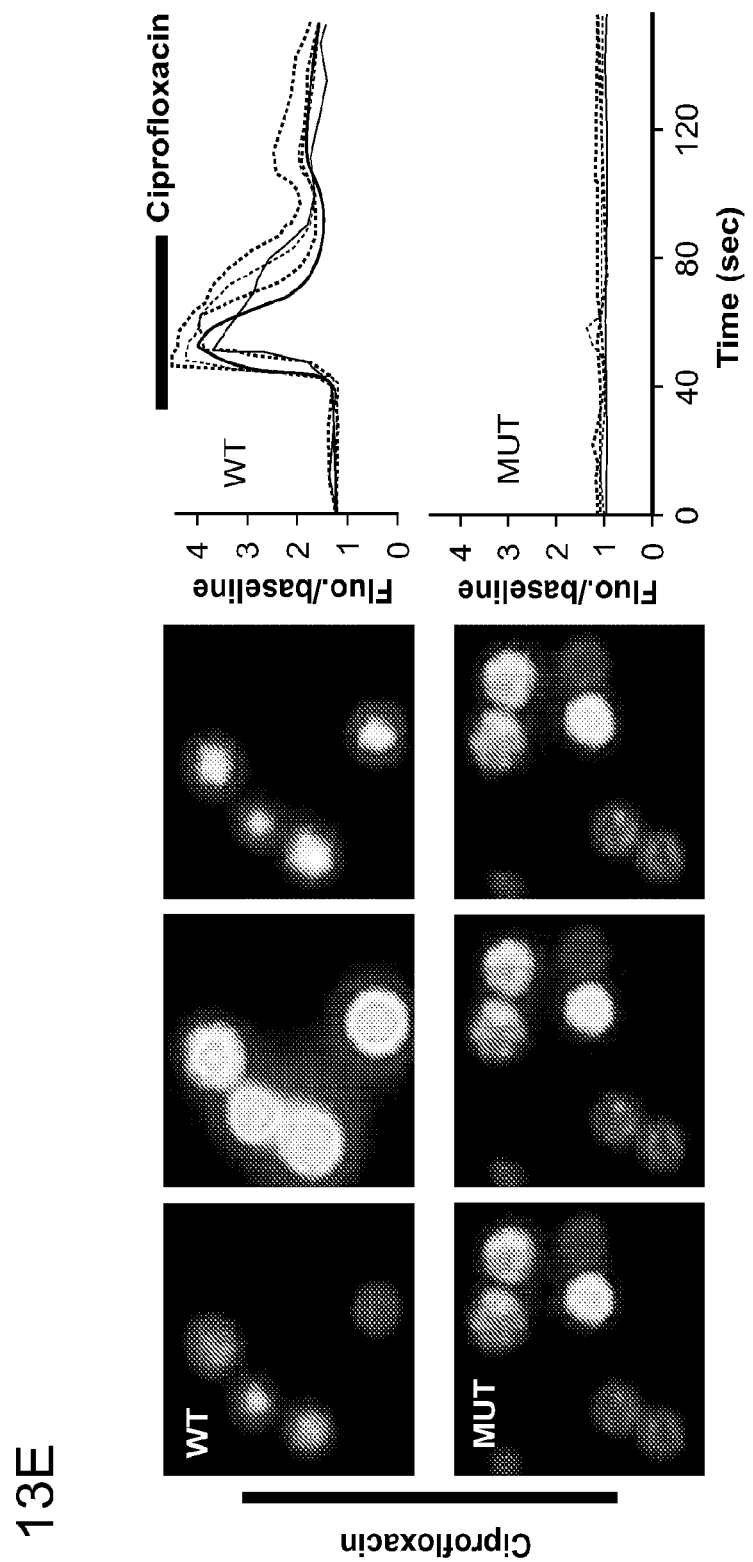

Example 5: MrgprB2 Mediates Mast Cell Responsiveness and Side Effects of Small Molecule Therapeutic Drugs Next, the possibility that MrgprB2 mediates pseudo-allergic reactions induced by small molecules was explored. The focus was on intravenously applied drugs because they often are administered rapidly and in high doses, and thus are more likely to achieve high blood concentrations and rapid tissue distribution than drugs administered through other routes. Symptoms of pseudo-allergic reactions after intravenous administration, which at the most severe are called anaphylactoid, include skin flushing or rash, changes in blood pressure or heart rate, and bronchospasms (Nel, L. & Eren, E. Peri-operative anaphylaxis. *British journal of clinical pharmacology* 71, 647-658, doi:10.1111/j.1365-2125.2011.03913.x (2011)). The initial search was based on the structure of 48/80. While the structure-function relationship of 48/80 as an MrgprX2 agonist was unknown, a cyclized variant containing a tetrahydroisoquinoline (THIQ) motif (FIG. 4A) is seven times more potent than 48/80 as a mast cell degranulator (Read, G. W. Compound 48-80. Structure-activity relations and poly-THIQ, a new, more potent analog. *Journal of medicinal chemistry* 16, 1292-1295 (1973)). A search of FDA-approved drugs containing a THIQ recovered members of the nicotinic receptor antagonist non-steroidal neuromuscular blocking drugs (NMBDs), including tubocurarine and atracurium (FIG. 4B). NMBDs are used routinely in surgery to reduce unwanted muscle movement and allow intratracheal intubation for mechanical ventilation. Intriguingly, NMBDs alone are responsible for nearly 60% of allergic reactions in a surgical setting (Mertes, P. M., Alla, F., Trechot, P., Auroy, Y. & Jougla, E. Anaphylaxis during anesthesia in France: an 8-year national survey. *J Allergy Clin Immunol* 128, 366-373 (2011)), and all except succinylcholine induce histamine release in humans (Koppert, W. et al. Different patterns of mast cell activation by muscle relaxants in human skin. *Anesthesiology* 95, 659-667 (2001)). As shown in FIG. 16, members of all NMBD families except succinylcholine activated mast cells in an MrgprB2-dependent manner at concentrations as low as 0.5% of the clinical injection concentration (FIG. 4C and FIG. 13D). Interestingly, rocuronium does not contain a THIQ but has a bulky hydrophobic group with a charged nitrogen within several angstroms (FIG. 4B), reminiscent of 48/80. Therefore, a search was performed using modifications of the THIQ motif and the 48/80 structure, including changes in cyclization and position of the positive or polar nitrogen, limiting the assay to intravenous drugs at high injection concentrations. The fluoroquinolone family of antibiotics was identified as having a similar motif (FIG. 4D). Like NMBDs, these are associated with allergic-type reactions (Kelesidis, T., Fleisher, J. & Tsiodras, S. Anaphylactoid reaction considered ciprofloxacin related: a case report and literature review. *Clin Ther* 32, 515-526 (2010); Blanca-Lopez, N. et al. Hypersensitivity reactions to fluoroquinolones: analysis of the factors involved. *Clin Exp Allergy* 43, 560-567 (2013)) and can activate mast cells (Mori, K., Maru, C. & Takasuna, K. Characterization of histamine release induced by fluoroquinolone antibacterial agents in-vivo and in-vitro. *The Journal of pharmacy and pharmacology* 52, 577-584 (2000); Mori, K., Maru, C., Takasuna, K. & Furuhama, K. Mechanism of histamine release induced by levofloxacin, a fluoroquinolone antibacterial agent. *European journal of pharmacology* 394, 51-55 (2000)). The four members approved for intravenous use activated MrgprB2-HEK and MrgprX2-HEK cells (FIG. 6A, FIG. 6B, and FIG. 6C), and mast cells in an MrgprB2-dependent manner (FIG. 4E; FIG. 13C). Correspondingly, atracurium and ciprofloxacin induced histamine release in WT peritoneal mast cells and substantially less in MrgprB2$^{MUT}$ mast cells (FIG. 3C). Ciprofloxacin was selected for in vivo tests of anaphylaxis, which in mice is measured most often by a drop in body temperature, likely due to changes in blood pressure and peripheral vasodilation (Doyle, E., Trosien, J. & Metz, M. Protocols for the induction and evaluation of systemic anaphylaxis in mice. *Methods in molecular biology* 1032, 133-138, doi:10.1007/978-1-62703-496-8_10 (2013)). Rodents nearly are immune to histamine toxicity at a systemic level, contrary to other experimental organisms (Halpern, B. N. & Wood, D. R. The action of promethazine (phenergan) in protecting mice against death due to histamine. *British journal of pharmacology and chemotherapy* 5, 510-516 (1950)), but can be rendered sensitive to mast cell activators and secreted products by pretreatment with beta-adrenergic blockers (Bergman, R. K. & Munoz, J. Efficacy of beta-adrenergic blocking agents in inducing histamine sensitivity in mice. *Nature* 217, 1173-1174 (1968); Matsumura, Y., Tan, E. M. & Vaughan, J. H. Hypersensitivity to histamine and systemic anaphylaxis in mice with pharmacologic beta adrenergic blockade: protection by nucleotides. *J Allergy Clin Immunol* 58, 387-394 (1976)). Under these conditions, a high dose of ciprofloxacin induced a rapid drop in body temperature that was very slow to recover, while MrgprB2$^{MUT}$ mice showed a much smaller drop that recovered quickly (FIG. 4F). These results establish that mast cell activation through MrgprB2 is an off-target effect of fluoroquinolones and other drugs, and corresponding MrgprX2 activation in humans might underlie much of the pseudo-allergic responses seen with these drugs.

Example 6: Drugs Associated with Pseudo-Allergies Activate Human Mast Cells Through MrgprX2

Figures 1, 14A:
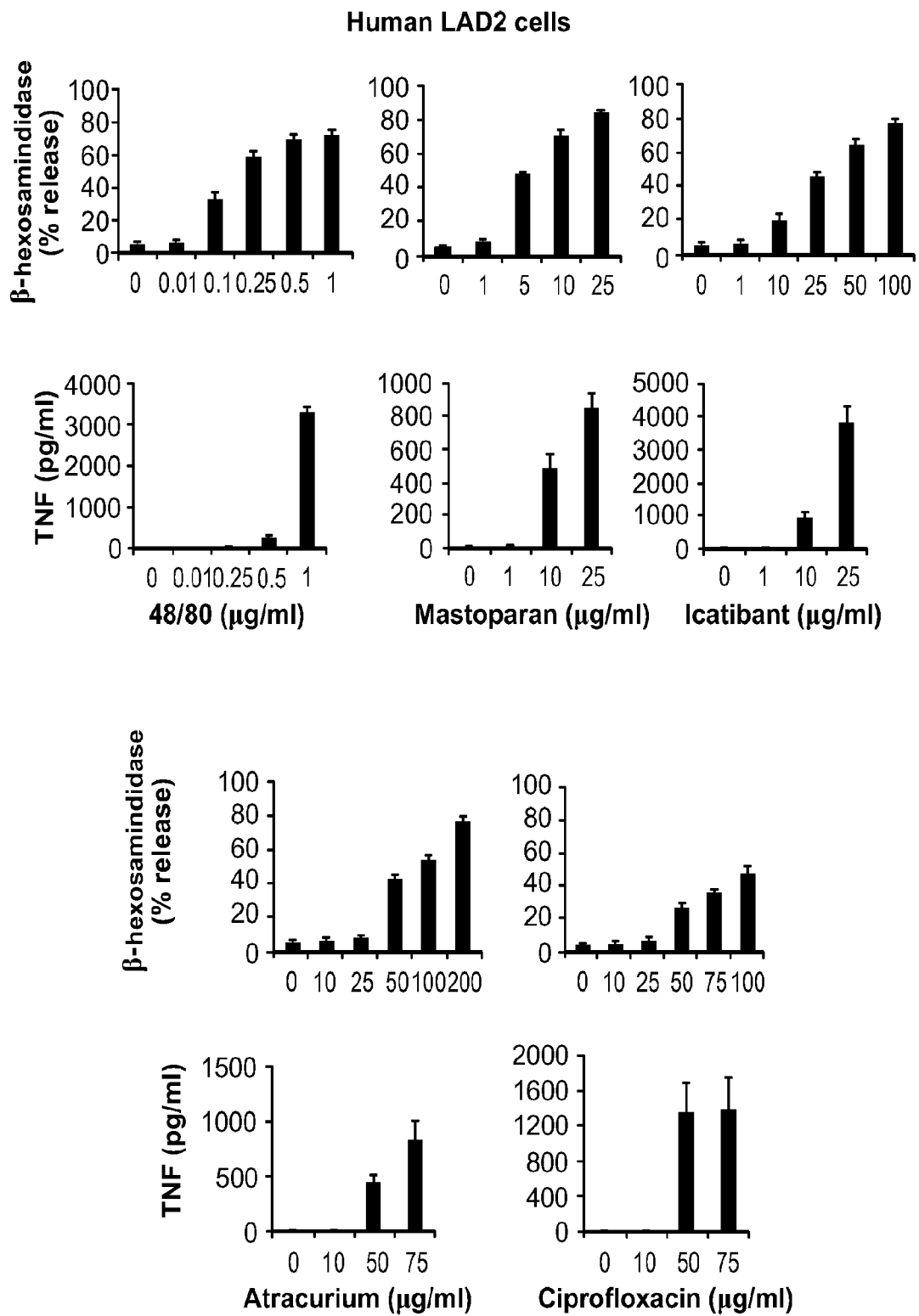
FIG. 14A and FIG. 14B is a series of bar charts showing that human mast cells are activated by basic secretagogues and drugs associated with pseudo-allergic reactions in an MrgprX2-dependent manner FIG. 14A human LAD2 mast cells treated with different concentrations of compound 48/80, mastoparan, icatibant, atracurium, and ciprofloxacin. The activation of mast cells in response to these substances was characterized by the release of β-hexosaminidase, TNF, PGD2, and histamine. In addition, 0.1 µg/ml streptavidin stimulation of biotin-conjugated human IgE sensitized LAD2 cells caused a robust release of β-hexosaminidase (71.3±1.8% release), compared to untreated cells (4.1±0.3% release). Group data are expressed as mean±standard error of the mean.
Figures 2, 14A:
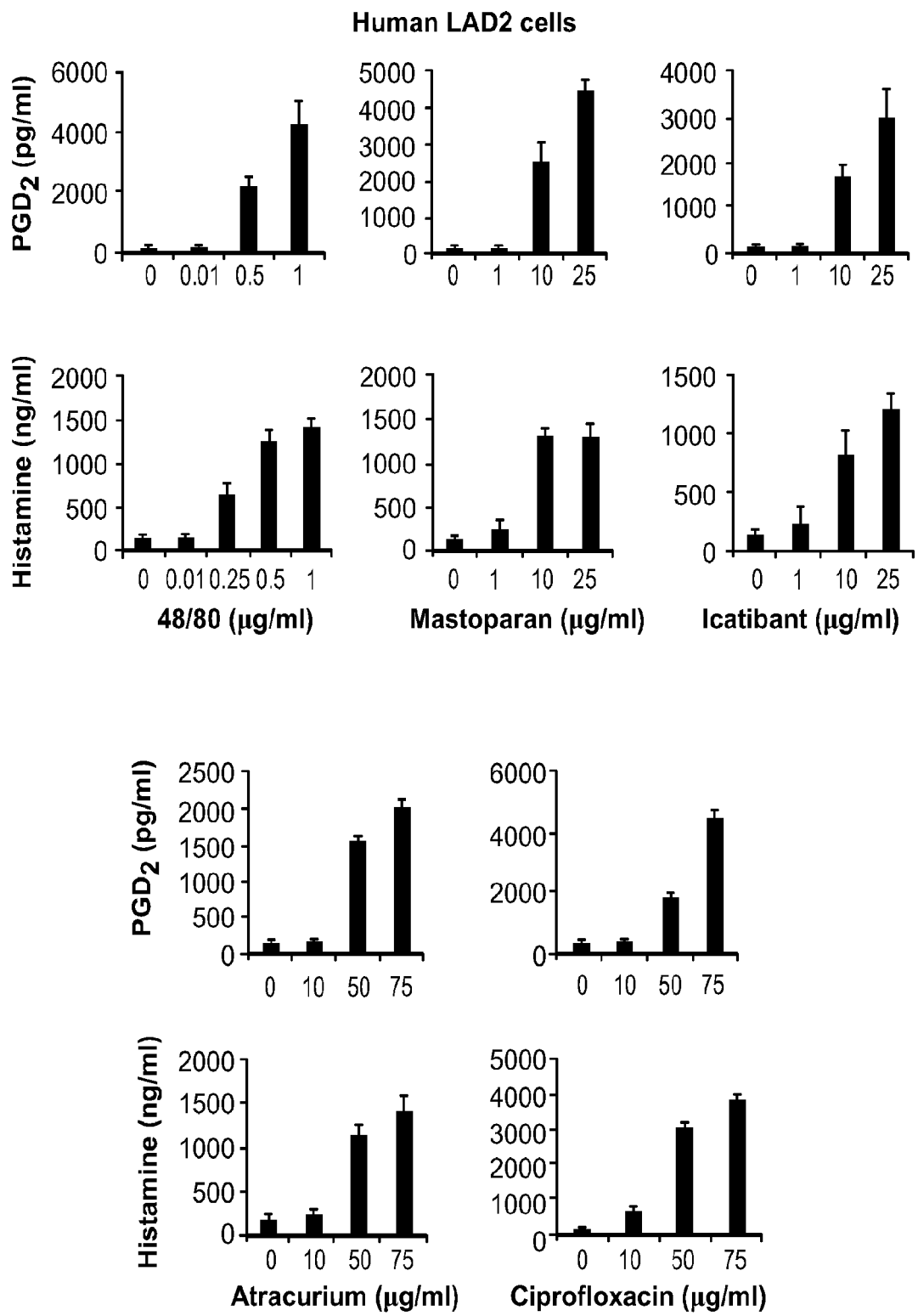
Figure 14B:
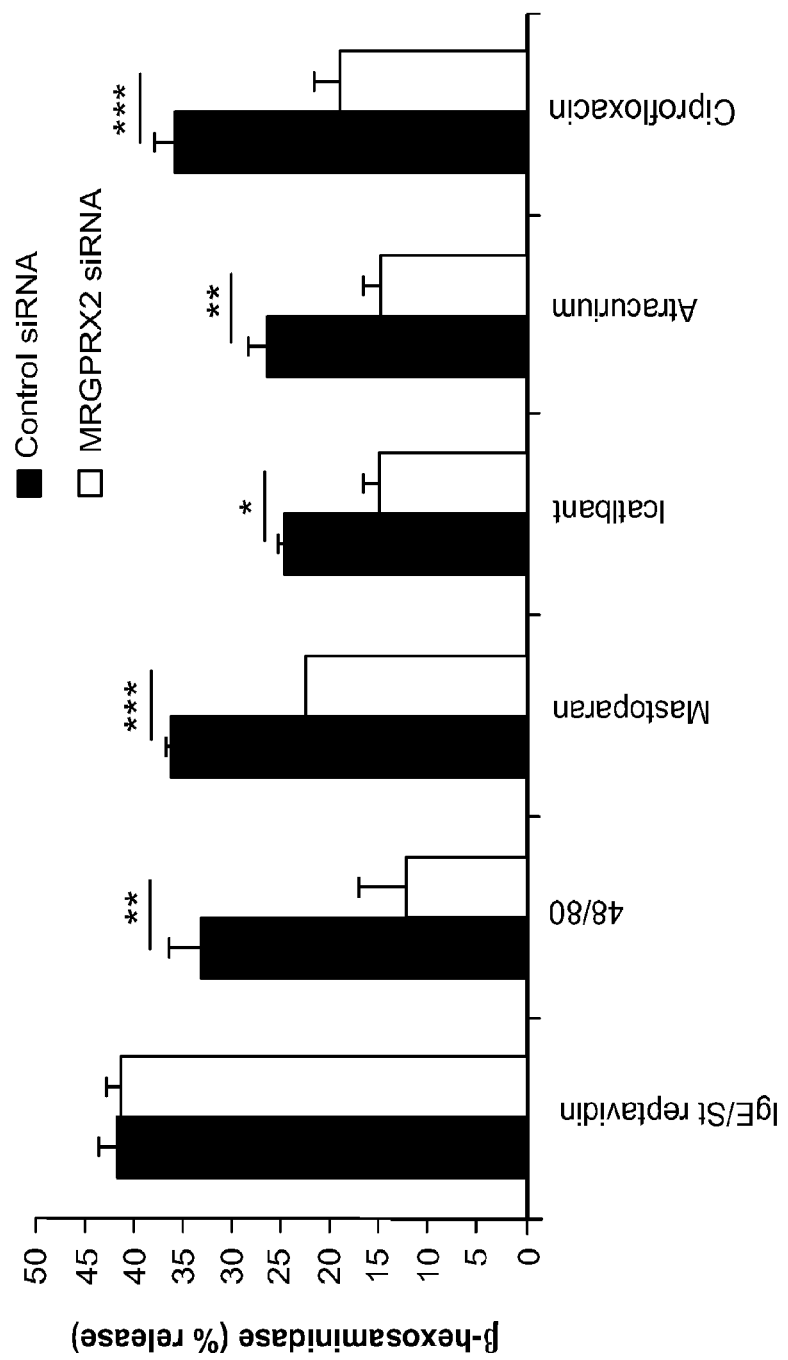

Finally, it was determined whether drugs associated with pseudo-allergies activate human mast cells through MrgprX2. Representative members of each examined drug class evoked release of histamine, TNF, PGD$_2$, and β-hexosaminidase from LAD2 cells (FIG. 14A). 48/80 and mastoparan were used as positive controls. Importantly, MrgprX2 siRNA-treated LAD2 cells exhibited significantly less β-hexosaminidase release evoked by these substances, compared to responses in control siRNA-treated cells, while IgE-mediated release was comparable (FIG. 14B). The remaining release observed in MrgprX2 siRNA-treated cells are likely due to incomplete mRNA and/or protein knockdown.

As described in detail above, MrgprB2 in mice, and MrgprX2 in humans, is the basic secretagogue receptor in mast cells. Also described herein is evidence for the first known in vivo role for this receptor as a critical mediator of IgE-independent drug-induced pseudo-allergies. Thus, knowledge of the role of MrgprX2 in drug-induced pseudo-allergies expands for two reasons. First, ligand binding requirement studies enable more specific screens for drugs that cross-activate MrgprX2. Second, screening orally administered drugs uncovers more MrgprX2 ligands, since common side effects of orally administered drugs include gastrointestinal problems and headache, both which have a mast cell component.

REFERENCES

Bergman, R. K. & Munoz, J. Efficacy of beta-adrenergic blocking agents in inducing histamine sensitivity in mice. Nature 217, 1173-1174 (1968).

Blanca-Lopez, N. et al. Hypersensitivity reactions to fluoroquinolones: analysis of the factors involved. Clin Exp Allergy 43, 560-567 (2013).

Doyle, E., Trosien, J. & Metz, M. Protocols for the induction and evaluation of systemic anaphylaxis in mice. Methods in molecular biology 1032, 133-138, (2013).

Ferry, X., Brehin, S., Kamel, R. & Landry, Y. G protein-dependent activation of mast cell by peptides and basic secretagogues. Peptides 23, 1507-1515 (2002).

Fluker, M. et al. Efficacy and safety of ganirelix acetate versus leuprolide acetate in women undergoing controlled ovarian hyperstimulation. Fertility and sterility 75, 38-45 (2001).

Galli, S. J., Nakae, S. & Tsai, M. Mast cells in the development of adaptive immune responses. Nature immunology 6, 135-142, (2005).

Halpern, B. N. & Wood, D. R. The action of promethazine (phenergan) in protecting mice against death due to histamine. British journal of pharmacology and chemotherapy 5, 510-516 (1950).

Han, L. et al. A subpopulation of nociceptors specifically linked to itch. Nature neuroscience 16, 174-182, (2013).

Harper, N. J. et al. Suspected anaphylactic reactions associated with anaesthesia. Anaesthesia 64, 199-211, (2009).

Hausmann, O., Schnyder, B. & Pichler, W. J. Etiology and pathogenesis of adverse drug reactions. Chemical immunology and allergy 97, 32-46, (2012).

Kamohara, M. et al. Identification of MrgX2 as a human G-protein-coupled receptor for proadrenomedullin N-terminal peptides. Biochemical and biophysical research communications 330, 1146-1152, (2005).

Kashem, S. W. et al. G protein coupled receptor specificity for C3a and compound 48/80-induced degranulation in human mast cells: roles of Mas-related genes MrgX1 and MrgX2. European journal of pharmacology 668, 299-304, (2011).

Kelesidis, T., Fleisher, J. & Tsiodras, S. Anaphylactoid reaction considered ciprofloxacin related: a case report and literature review. Clin Ther 32, 515-526 (2010).

Koppert, W. et al. Different patterns of mast cell activation by muscle relaxants in human skin. Anesthesiology 95, 659-667 (2001).

Lagunoff, D., Martin, T. W. & Read, G. Agents that release histamine from mast cells. Annual review of pharmacology and toxicology 23, 331-351

Liu, Q. et al. Sensory neuron-specific GPCR Mrgprs are itch receptors mediating chloroquine-induced pruritus. Cell 139, 1353-1365, (2009).

Lumry, W. R. et al. Randomized placebo-controlled trial of the bradykinin B(2) receptor antagonist icatibant for the treatment of acute attacks of hereditary angioedema: the FAST-3 trial. Annals of allergy, asthma & immunology: official publication of the American College of Allergy, Asthma, & Immunology 107, 529-537, (2011).

Matsumura, Y., Tan, E. M. & Vaughan, J. H. Hypersensitivity to histamine and systemic anaphylaxis in mice with pharmacologic beta adrenergic blockade: protection by nucleotides. J Allergy Clin Immunol 58, 387-394 (1976).

Mertes, P. M., Alla, F., Trechot, P., Auroy, Y. & Jougla, E. Anaphylaxis during anesthesia in France: an 8-year national survey. J Allergy Clin Immunol 128, 366-373 (2011).

Metcalfe, D., Baram, D. & Mekori, Y. A. Mast cells. Physiological reviews 77, 1033-1079 (1997).

Mori, K., Maru, C. & Takasuna, K. Characterization of histamine release induced by fluoroquinolone antibacterial agents in-vivo and in-vitro. The Journal of pharmacy and pharmacology 52, 577-584 (2000).

Mori, K., Maru, C., Takasuna, K. & Furuhama, K. Mechanism of histamine releaseinduced by levofloxacin, a fluoroquinolone antibacterial agent. European journal of pharmacology 394, 51-55 (2000).

Mousli, M., Hugli, T. E., Landry, Y. & Bronner, C. Peptidergic pathway in human skin and rat peritoneal mast cell activation. Immunopharmacology 27, 1-11 (1994).

Nel, L. & Eren, E. Peri-operative anaphylaxis. British journal of clinical pharmacology 71, 647-658, (2011).

Pundir, P. & Kulka, M. The role of G protein-coupled receptors in mast cell activation by antimicrobial peptides: is there a connection? Immunology and cell biology 88, 632-640, (2010).

Purcell, W. M., Doyle, K. M., Westgate, C. & Atterwill, C. K. Characterisation of a functional polyamine site on rat mast cells: association with a NMDA receptor macrocomplex. Journal of neuroimmunology 65, 49-53 (1996).

Read, G. W. Compound 48-80. Structure-activity relations and poly-THIQ, a new, more potent analog. Journal of medicinal chemistry 16, 1292-1295 (1973).

Robas, N., Mead, E. & Fidock, M. MrgX2 is a high potency cortistatin receptor expressed in dorsal root ganglion. The Journal of biological chemistry 278, 44400-44404, (2003).

Sick, E., Niederhoffer, N., Takeda, K., Landry, Y. & Gies, J. P. Activation of CD47 receptors causes histamine secretion from mast cells. Cellular and molecular life sciences: CMLS 66, 1271-1282, (2009).

Siraganian, R. P. An automated continuous-flow system for the extraction and fluorometric analysis of histamine. Analytical biochemistry 57, 383-394 (1974).

Subramanian, H. et al. beta-Defensins activate human mast cells via Mas-related gene X2. Journal of immunology 191, 345-352, (2013).

Subramanian, H., Gupta, K., Guo, Q., Price, R. & Ali, H. Mas-related gene X2 (MrgX2) is a novel G protein-coupled receptor for the antimicrobial peptide LL-37 in human mast cells: resistance to receptor phosphorylation, desensitization, and internalization. The Journal of biological chemistry 286, 44739-44749, (2011).

Taneike, T., Miyazaki, H., Oikawa, S. & Ohga, A. Compound 48/80 elicits cholinergic contraction through histamine release in the chick oesophagus. General pharmacology 19, 689-695 (1988).

Tatemoto, K. et al. Immunoglobulin E-independent activation of mast cell is mediated by Mrg receptors. Biochemical and biophysical research communications 349, 1322-1328, (2006).

Tuvia, S. et al. Oral octreotide absorption in human subjects: comparable pharmacokinetics to parenteral octreotide and effective growth hormone suppression. The Journal of clinical endocrinology and metabolism 97, 2362-2369, (2012).

Verschraegen, C. F. et al. Phase II study of cetrorelix, a luteinizing hormone-releasing hormone antagonist in patients with platinum-resistant ovarian cancer. Gynecologic oncology 90, 552-559 (2003).

Weigand, L. A., Myers, A. C., Meeker, S. & Undem, B. J. Mast cell-cholinergic nerve interaction in mouse airways. The Journal of physiology 587, 3355-3362, (2009).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A method for reducing the severity of a pseudo-allergic-type reaction in a subject that is induced by administering a compound, the method comprising:
    administering the compound to a subject;
    administering a therapeutically effective amount of a mas-related G-protein coupled receptor member B2(MrgprB2) antagonist or a mas-related G-protein coupled receptor member X2(MrgprX2) antagonist to the subject,
    wherein said MrgprB2 comprises the amino acid sequence of SEQ ID NO: 3 and said MrgprX2 comprises the amino acid sequence of SEQ ID NO: 1.

2. The method of claim 1, wherein a therapeutically effective amount of a mas-related G-protein coupled receptor member B2(MrgprB2) antagonist is administered to the subject.

3. The method of claim 1, wherein a therapeutically effective amount of a mas-related G-protein coupled receptor member X2(MrgprX2) antagonist is administered to the subject.

4. The method of claim 1, wherein the antagonist is an antibody or a fragment thereof, a small molecule, or a nucleic acid molecule.

5. The method of claim 1, wherein the antagonist is an antibody or a fragment thereof.

6. The method of claim 1, wherein the antagonist is a small molecule.

7. The method of claim 1, wherein the antagonist is a nucleic acid molecule.

8. The method of claim 1, wherein the antagonist is a nucleic acid molecule that is double stranded ribonucleic acid (dsRNA), small hairpin RNA or short hairpin RNA (shRNA), or antisense RNA.

9. A method of treating a pseudo-allergic-type reaction in a subject comprising:
    administering a therapeutically effective amount of a mas-related G-protein coupled receptor member B2 (MrgprB2) antagonist or a mas-related G-protein coupled receptor member X2 (MrgprX2) antagonist to the subject,
    wherein said MrgprB2 comprises the amino acid sequence of SEQ ID NO: 3 and said MrgprX2 comprises the amino acid sequence of SEQ ID NO: 1.

10. The method of claim 9, wherein a therapeutically effective amount of a mas-related G-protein coupled receptor member B2(MrgprB2) antagonist is administered to the subject.

11. The method of claim 9, wherein a therapeutically effective amount of a mas-related G-protein coupled receptor member X2(MrgprX2) antagonist is administered to the subject.

12. The method of claim 9, wherein the antagonist is an antibody or a fragment thereof, a small molecule, or a nucleic acid molecule.

13. The method of claim 9, wherein the antagonist is an antibody or a fragment thereof.

14. The method of claim 9, wherein the antagonist is a small molecule.

15. The method of claim 9, wherein the antagonist is a nucleic acid molecule.

16. The method of claim 9, wherein the antagonist is a nucleic acid molecule that is double stranded ribonucleic acid (dsRNA), small hairpin RNA or short hairpin RNA (shRNA), or antisense RNA.

* * * * *